US008906915B2

(12) United States Patent
De Keersmaecker et al.

(10) Patent No.: US 8,906,915 B2
(45) Date of Patent: Dec. 9, 2014

(54) COMPOUNDS, COMPOSITIONS, AND METHODS FOR CONTROLLING BIOFILMS

(75) Inventors: Sigrid De Keersmaecker, Tienen (BE); Dirk De Vos, Holsbeek (BE); Denis Ermolatev, Heverlee (BE); Hans Steenackers, Waanrode (BE); Erik Van Der Eycken, Ninove (BE); Jozef Vanderleyden, Heverlee (BE); Bharat S. Savaliya, Gujarat (IN)

(73) Assignee: Katholieke Universiteit Leuven, K.U.Leuven R&D, Leuven (BE)

( * ) Notice: Subject to any disclaimer, the term of this patent is extended or adjusted under 35 U.S.C. 154(b) by 24 days.

(21) Appl. No.: 13/526,235

(22) Filed: Jun. 18, 2012

(65) Prior Publication Data

US 2013/0029981 A1 Jan. 31, 2013

Related U.S. Application Data

(63) Continuation-in-part of application No. PCT/EP2010/070149, filed on Dec. 17, 2010.

(30) Foreign Application Priority Data

Dec. 17, 2009 (GB) .................................. 0922087.2
Dec. 17, 2009 (GB) .................................. 0922089.8
Dec. 23, 2009 (GB) .................................. 0922423.9
Dec. 23, 2009 (GB) .................................. 0922424.7
May 20, 2010 (GB) .................................. 1008365.7

(51) Int. Cl.
*A61K 31/535* (2006.01)
*C07D 487/04* (2006.01)
*C07D 405/12* (2006.01)
*C07D 233/88* (2006.01)
*C07D 409/04* (2006.01)

(52) U.S. Cl.
CPC ............ *C07D 233/88* (2013.01); *C07D 487/04* (2013.01); *C07D 405/12* (2013.01); *C07D 409/04* (2013.01)
USPC ..................................... 514/235.8; 514/233.2

(58) Field of Classification Search
CPC .. C07D 401/12; C07D 401/14; C07D 487/04; C07D 471/04
USPC .......... 514/232.8, 233.2, 235.5, 235.8, 259.1, 514/259.5
See application file for complete search history.

(56) References Cited

U.S. PATENT DOCUMENTS

| | | |
|---|---|---|
| 2003/0100593 A1 | 5/2003 | Liu et al. |
| 2008/0146634 A1 | 6/2008 | Galley et al. |
| 2009/0018150 A1 | 1/2009 | Borman et al. |
| 2009/0270475 A1 | 10/2009 | Melander et al. |

FOREIGN PATENT DOCUMENTS

| | | |
|---|---|---|
| EP | 0902018 A2 | 3/1999 |
| EP | 0902018 A3 | 5/2001 |
| GB | 1477750 | 6/1977 |
| GB | 2202042 | 9/1988 |
| WO | WO 94/28898 | 12/1994 |
| WO | WO 01/44203 | 6/2001 |
| WO | WO 02/40453 | 5/2002 |
| WO | WO 2005/005394 | 1/2005 |
| WO | WO 2005/012263 | 2/2005 |
| WO | WO 2006/107923 | 10/2006 |
| WO | WO 2008/071574 | 6/2008 |
| WO | WO 2008/094479 | 8/2008 |
| WO | WO 2009/070304 | 6/2009 |
| WO | WO 2009/123753 | 10/2009 |

OTHER PUBLICATIONS

Ermolat'ev et al., "One-pot microwave-assisted protocol for the synthesis of substituted 2-amino-1H-imidazoles", May 2011, Molecular Diversity, 15(2), pp. 491-496.*
Steenackers et al., "Structure-Activity Relationship of 4(5)-Aryl-2-amino-1H-imidazoles, N1-Substituted 2-Aminoimidazoles and Imidazo[1,2-a]pyrimidinium Salts as Inhibitors of Biofilm Formation by *Salmonella typhimurium* and *Pseudomonas aeruginosa*", 2011, J. Med. Chem., 54 (2), pp. 472-484.*
Steenackers et al., "Structure-activity relationship of 2-hydroxy-2-aryl-2,3-dihydroimidazo[1,2-a]pyrimidinium salts and 2N-substituted 4(5)-aryl-2-amino-1H-imidazoles as inhibitors of biofilm formation by *Salmonella typhimurium* and *Pseudomonas aeruginosa*", Jun. 1, 2011, Bioorganic & Medicinal Chemistry, 16(11), pp. 3462-3473.*
Boselli et al., "Antibacterial activity of clonidine and neostigmine in vitro," *Anesth. Analg.* 101:121-124 (2005).
Claerhout et al., "A new colorimetric test for solid-phase amines and thiols," *J. Comb. Chem.* 10:580-585 (2008).

(Continued)

*Primary Examiner* — My-Chau T Tran
(74) *Attorney, Agent, or Firm* — Clark & Elbing LLP

(57) ABSTRACT

The invention relates to substituted 2-aminoimidazoles and their imidazo[1,2-a]pyrimidinium salts precursors being active against biofilm formation. The invention also relates to imidazo[1,2-a]pyrimidinium salts bearing an azidoalkyl substituent, and to substituted 2-aminoimidazoles wherein the amino group bears a terminal heterocyclic group such as a triazolyl group which are formed through azide-alkyne Huisgen cycloaddition starting from said imidazo[1,2-a]pyrimidinium salts bearing an azidoalkyl substituent. The invention also relates to a class of N-(azidoalkyl)pyrimidin-2-amines useful as starting materials for the synthesis of said imidazo[1,2-a]pyrimidinium salts bearing an azidoalkyl substituent. The invention also relates to antimicrobial compositions that include a microbial biofilm formation inhibiting amount of such substituted 2-aminoimidazoles or imidazo[1,2-a]pyrimidinium salts in combination with excipients. Methods for inhibiting or controlling microbial biofilm formation in a plant, a body part of a human or an animal, or a surface with which a human or an animal may come into contact are also disclosed.

18 Claims, 2 Drawing Sheets

(56) References Cited

OTHER PUBLICATIONS

Ermolat'ev et al., "A divergent synthesis of substituted 2-aminoimidazoles from 2-aminopyrimidines," *J. Org. Chem.* 73:6691-6697 (2008).
Gohibushina et al., "Reaction of 1-amino-, 2-amino-, and 1,2-diaminoimidazoles with diketones β-diketones," *Khimiya Geterosiklicheskikh* 6:846-850 (1974) (Russian Language).
Lisunkin et al., "Synthesis and pharmacological properties of some new condensed derivatives of benzthiazolin, thiazolo and benzthiazolo-pyrimidinum," *Farmatsevtichnii Zhurnal (Kiev)* 26:20-25 (1971) (Russian Language).
Marrero-Ponce et al., "Atom, atom-type, and total nonstochastic and stochastic quadratic fingerprints: a promising approach for modeling of antibacterial activity," *Bioorg. & Med. Chem.* 13:2881-2899 (2005).
Mloston et al., "Reactions of 2-unsubstituted 1*H*-imidazole 3-oxides with heterocumulenes and dimethyl acetylenedicarboxylate," *Tetrahedron* 56:5405-5412 (2000).
Search Report for U.K. Patent Application No. GB0922087.2, dated May 11, 2010 (4 pages).
Search Report for U.K. Patent Application No. GB0922089.8, dated Apr. 19, 2010 (4 pages).
Search Report for U.K. Patent Application No. GB0922423.9, dated May 19, 2010 (4 pages).
International Search Report for International Application No. PCT/EP2010/070149, completed Jul. 29, 2011, mailed May 8, 2011 (4 pages).
International Preliminary Report on Patentability for International Application No. PCT/EP2010/070149, issued Jun. 19, 2012 (11 pages).
Written Opinion of the International Searching Authority for International Application No. PCT/EP2010/070149, completed Jul. 29, 2011, mailed May 8, 2011 (9 pages).
Communication pursuant to Article 94(3) EPC for European Patent Application No. 10803455.4, dated Feb. 11, 2014 (5 pages).

\* cited by examiner

Table 8

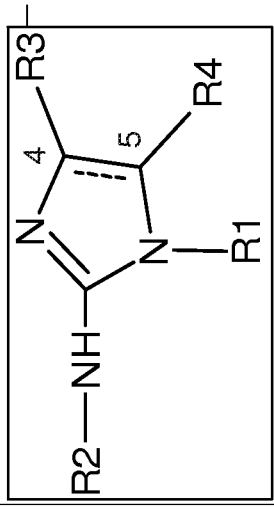

| R1 | R2 | R3 | R4 | C4-C5 bond | Salmonella typhimurium ATCC14028 | | | Pseudomonas aeruginosa PA14 | | |
|---|---|---|---|---|---|---|---|---|---|---|
| | | | | | IC50 biofilm inhibition (25°C) (µM) | Influence on growth (25°C) | IC50 biofilm inhibition (37°C) (µM) | IC50 biofilm inhibition (25°C) (µM) | Influence on growth (25°C) | IC50 biofilm inhibition (37°C) (µM) |
| H | Me | H | p-FPh | double | 102 | x | nd | nd | | nd |
| H | i-Pr | H | p-MePh | double | 99 | x | nd | nd | | nd |
| H | Bu | H | Ph | double | 25 | x | nd | nd | | nd |
| H | Bu | H | p-FPh | double | 16 | x | nd | 6 | x | >100 |
| H | Bu | H | p-BrPh | double | 7 | x | >100 | nd | | nd |
| H | Bu | H | p-MeOPh | double | 49 | x | nd | nd | | nd |
| H | c-Pr | H | p-BrPh | double | 5 | x | nd | nd | | nd |
| H | c-Pen | H | Ph | double | 53 | x | nd | nd | | nd |
| H | c-Pen | H | p-ClPh | double | 4 | x | >100 | nd | | nd |
| H | c-Pen | H | p-BrPh | double | 12 | x | >100 | nd | | nd |
| H | c-Pen | H | p-NO2Ph | double | 12 | x | nd | nd | | nd |
| H | c-Pen | H | biPh | double | 46 | x | nd | nd | | nd |
| H | c-Pen | H | 3,4-diClPh | double | 6 | x | nd | 1 | x | >100 |
| H | c-Hex | H | p-NO2Ph | double | 44 | x | nd | nd | | nd |

Table 8 (continued)

| | | | | | | | |
|---|---|---|---|---|---|---|---|
| H | Bn | H | p-ClPh | double | 31 | x | nd | nd | nd |
| H | piperonyl | H | p-FPh | double | 68 | x | nd | nd | nd |
| H | 2-(3-MeOPh)Et | | p-No2Ph | double | 15 | x | nd | | nd |
| H | S1[d] | H | H | single | | x | nd | nd | nd |
| H | S2[e] | H | H | single | | x | nd | nd | nd |
| H | S3[f] | H | H | single | | x | nd | nd | nd |
| H | S4[g] | H | H | single | | x | nd | nd | nd |

COMPOUNDS, COMPOSITIONS, AND METHODS FOR CONTROLLING BIOFILMS

CROSS REFERENCE TO RELATED APPLICATIONS

This application is a continuation-in-part of International application No. PCT/EP2010/070149, filed on Dec. 17, 2010, which, in turn, claims the benefit of British Patent Application No. 0922087.2 filed on Dec. 17, 2009, British Patent Application No. 0922089.8 filed on Dec. 17, 2009, British Patent Application No. 0922424.7 filed on Dec. 23, 2009, British Patent Application No. 0922423.9 filed on Dec. 23, 2009 and British Patent Application No. 1008365.7 filed on May 20, 2010. Each of the aforementioned disclosures are hereby incorporated by reference in their entirety.

FIELD OF THE INVENTION

The present invention relates to substituted 2-aminoimidazoles and their imidazo[1,2-a]pyrimidinium salts precursors being active against biofilm formation. The present invention also relates to imidazo[1,2-a]pyrimidinium salts bearing an azidoalkyl substituent, and to substituted 2-aminoimidazoles wherein the amino group bears a terminal heterocyclic group such as a triazolyl group which may be formed through azide-alkyne Huisgen cycloaddition starting from said imidazo[1,2-a]pyrimidinium salts bearing an azidoalkyl substituent. The present invention also relates to a class of N-(azidoalkyl)pyrimidin-2-amines which are useful as starting materials for the synthesis of said imidazo[1,2-a]pyrimidinium salts bearing an azidoalkyl substituent. The present invention also relates to antimicrobial compositions comprising a microbial biofilm formation inhibiting amount of such substituted 2-aminoimidazoles or imidazo[1,2-a]pyrimidinium salts in combination with excipients. The present invention also relates to methods for inhibiting or controlling microbial biofilm formation in a plant, a body part of a human or an animal, or a surface with which a human or an animal may come into contact.

The present invention relates to compounds, compositions and methods for controlling biofilms and microbial, in particular bacterial, growth and for reducing bacterial colonization. The present invention relates to the treatment and prevention of infectious diseases caused by microbial biofilm formation, in particular to antimicrobial prophylactic and therapeutic compositions containing an effective amount of a biofilm formation inhibitor to reduce or eliminate colonization with potentially pathogenic microorganisms, more particularly bacteria (including bacterial strains resistant to many or most common antimicrobial agents), thereby reducing the risk of subsequent disease occurrence. Furthermore the present invention relates to compounds, and to compositions and methods involving these compounds, for inhibiting, reducing or preventing the formation of a biofilm on a surface of a medical device such as a catheter, or on a tissue such as teeth, urethra or lungs of a human (e.g. a cystic fibrosis patient). These compounds, compositions and methods of present invention are in particular useful for preventing biofilm formation in a tissue to prevent or control a chronic bacterial infection or sepsis, and also useful for sanitation when applied to a substrate with which a human or an animal may come into contact.

BACKGROUND OF THE INVENTION

Biofilms are defined in the art as structured communities or aggregates of microorganisms (e.g. bacterial cells) in which cells adhere to each other and/or to a living or inert (non-living) surface. These adherent cells are frequently embedded within a self-produced matrix of extracellular polymeric substance. Biofilms represent a prevalent mode of microbial life in natural, industrial and hospital settings. The microbial cells growing in a biofilm are physiologically distinct from planktonic cells of the same organism. Biofilm cells exhibit profound changes in gene expression and cell physiology compared with planctonic cells, and multiple genetic pathways mediate the regulation of biofilm formation. Microorganisms in biofilms form microbial colonies or condominiums that make it easy to carry out chemical reactions that are impossible for individual microbial cells. Biofilms can contain many different types of microorganism, e.g. bacteria, archaea, protozoa, fungi and algae.

The use of effective antimicrobial compositions to avoid biofilm formation is recommended for any surface in contact with water, such as swimming pool liners, water cooling surfaces, hoses, water dispensers, water storage and distribution systems for drinking water or aquaculture, and for surfaces of medical devices such as catheters, medical implants, wound dressings and the like, especially when intended for patients with metabolic disorders.

Biofilms are known to provide cells with an array of advantages as compared with planktonic cells including the ability to resist challenges from predators, antibiotics, disinfectants and host immune systems. Biofilms offer a selective advantage to a microorganism to ensure its survival, or allow it a certain amount of time to exist in a dormant state until suitable growth conditions arise which for instance provide bacteria protection from antibiotics and from a host's immune system. This causes serious problems and costs in medical, hospital and industrial settings.

Biofilms are believed to be involved in 80% of human bacterial infections such as periodontitis, gingivitis, urethritis, endocarditis, benign prostatic hyperplasia, chronic prostatitis, biliary tract infections, urinary tract infections, cystitis, lung infections, sinus infections, ear infections (e.g. otitis media, otitis externa), acne and other skin infections, rosacea, dental caries, dental plaque formation, nosocomial infections, open wounds, chronic wounds and device-associated infections. There is thus a need in the art to control biofilm formation. A biofilm inhibitor may be useful to clear the way for a bactericide to penetrate the affected cells and eradicate the infection or it can provide an alternative treatment approach for certain types of infections.

Biofilms can contribute to contaminating food (food industry), decreasing flow through pipelines by colonization of the pipe interior or mild steel corrosion (oil industry), initiating biofouling on vessel hulls (shipping industry), and infesting hospitals, in particular surgery rooms and medical devices used therein. Biofilm formation in combination with mineral deposition may reduce heat transfer in water based cooling plants There is thus also a need in the art for compounds and methods for preventing biofilm formation regulated mineral deposition. Valuable plants such as those producing fruits and vegetables, forestry crops, corn, cotton, rice, soybeans and wheat are affected in a deleterious manner by biofilm formation and hence need protection from biofilm formation.

US 2003/100593 teaches, but without biological evidence, that certain substituted 2-aminoimidazoles are useful for treating various diseases including cardiovascular disorders, Kaposi sarcoma, cancer, bacterial infections, migraine, allergy and osteoporosis.

WO 2009/070304 teaches 2-aminoimidazoles useful for controlling biofilms and bacterial infections in plants. WO 2009/123753 teaches 2-aminoimidazoles useful for inhibiting bacterial biofilms.

Organic Letters (2006) 8:5781-4 and J. Org. Chem. (2008) 73:6691-7 disclose a few imidazo[1,2-a]pyrimidinium salts as precursors of substituted 2-aminoimidazoles, but do not attribute any utility to these compounds.

J. Org. Chem. (1993) 58:3736-3741 and U.S. Patent Application Publication both describe methods for the synthesis of azidoalkylamines. The azide-alkyne Huisgen cycloaddition is a well known 1,3-dipolar cycloaddition method between an azide and a terminal or internal alkyne to provide a 1,2,3-triazole ring.

One object of the present invention is to address one or more of the above listed needs by providing efficient agents for reducing, controlling or inhibiting biofilm formation, such agents being either specifically acting on biofilm formation without influencing the planktonic growth of microorganisms, or being acting both on biofilm formation and planktonic growth in the same concentration range. Another object of the present invention is to provide new synthetic methods for producing such efficient biofilm formation inhibitors and precursors thereof.

SUMMARY OF THE INVENTION

The present invention relates to a broad group of substituted imidazo[1,2-a]pyrimidinium salts, substituted 2-aminoimidazoles and substituted 2-amino-imidazolines, most of them being unknown in the literature, which exhibit outstanding utility in controlling microbial biofilm formation, especially against a wide range of bacteria, and therefore can be formulated into anti-microbial compositions for administration to humans and animals and for application to plants and to inert surfaces susceptible to infection by microbial biofilms.

A first aspect of the present invention thus relates to a group of substituted imidazo[1,2-a]pyrimidinium salts and substituted 2-aminoimidazoles which are not known in the literature. Within this aspect the present invention specifically relates to a compound selected from the group consisting of:

substituted 2-aminoimidazoles represented by the structural formula (I),

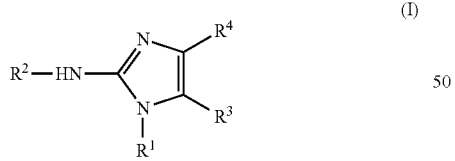

wherein
$R^1$ is selected from the group consisting of hydrogen, $C_{1-20}$ alkyl, $C_{2-20}$ alkenyl, $C_{2-20}$ alkynyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cyclolkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, amino, sulfhydryl, oxo, $C_{1-20}$ alkylthio and nitro, with the proviso that when $R^1$ is methyl, said methyl is not di- or tri-substituted with one phenyl and one or two further alkyl, aryl or heterocyclic substituents;

$R^2$ is selected from the group consisting of $C_{1-20}$ alkyl, $C_{1-20}$ alkylcarbonyl, $C_{2-20}$ alkenyl, $C_{2-20}$ alkynyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, sulfhydryl, alkylthio and nitro, and wherein each of said aryl, heterocyclic and oxo, oxo $C_{1-20}$ heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo-$C_{1-20}$ alkoxy, aryloxy, arylthio, amino, sulfhydryl, oxo, $C_{1-20}$ alkylthio and nitro;

$R^3$ is selected from the group consisting of hydrogen, aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, phenyl, methylsulfonyl, amino, sulfhydryl, oxo, $C_{1-20}$ alkylthio and nitro;

$R^4$ is selected from the group consisting of hydrogen, $C_{1-20}$ alkyl, $C_{3-12}$ cycloalkyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, amino, sulfhydryl, oxo, $C_{1-20}$ alkylthio and nitro;

with the proviso that said substituted 2-aminoimidazole is not one defined by the substituting pattern ($R^1$, $R^2$, $R^3$, $R^4$) of the following table

| R1 | R2 | R3 | R4 |
| --- | --- | --- | --- |
| H | Ethyl | CONH-ethyl | H |
| H | Cyclopropyl | Morpholin-4-ylcarbonyl | H |
| H | Cyclohexyl | 3-nitrophenyl | H |
| H | Cyclododecyl | 3-nitrophenyl | H |
| H | 4-methoxybenzyl | 4-nitrophenyl | H |
| H | Piperonyl | 4-fluorophenyl | H |
| H | Hexyl | Phenyl | Methyl |
| H | Methoxyethyl | 4-fluorophenyl | Methyl |
| H | Homoveratryl | 4-chlorophenyl | Phenyl |
| H | Tert-butyl | 4-chlorophenyl | 4-tolyl |
| H | methyl | 4-nitrophenyl | H |
| H | benzyl | 4-chlorophenyl | H | and
imidazo[1,2-a]pyrimidinium salts represented by the structural formula (II)

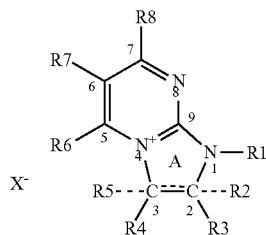

(II)

wherein ... at $C_2$-$C_3$ represents an optional double bond, in which case $R^2$ and $R^5$ are absent, so that either ring A is an imidazolinyl structure represented by formula B

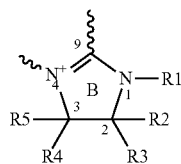

or ring A is an imidazolyl structure represented by formula C

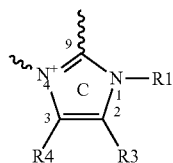

and wherein

R1, R4 and R5 are each independently selected from the group consisting of hydrogen, $C_{1-20}$ alkyl, $C_{2-20}$ alkenyl, $C_{2-20}$ alkynyl, $C_{1-20}$ alkylcarbonyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R2 is hydroxy,

R3 is selected from the group consisting of hydrogen, aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R6, R7, R8 are each independently selected from the group consisting of hydrogen, hydroxy, halogen, amino, $C_{1-20}$ alkoxy, $C_{1-20}$ alkyl, $C_{2-20}$ alkenyl, $C_{3-12}$ cycloalkyl and $C_{3-12}$ cycloalkenyl; and $X^-$ is an anion, with the proviso that said imidazo[1,2-a]pyrimidinium salt is not one wherein R5, R6, R7 and R8 are each hydrogen and wherein the substituting pattern ($R^1$, $R^3$, $R^4$) is as defined in the following tables

| R1 | R3 | R4 |
|---|---|---|
| methyl | phenyl | H |
| ethyl | phenyl | H |
| n-butyl | phenyl | H |
| n-pentyl | phenyl | H |
| cyclopropyl | phenyl | H |
| cyclopentyl | phenyl | H |
| ethyl | 4-fluorophenyl | H |
| ethyl | 4-chlorophenyl | H |
| ethyl | 4-bromophenyl | H |
| ethyl | 4-iodophenyl | H |
| methyl | 4-(methylthio)phenyl | H |
| benzyl | phenyl | H |
| 4-methoxybenzyl | phenyl | H |
| methyl | 3,4,5-trimethoxyphenyl | H |
| methyl | 2,5-dimethoxyphenyl | H |
| methyl | H | benzyl |
| benzyl | H | benzyl |
| methyl | H | 4-methoxybenzyl |
| 4-methoxyphenylethyl | phenyl | methyl |
| phenyl | 4-chlorophenyl | p-tolyl |
| cyclohexyl | phenyl | methyl |
| n-propyl | 4-fluorophenyl | methyl |
| cyclohexyl | phenyl | phenyl |
| 4-methoxyphenylethyl | phenyl | phenyl |
| methoxyethyl | 4-bromophenyl | methyl |
| cyclopentyl | 4-bromophenyl | methyl |
| isobutyl | 4-chlorophenyl | p-tolyl |

| R1 | R3 | R4 |
|---|---|---|
| methyl | 4-fluorophenyl | H |
| methyl | 4-nitrophenyl | H |
| benzyl | 4-chlorophenyl | H |
| isopropyl | 4-biphenylyl | H |
| cyclohexyl | 4-cyanophenyl | H |
| cyclohexyl | 4-chlorophenyl | H |
| cyclododecyl | 4-nitrophenyl | H |
| methyl | 4-chlorophenyl | H |
| methyl | 4-cyanophenyl | H |
| 2-bromophenyl | phenyl | H |
| 3,4-dimethoxyphenylethyl | phenyl | H |
| 4-methoxyphenyl | 4-(trifluoromethyl)phenyl | H |
| methyl | H | 4-methoxyphenyl |
| 4-methoxybenzyl | H | 4-methoxybenzyl |
| H | 4-cyanophenyl | H |
| H | 4-nitrophenyl | H |
| ethyl | CONH-ethyl | H |
| cyclopropyl | morpholin-4-ylcarbony | H |
| cyclohexyl | 3-nitrophenyl | H |
| cyclododecyl | 3-nitrophenyl | H |
| 4-methoxybenzyl | 4-nitrophenyl | H |
| piperonyl | 4-fluorophenyl | H |
| hexyl | phenyl | methyl |
| methoxyethyl | 4-fluorophenyl | methyl |
| homoveratryl | 4-chlorophenyl | phenyl |
| tert-butyl | 4-chlorophenyl | 4-tolyl | and pharmaceutically acceptable salts, hydrates, solvates, prodrugs, stereoisomers or polymorphic forms thereof.

This first aspect of the invention further relates to imidazo[1,2-a]pyrimidinium salts represented by the structural formula (II) wherein R1, R4 and R5 are each independently selected from the group consisting of $C_{1-20}$ alkyl, $C_{2-20}$ alkenyl, $C_{2-20}$ alkynyl, $C_{3-12}$ cycloalkyl and $C_{3-12}$ cycloalkenyl and are substituted with one or more azido groups, preferably wherein R1 is $C_{1-20}$ alkyl substituted with one terminal azido group.

In view of the biological properties that have been evidenced in these compounds, a second aspect of the present invention relates to anti-microbial compositions comprising a biologically effective amount of a substituted imidazo[1,2-a]pyrimidinium salt or a substituted 2-aminoimidazole such as defined in the first aspect of the invention hereinabove, or a compound of the same group being known from the literature but without an associated utility, or a substituted 2-aminoimidazoline known from the literature but without an associated utility. Within this second aspect the present invention relates to an antimicrobial composition comprising one or more excipients and a biofilm inhibiting amount of a compound selected from the group consisting of:

substituted 2-aminoimidazoles represented by the structural formula (I)

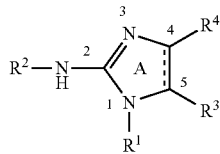

(I)

wherein ... at $C_4$-$C_5$ represents an optional double bond, so that ring A is either an imidazolyl structure represented by formula (B)

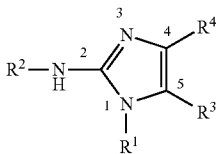

(B)

or an imidazolinyl structure represented by formula (C)

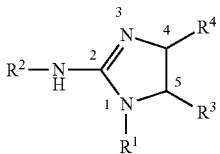

(C)

wherein
$R^1$ is selected from the group consisting of hydrogen, $C_{1-20}$ alkyl, $C_{2-20}$ alkenyl, $C_{2-20}$ alkynyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cyclolkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, amino, sulfhydryl, oxo, $C_{1-20}$ alkylthio and nitro;

$R^2$ is selected from the group consisting of $C_{1-20}$ alkyl, $C_{2-20}$ alkenyl, $C_{2-20}$ alkynyl, $C_{3-12}$ cycloalkyl, $C_{3-12}$ cyclolkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo-$C_{1-20}$ alkyl, $C_{1-20}$ alkoxy, halo-$C_{1-20}$ alkoxy, aryloxy, arylthio, amino, sulfhydryl, oxo, $C_{1-20}$ alkylthio and nitro;

$R^3$ is selected from the group consisting of hydrogen, $C_{1-20}$ alkyl, $C_{3-12}$ cycloalkyl, aryl, heterocyclic and heteroaryl, wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, methylsulfonyl, amino, sulfhydryl, oxo, $C_{1-20}$ alkylthio and nitro;

$R^4$ is selected from the group consisting of hydrogen, $C_{1-20}$ alkyl, $C_{3-12}$ cycloalkyl, aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, amino, sulfhydryl, oxo, $C_{1-20}$ alkylthio and nitro;

with the proviso that when ring A is an imidazolyl structure represented by formula (B) and $R^1$ is methyl, said methyl is not di- or tri-substituted with one phenyl and one or two further alkyl, aryl or heterocyclic substituents; and imidazo[1,2-a]pyrimidinium salts represented by the structural formula (II)

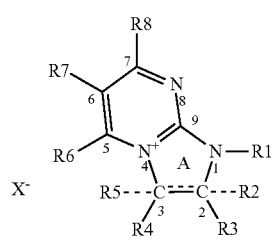

(II)

wherein ... at $C_2$-$C_3$ represents an optional double bond, in which case R2 and R5 are absent, so that either ring A is an imidazolinyl structure represented by formula (B)

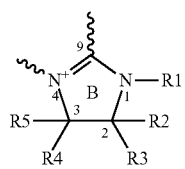

or ring A is an imidazolyl structure represented by formula (C)

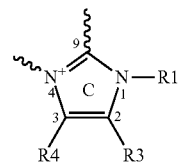

and wherein

R1, R4 and R5 are each independently selected from the group consisting of hydrogen, $C_{1-20}$ alkyl, $C_{2-20}$ alkenyl, $C_{2-20}$ alkynyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, azido, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R2 is hydroxy; and

R3 is selected from the group consisting of hydrogen, aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R6, R7, R8 are each independently selected from the group consisting of hydrogen, hydroxy, halogen, amino, $C_{1-20}$ alkoxy, $C_{1-20}$ alkyl, $C_{2-20}$ alkenyl, $C_{1-20}$ cycloalkyl, $C_{2-20}$ cycloalkenyl; and $X^-$ is an anion, and pharmaceutically acceptable salts, hydrates, solvates, prodrugs, stereoisomers or polymorphic forms thereof.

This second aspect of the invention further relates to antimicrobial compositions comprising a biofilm inhibiting amount of an imidazo[1,2-a]pyrimidinium salt represented by the structural formula (II) wherein R1, R4 and R5 are each independently selected from the group consisting of $C_{1-20}$ alkyl, $C_{2-20}$ alkenyl, $C_{2-20}$ alkynyl, $C_{3-12}$ cycloalkyl and $C_{3-12}$ cycloalkenyl and are substituted with one or more azido groups, preferably wherein R1 is $C_{1-20}$ alkyl substituted with one terminal azido group.

A third aspect of the present invention relates to the use of a substituted imidazo[1,2-a]pyrimidinium salt, a substituted 2-aminoimidazole or a substituted 2-aminoimidazoline as defined in the second aspect hereinabove as an inhibitor of microbial biofilm formation. Depending upon the target microbe, the use may be for inhibiting bacterial biofilm formation, or protozoal biofilm formation, or fungal biofilm formation, or algal biofilm formation. Although in most situations the compounds of this invention are only acting on microbial biofilm formation, some of them may also influence the planktonic growth of microorganisms in the same or a similar concentration range. Thus the present invention also relates to a method as defined in claim 24 of International Application No. PCT/EP2010/070149 (which is hereby incorporated by reference), i.e. making use of an anti-microbial composition as defined in the second aspect of the invention.

Each main aspect of the present invention will now be described with reference to a certain number of specific embodiments and working examples. Terms used in claims 1, 9 and 24 of International Application No. PCT/EP2010/070149 (each of which is hereby incorporated by reference) defining the broadest concept for each main aspect of the present invention are defined below.

BRIEF DESCRIPTION OF THE DRAWINGS

FIG. 1 shows the effect of certain compounds of the invention on planktonic growth at the IC50 concentration for biofilm inhibition.

DEFINITIONS

The term "optionally substituted" indicates that the specified group is either unsubstituted, or substituted by one or more suitable substituents. A "substituent" as defined herein is a monovalent atom or group of atoms replacing a hydrogen atom on a hydrocarbon chain or cycle (ring) of an organic molecule, for example halogen, hydroxy, acyl, alkyl, alkenyl, alkynyl, cycloaliphatic, heterocyclo, aryl (in particular phenyl), heteroaryl, alkoxy, amino, amido, azido, sulfhydryl, alkylthio, alkylsulfonyl, nitro, carbonyl, carboxy, amino-acid (both natural and synthetic) and peptido, or a divalent atom replacing two hydrogen atoms on the same carbon atom of a hydrocarbon chain, for instance oxo or thioxo. The number of admissible substituents depends upon the number of hydrogen atoms that can be replaced, thus the chain length, the type of substituent and parameters such as steric hindrance which are well known to the skilled person.

The term "aliphatic" as used herein refers to "Alkyl", "Alkenyl" or "Alkynyl".

The term "alkyl" or "saturated aliphatic" as used herein, and unless otherwise specified, refers to a straight or branched hydrocarbon chain containing from 1 to 20 (e.g. 2, 3, 4, 5, 6, 7, 8, 9, 10, 11, 12, 13, 14, 15, 16, 17, 18, 19) carbon atoms, hence the notation $C_{1-20}$ alkyl. Representative examples of $C_{1-20}$ alkyl include, but are not limited to, methyl, ethyl, n-propyl, isopropyl, n-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Such alkyl groups may optionally be substituted with one or more (e.g. 2, 3 or 4) substituents as defined hereinabove.

"Alkenyl," as used herein, refers to a straight or branched hydrocarbon chain containing from 2 to 20 (e.g. 3, 4, 5, 6, 7, 8, 9, 10, 11, 12, 13, 14, 15, 16, 17, 18, 19) carbon atoms, hence the notation $C_{2-20}$ alkenyl, and containing at least one carbon-carbon double bond (either terminal or internal). Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, butadienyl, hexadienyl and the like. Such alkenyl groups may optionally be substituted with one or more (e.g. 2, 3 or 4) substituents as defined hereinabove.

"Alkynyl" as used herein, refers to a straight or branched hydrocarbon chain containing from 2 to 20 (e.g. 3, 4, 5, 6, 7, 8, 9, 10, 11, 12, 13, 14, 15, 16, 17, 18, 19) carbon atoms, hence the notation $C_{2-20}$ alkynyl, and containing at least one carbon-carbon triple bond (either terminal or internal). Representative examples of $C_{2-20}$ alkynyl include, but are not limited, to acetylenyl, 1-propynyl, 2-propynyl, 3-butynyl, 2-pentynyl, 1-butynyl and the like. Such alkynyl groups may optionally be substituted with one or more (e.g. 2, 3 or 4) substituents as defined hereinabove.

The term "cycloaliphatic", as used herein and unless otherwise specified, refers to a saturated or ethylenically unsaturated monocyclic or polycyclic hydrocarbon group containing from 3 to 12 (e.g. 4, 5, 6, 7, 8, 9 or 10) carbon atoms, which is not aromatic, hence the notations $C_{3-12}$ cycloalkyl (saturated) and $C_{3-12}$ cycloalkenyl (unsaturated). Representative examples of cycloalkyl include, but are not limited to, cyclopropyl, cyclobutyl, cyclopentyl, cyclohexyl, cycloheptyl, tricyclodecyl, cyclododecyl, adamantyl, nornornyl, 5,6-trimethylenenorborn-2-yl and cyclooctyl. Such cycloaliphatic groups may optionally be substituted with one or more (e.g. 2, 3 or 4) substituents as defined hereinabove. Representative examples of cycloalkenyl include, but are not limited to, cyclopropenyl, cyclobutenyl, cyclopentenyl, cyclohexenyl, cycloheptenyl, cyclooctenyl, cyclononenyl, cyclodecenyl, 1,3-cyclohexadienyl, 1,4-cyclohexadienyl, 1,3-cycloheptadienyl, 1,5-cyclooctadienyl.

The term "heterocyclic", as used herein, refers to a saturated or ethylenically unsaturated but not aromatic monocyclic or polycyclic (e.g. bicyclic) ring system comprising at least one heteroatom preferably selected from the group consisting of nitrogen, oxygen and sulfur in at least one ring.

Monocyclic heterocyclic ring systems are exemplified by any 3 to 8 (e.g. 4, 5 or 6 or 7) member ring containing 1, 2, 3, or 4 heteroatoms independently selected from the group consisting of O, N, and S. A 5 member ring has from 0 to 2 double bonds, and a 6 member ring has from 0-3 double bonds. Depending upon the number of double bonds, the heterocyclic ring system may be heteroaromatic (see specific definition below) or not. Representative examples of monocyclic non-aromatic heterocyclic ring systems include, but are not limited to, azetidine, azepine, aziridine, diazepine, 1,3-dioxolane, 1,2-dioxane, 1,3-dioxane, 1,4-dioxane, 1,2-dithiane, 1,3-dithiane, 1,4-dithiane, imidazoline, imidazolidine, isothiazoline, isothiazolidine, isoxazoline, isoxazolidine, morpholine, oxadiazoline, oxadiazolidine, oxazoline, oxazolidine, piperazine, piperidine, pyrazine, pyrazoline, pyrazolidine, pyrroline, pyrrolidine, tetrahydrofuran, tetrahydrothiophene, thiadiazoline, thiadiazolidine, thiazoline, thiazolidine, thiomorpholine, thiomorpholine sulfone, thiomorpholine sulfoxide, and the like. Bicyclic ring systems are exemplified by any of the above monocyclic ring systems fused to an aryl or cycloalkyl or heterocyclic group as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aromatic" as used herein refers to a ring system having one or more aromatic rings, which may be homoaromatic or heteroaromatic.

"Homoaromatic" or "aryl" as used herein refers to an aromatic ring system in which no carbon atoms have been replaced with heteroatoms. The homoaromatic group can be unsubstituted or substituted with from 1 to 5 suitable substituents as defined hereinabove, and wherein two adjacent substituents may be linked to form a cycle such as methylenedioxy. Representative examples of aryl include, but are not limited to, azulenyl, indanyl, indenyl, naphthyl, phenyl, tetrahydronaphthyl, and mono- and polysubstituted versions thereof.

"Heteroaromatic" or "heteroaryl" as used herein refers to an aromatic ring system in which one or more carbon atoms have been replaced with heteroatoms independently selected from the group consisting of nitrogen, oxygen and sulfur in at least one ring. Examples of heteroaryl include, but are not limited to, pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl (in particular 1,2,3-triazolyl), pyridazinyl, indazolyl, purinyl, quinolizinyl, isoquinolyl, quinolyl, phthalazinyl, naphthyridinyl, quinoxalinyl, isothiazolyl, isoxazolyl, oxazolyl, dioxazolyl, pyrazolyl, tetrazinyl, tetrazolyl, thiadiazolyl, thiazolyl, triazinyl and benzo[b]thienyl. The heteroaryl group may be optionally substituted with one or more, e.g. 1 to 4, suitable substituents as defined hereinabove.

The term "$C_{1-20}$ alkoxy" as used herein refers to substituents wherein a carbon atom of a $C_{1-20}$ alkyl group (such as defined herein), is attached to an oxygen atom through a single bond such as, but not limited to, methoxy, ethoxy, propoxy, isopropoxy, butoxy, iso-butoxy, sec-butoxy, tert-butoxy, pentoxy, 3-pentoxy, or n-hexyloxy.

The term "$C_{1-20}$ alkylthio" as used herein refers to substituents wherein a carbon atom of a $C_{1-20}$ alkyl group (such as defined herein), is attached to an sulfur atom through a single bond such as, but not limited to, methylthio, ethylthio, etc.

The term "aryloxy" as used herein refers to substituents wherein a carbon atom of an aryl group (such as defined herein), is attached to an oxygen atom through a single bond such as, but not limited to, phenoxy, naphthoxy, etc.

The term "arylthio" as used herein refers to substituents wherein a carbon atom of an aryl group (such as defined herein), is attached to an sulfur atom through a single bond such as, but not limited to, phenylthio.

As used herein and unless otherwise stated, the term halogen means any atom selected from the group consisting of fluorine, chlorine, bromine and iodine.

The term "pharmaceutically acceptable salts" as used herein means the therapeutically active non-toxic salt forms which a compound of this invention is able to form, for example Na+, Li+, K+, Ca+2 and Mg+2 salts. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to, ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing Li+, Na+, and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds as well as their salts are able to form, such as for example hydrates, alcoholates and the like. Finally, it is to be understood that the compounds of the invention may be in their unionized, as well as zwitterionic form, and combinations with stoichiometric amounts of water as in hydrates.

Also included within the scope of this invention are the salts of the parental compounds with one or more amino acids as defined below, especially the naturally-occurring amino acids found as protein components. The amino acid may be one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and NX4+ (wherein X may be $C_{1-20}$ alkyl). Physiologically acceptable salts of an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as Na+ and NX4+ (wherein X typically is independently selected from H or a $C_{1-20}$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric forms (tautomers) and stereochemical forms (stereoisomers), which the compounds may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantionierically pure" and "diastereomerically pure" should be understood in a similar way, having regard to the enantiomeric excess, respectively the diastereomeric excess, of the relevant mixture.

Separation of stereoisomers may be accomplished by standard methods known to those skilled in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including:

(1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions.

Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, α-methoxy-α-(trifluoromethyl)phenyl acetate (Jacob III. in J. Org. Chem. (1982) 47: 4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthylisoquinolines (WO 96/15111).

Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. (see Chiral Liquid Chromatography (1989) W. J. Lough, Ed. Chapman and Hall, New York; and Okamoto in J. of Chromatogr. (1990) 513: 375-378).

The absolute stereochemical configuration of a compound of this invention may easily be determined by those skilled in the art while using well-known methods such as, for example, X-ray diffraction.

The term "amino acid" as used herein refers to any "natural amino acid" (Alanine (ala), Arginine (Arg), Asparagine (asn), Aspartic acid (Asp), Cysteine (cys), Glutamine (gin), Glutamic acid (glu), Glycine (gly), Histidine (his), Hydroxylysine (Hyl), Hydroxyproline (Hyp), Isoleucine (ile), Leucine (leu), Lysine (lys), Methionine (met), Phenylalanine (phe), Proline (pro), Serine (ser), Threonine (thr), Tryptophan (trp), Tyrosine (tyr), Valine (val)) in D or L conformation, as well as to "non-natural (or synthetic) amino acids" (e.g., but not limited to, phosphoserine, phosphothreonine, phosphotyrosin, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, tert-butylglycine, and amino-acids bearing sulfonic and/or phosphonic groups. This term also comprises natural and non-natural amino acids being protected at their carboxylic terminus, e.g. as a $C_{1-20}$ alkyl, phenyl or benzyl ester or as an amide, such as for example, a mono-$C_{1-20}$ alkyl or di-($C_{1-20}$ alkyl) amide, or another suitable carboxy-protecting group are known to those skilled in the art e.g. from T. W. Greene, Protecting Groups In Organic Synthesis, Wiley, New York, (1981) and references cited therein, the content of which is incorporated herein by reference).

The term "peptide" as used herein refers to a sequence of 2 to 100 amino-acids as defined hereinabove.

The term "microorganism", as used herein, refers to unicellular or cell-cluster microscopic organisms including eukaryotes such as fungi and protists, and prokaryotes, especially microorganisms that are susceptible to cause a disease in humans, but excluding a virus or a prion. These microorganisms can be organized in the form of a biofilm, thus the term "microbial biofilm".

The term "sepsis", as used herein, refers to a systemic inflammatory response syndrome associated to an infection. Septic shock is characterized namely by (a) hypotension persisting despite adequate fluid resuscitation, and (b) abnormalities related to hypoperfusion or organ dysfunction.

DETAILED DESCRIPTION OF THE INVENTION

The first aspect of the present invention will now be described with respect to a number of specific valuable embodiments.

One specific embodiment of this aspect of the present invention relates to a substituted 2-aminoimidazole compound wherein R3 is as defined in claim 2 of International application No. PCT/EP2010/070149 (which is hereby incorporated by reference), in combination with the aforementioned definitions of R1, R2 and R4.

Another specific embodiment of the present invention relates to a substituted 2-aminoimidazole compound being as defined in claim 2 of International application No. PCT/EP2010/070149 (which is hereby incorporated by reference), and wherein R1 is hydrogen, in combination with the aforementioned definitions of R2 and R4.

Another specific embodiment of the present invention relates to a substituted 2-aminoimidazole compound being as defined in claim 2 of International application No. PCT/EP2010/070149 (which is hereby incorporated by reference), and wherein R4 is hydrogen, in combination with the aforementioned definitions of R1 and R2.

Another specific embodiment of the present invention relates to a substituted 2-aminoimidazole compound being as defined in claim 2 of International application No. PCT/EP2010/070149 (which is hereby incorporated by reference), and wherein R1 and R4 are hydrogen, in combination with the aforementioned definition of R2.

Another specific embodiment of the present invention relates to a substituted 2-aminoimidazole compound wherein R2 is as defined in claim 3 of International application No. PCT/EP2010/070149 (which is hereby incorporated by reference), in combination with the aforementioned definitions of R1, R3 and R4.

Another specific embodiment of the present invention relates to a substituted 2-aminoimidazole compound being as defined in claim 3 of International application No. PCT/EP2010/070149 (which is hereby incorporated by reference), and wherein R1 is hydrogen, in combination with the aforementioned definitions of R3 and R4.

Another specific embodiment of the present invention relates to a substituted 2-aminoimidazole compound being as defined in claim 3 of International application No. PCT/EP2010/070149 (which is hereby incorporated by reference), and wherein R4 is hydrogen, in combination with the aforementioned definitions of R1 and R3.

Another specific embodiment of the present invention relates to a substituted 2-aminoimidazole compound being as defined in claim 3 of International application No. PCT/EP2010/070149 (which is hereby incorporated by reference), and wherein R1 and R4 are hydrogen, in combination with the aforementioned definition of R3.

Another specific embodiment of the present invention relates to a substituted 2-aminoimidazole compound wherein R4 is as defined in claim 4 of International application No. PCT/EP2010/070149 (which is hereby incorporated by reference), in combination with the aforementioned definitions of R1, R3 and R2.

Another specific embodiment of the present invention relates to a substituted 2-aminoimidazole compound being as defined in claim 4 of International application No. PCT/EP2010/070149 (which is hereby incorporated by reference), and wherein R1 is hydrogen, in combination with the aforementioned definitions of R2 and R3.

Another specific embodiment of the present invention relates to a substituted 2-aminoimidazole compound being represented by the structural formula (I), wherein each of R1, R3 and R4 is hydrogen, in combination with the aforementioned definition of R2.

Another specific embodiment of the present invention relates to a substituted 2-aminoimidazole compound being as defined in claim 2 of International application No. PCT/EP2010/070149 (which is hereby incorporated by reference), wherein R1 and R4 are hydrogen, and wherein R2 is as defined in claim 3 of International application No. PCT/EP2010/070149 (which is hereby incorporated by reference).

Another specific embodiment of the present invention relates to a substituted 2-aminoimidazole compound being as defined in claim 2 of International application No. PCT/EP2010/070149 (which is hereby incorporated by reference), wherein R1 is hydrogen, and wherein R4 is as defined in claim 4 of International application No. PCT/EP2010/070149 (which is hereby incorporated by reference).

Another specific embodiment of the present invention relates to a substituted 2-aminoimidazole compound being as defined in claim 5 of International application No. PCT/EP2010/070149 (which is hereby incorporated by reference).

Another specific embodiment of the present invention relates to a substituted 2-Amino-1H-imidazole/Triazole Conjugate according to the following structural formula (III)

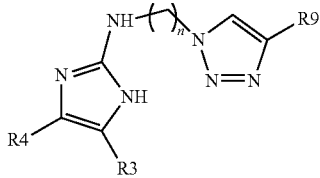

wherein R3, R4, and n are as defined hereinabove, and wherein R9 is selected from the group consisting of hydrogen, $C_{1-20}$ alkyl (e.g. propyl, n-butyl, tert-butyl, pentyl, hexyl or heptyl) optionally substituted e.g. with amino, $C_{1-20}$ alkoxy (e.g. pentoxy), $C_{2-20}$ alkenyl, $C_{2-20}$ alkynyl, $C_{3-12}$ cycloalkyl (e.g. cyclopropyl, cyclopentyl or cyclohexyl), $C_{3-12}$ cycloalkenyl, aryl (e.g. phenyl, naphthyl or substituted phenyl wherein the substituent(s) may be, but are not limited to, $C_{1-4}$ alkyl or $C_{1-4}$ alkoxy), methylamino, heterocyclic and heteroaryl (e.g. thiofuryl).

Another specific embodiment of the present invention relates to an imidazo[1,2-a]pyrimidinium salt being represented by the structural formula (II) as defined in claim 1 of International application No. PCT/EP2010/070149 (which is hereby incorporated by reference), and wherein $X^-$ is an inorganic or organic anion, in combination with the aforementioned definitions of R1, R2, R3, R4, R5, R6, R7 and R8.

Another specific embodiment of the present invention relates to an imidazo[1,2-a]pyrimidinium salt being as defined in claim 6 of International application No. PCT/EP2010/070149 (which is hereby incorporated by reference), in combination with the aforementioned definitions of R1, R2, R3, R4, R5, R6, R7 and R8.

Another specific embodiment of the present invention relates to an imidazo[1,2-a]pyrimidinium salt being as defined in claim 6 of International application No. PCT/EP2010/070149 (which is hereby incorporated by reference), and wherein each of R6, R7 and R8 is hydrogen, in combination with the aforementioned definitions of R1, R2, R3, R4 and R5.

Another specific embodiment of the present invention relates to an imidazo[1,2-a]pyrimidinium salt wherein R1 is as defined in claim 7 of International application No. PCT/EP2010/070149 (which is hereby incorporated by reference), in combination with the aforementioned definitions of $X^-$, R2, R3, R4, R5, R6, R7 and R8.

Another specific embodiment of the present invention relates to an imidazo[1,2-a]pyrimidinium salt being as defined in claim 7 of International application No. PCT/EP2010/070149 (which is hereby incorporated by reference), and wherein each of R6, R7 and R8 is hydrogen, in combination with the aforementioned definitions of $X^-$, R2, R3, R4 and R5.

Another specific embodiment of the present invention relates to an imidazo[1,2-a]pyrimidinium salt wherein R3 is as defined in claim 8 of International application No. PCT/EP2010/070149 (which is hereby incorporated by reference), in combination with the aforementioned definitions of $X^-$, R1, R2, R4, R5, R6, R7 and R8.

Another specific embodiment of the present invention relates to an imidazo[1,2-a]pyrimidinium salt being as defined in claim 8 of International application No. PCT/EP2010/070149 (which is hereby incorporated by reference), and wherein each of R6, R7 and R8 is hydrogen in combination with the aforementioned definitions of $X^-$, R1, R2, R4 and R5.

Another specific embodiment of the present invention relates to an imidazo[1,2-a]pyrimidinium salt being represented by the structural formula (II), wherein R4 is selected from the group consisting of hydrogen, methyl, benzyl, 4-methoxybenzyl, phenyl and 4-tolyl, in combination with the aforementioned definitions of $X^-$, R1, R2, R3, R5, R6, R7 and R8.

Another specific embodiment of the present invention relates to an imidazo[1,2-a]pyrimidinium salt being represented by the structural formula (II), wherein R4 is selected from the group consisting of hydrogen, methyl, benzyl, 4-methoxybenzyl, phenyl and 4-tolyl, and wherein each of R6, R7 and R8 is hydrogen, in combination with the aforementioned definitions of $X^-$, R1, R2, R3 and R5.

Another specific embodiment of the present invention relates to an imidazo[1,2-a]pyrimidinium salt being selected from the group consisting of 1-isopropyl-2-hydroxy-2-(4-methylphenyl)-2,3-dihydro-1H-imidazo[1,2-a]pyrimidin-4-ium bromide, 1-cyclo-propyl-2-hydroxy-2-(4-chlorophenyl)-2,3-dihydro-1H-imidazo[1,2-a]pyrimidin-4-ium bromide, 1-cyclopropyl-2-hydroxy-2-(4-bromophenyl)-2,3-dihydro-1H-imidazo[1,2-a]-pyrimidin-4-ium bromide, 1-butyl-2-hydroxy-2-(4-bromophenyl)-2,3-dihydro-1H-imidazo[1,2-a]pyrimidin-4-ium bromide, 1-butyl-2-hydroxy-2-(4-fluorophenyl)-2,3-dihydro-1H-imidazo[1,2-a]pyrimidin-4-ium bromide, 1-butyl-2-hydroxy-2-(diphenyl-methyl)-2,3-dihydro-1H-imidazo[1,2-a]pyrimidin-4-ium bromide, 1-cyclopentyl-2-hydroxy-2-(4-biphenylyl)-2,3-dihydro-1H-imidazo[1,2-a]pyrimidin-4-ium bromide, 1-hexyl-2-hydroxy-2-phenyl-3-methyl-2,3-dihydro-1H-imidazo[1,2-a]pyrimidin-4-ium bromide, 1-hexyl-2-hydroxy-2-(4-nitrophenyl)-2,3-dihydro-1H-imidazo[1,2-a]pyrimidin-4-ium bromide, 1-cyclohexyl-2-hydroxy-2-(4-chlorophenyl)-2,3-dihydro-1H-imidazo-[1,2-a]pyrimidin-4-ium bromide, 1-cyclohexyl-2-hydroxy-2-(4-methylthiophenyl)-2,3-dihydro-1H-imidazo[1,2-a]pyrimidin-4-ium bromide, 1-cyclohexyl-2-hydroxy-2-(4-cyanophenyl)-2,3-dihydro-1H-imidazo[1,2-a]pyrimidin-4-ium bromide, 1-cyclohexyl-2-hydroxy-2-(4-methoxyphenyl)-2,3-dihydro-1H-imidazo[1,2-a]pyrimidin-4-ium bromide, 1-cyclohexyl-2-hydroxy-2-(4-chlorophenyl)-2,3-dihydro-1H-imidazo[1,2-a]pyrimidin-4-ium bromide, 1-phenyl-2-hydroxy-2-(4-bromophenyl)-3-methyl-2,3-dihydro-1H-imidazo[1,2-a]pyrimidin-4-ium bromide, 1-benzyl-2-hydroxy-2-(4-iodophenyl)-2,3-dihydro-1H-imidazo[1,2-a]pyrimidin-4-ium bromide, 1-benzyl-2-hydroxy-2-(4-nitrophenyl)-2,3-dihydro-1H-imidazo[1,2-a]pyrimidin-4-ium bromide, 1-benzyl-2-hydroxy-2-

(phenyl)-2,3-dihydro-1H-imidazo[1,2-a]pyrimidin-4-ium bromide, 1-(2-(3-methoxyphenyl)ethyl)-2-hydroxy-2-(3,4-dichlorophenyl)-2,3-dihydro-1H-imidazo[1,2-a]-pyrimidin-4-ium bromide, 1-(2-(3-methoxyphenyl)ethyl)-2-hydroxy-2-(4-biphenylyl)-2,3-dihydro-1H-imidazo[1,2a]pyrimidin-4-ium bromide, 1-(2-(3-methoxyphenyl)ethyl)-2-hydroxy-2-(4-nitrophenyl)-2,3-dihydro-1H-imidazo[1,2-a]pyrimidin-4-ium bromide, 1-(2-(3,4-dimethoxyphenyl)ethyl)-2-hydroxy-2-(4-nitrophenyl)-2,3-dihydro-1H-imidazo-[1,2-a]pyrimidin-4-ium bromide, 1-(4-methoxybenzyl)-2-hydroxy-2-(4-nitrophenyl)-2,3-dihydro-1H-imidazo[1,2-a]pyrimidin-4-ium bromide, 1-(4-methoxybenzyl)-2-hydroxy-2-(4-bromophenyl)-2,3-dihydro-1H-imidazo[1,2-a]pyrimidin-4-ium bromide, 1-piperonyl-2-hydroxy-2-(4-fluorophenyl)-2,3-dihydro-1H-imidazo[1,2-a]pyrimidin-4-ium bromide, 1-piperonyl-2-hydroxy-2-(3,4-methylenedioxyphenyl)-2,3-dihydro-1H-imidazo[1,2-a]-pyrimidin-4-ium bromide, 1-cyclododecyl-2-hydroxy-2-(3-nitrophenyl)-2,3-dihydro-1H-imidazo[1,2-a]pyrimidin-4-ium bromide, 1-cyclododecyl-2-hydroxy-2-(4-nitrophenyl)-2,3-dihydro-1H-imidazo[1,2-a]pyrimidin-4-ium bromide, and 1-(tricyclo[3.3.1.13,7]dec-1-yl)-2-hydroxy-2-(4-nitrophenyl)-2,3-dihydro-1H-imidazo[1,2-a]pyrimidin-4-ium bromide.

Another specific embodiment of the present invention relates to an imidazo[1,2-a]pyrimidinium salt being selected from the group consisting of 1-hexyl-2-hydroxy-2-phenyl-2,3-dihydro-1H-imidazo[1,2-a]pyrimidin-4-ium bromide, 1-heptyl-2-hydroxy-2-phenyl-2,3-dihydro-1H-imidazo[1,2-a]pyrimidin-4-ium bromide, 1-octyl-2-hydroxy-2-phenyl-2,3-dihydro-1H-imidazo[1,2-a]pyrimidin-4-ium bromide, 1-nonyl-2-hydroxy-2-phenyl-2,3-dihydro-1H-imidazo[1,2-a]pyrimidin-4-ium bromide, 1-decyl-2-hydroxy-2-phenyl-2,3-dihydro-1H-imidazo[1,2-a]pyrimidin-4-ium bromide, 1-undecyl-2-hydroxy-2-phenyl-2,3-dihydro-1H-imidazo[1,2-a]pyrimidin-4-ium bromide, 1-dodecyl-2-hydroxy-2-phenyl-2,3-dihydro-1H-imidazo[1,2-a]pyrimidin-4-ium bromide, 1-tridecyl-2-hydroxy-2-phenyl-2,3-dihydro-1H-imidazo[1,2-a]pyrimidin-4-ium bromide, 1-tetradecyl-2-hydroxy-2-phenyl-2,3-dihydro-1H-imidazo[1,2-a]pyrimidin-4-ium bromide, 1-cycloheptyl-2-hydroxy-2-phenyl-2,3-dihydro-1H-imidazo[1,2-a]pyrimidin-4-ium bromide, 1-cyclooctyl-2-hydroxy-2-phenyl-2,3-dihydro-1H-imidazo[1,2-a]pyrimidin-4-ium bromide, 1-hexyl-2-hydroxy-2-(4-chlorophenyl)-2,3-dihydro-1H-imidazo[1,2-a]pyrimidin-4-ium bromide, 1-heptyl-2-hydroxy-2-(4-chlorophenyl)-2,3-dihydro-1H-imidazo[1,2-a]pyrimidin-4-ium bromide, 1-octyl-2-hydroxy-2-(4-chlorophenyl)-2,3-dihydro-1H-imidazo[1,2-a]-pyrimidin-4-ium bromide, 1-nonyl-2-hydroxy-2-(4-chlorophenyl)-2,3-dihydro-1H-imidazo[1,2-a]pyrimidin-4-ium bromide, 1-decyl-2-hydroxy-2-(4-chlorophenyl)-2,3-dihydro-1H-imidazo[1,2-a]pyrimidin-4-ium bromide, 1-undecyl-2-hydroxy-2-(4-chloro-phenyl)-2,3-dihydro-1H-imidazo[1,2-a]pyrimidin-4-ium bromide, 1-dodecyl-2-hydroxy-2-(4-chlorophenyl)-2,3-dihydro-1H-imidazo[1,2-a]pyrimidin-4-ium bromide, 1-tridecyl-2-hydroxy-2-(4-chlorophenyl)-2,3-dihydro-1H-imidazo[1,2-a]pyrimidin-4-ium bromide, 1-tetradecyl-2-hydroxy-2-(4-chlorophenyl)-2,3-dihydro-1H-imidazo[1,2-a]pyrimidin-4-ium bromide, 1-cycloheptyl-2-hydroxy-2-(4-chlorophenyl)-2,3-dihydro-1H-imidazo[1,2-a]pyrimidin-4-ium bromide, 1-cyclooctyl-2-hydroxy-2-(4-chlorophenyl)-2,3-dihydro-1H-imidazo[1,2-a]pyrimidin-4-ium bromide, 1-hexyl-2-hydroxy-2-(4-nitrophenyl)-2,3-dihydro-1H-imidazo[1,2-a]pyrimidin-4-ium bromide, 1-octyl-2-hydroxy-2-(4-nitro-phenyl)-2,3-dihydro-1H-imidazo[1,2-a]pyrimidin-4-ium bromide, 1-decyl-2-hydroxy-2-(4-nitrophenyl)-2,3-dihydro-1H-imidazo[1,2-a]pyrimidin-4-ium bromide, 1-octyl-2-hydroxy-2-(4-fluorophenyl)-2,3-dihydro-1H-imidazo[1,2-a]pyrimidin-4-ium bromide, 1-decyl-2-hydroxy-2-(4-fluorophenyl)-2,3-dihydro-1H-imidazo[1,2-a]pyrimidin-4-ium bromide, 1-octyl-2-hydroxy-2-(3,4-dichlorophenyl)-2,3-dihydro-1H-imidazo[1,2-a]pyrimidin-4-ium bromide, 1-decyl-2-hydroxy-2-(3,4-dichlorophenyl)-2,3-dihydro-1H-imidazo[1,2-a]pyrimidin-4-ium bromide, 1-octyl-2-hydroxy-2-(4-methoxyphenyl)-2,3-dihydro-1H-imidazo[1,2-a]pyrimidin-4-ium bromide, 1-decyl-2-hydroxy-2-(4-methoxyhenyl)-2,3-dihydro-1H-imidazo[1,2-a]pyrimidin-4-ium bromide, 1-octyl-2-hydroxy-2-(4-methylthiophenyl)-2,3-dihydro-1H-imidazo[1,2-a]pyrimidin-4-ium bromide, 1-decyl-2-hydroxy-2-(4-methylthiophenyl)-2,3-dihydro-1H-imidazo[1,2-a]-pyrimidin-4-ium bromide, 1-octyl-2-hydroxy-2-(1-naphthalenyl)-2,3-dihydro-1H-imidazo[1,2-a]pyrimidin-4-ium bromide, 1-decyl-2-hydroxy-2-(1-naphthalenyl)-2,3-dihydro-1H-imidazo[1,2-a]pyrimidin-4-ium bromide, 1-octyl-2-hydroxy-2-(4-methylsulfonylphenyl)-2,3-dihydro-1H-imidazo[1,2-a]pyrimidin-4-ium bromide, 1-decyl-2-hydroxy-2-(4-methylsulfonylphenyl)-2,3-dihydro-1H-imidazo[1,2-a]pyrimidin-4-ium bromide, 1-octyl-2-hydroxy-2-(4'-nitro[1,1'-biphenylyl]-4-yl)-2,3-dihydro-1H-imidazo[1,2-a]pyrimidin-4-ium bromide, 1-decyl-2-hydroxy-2-(4'-nitro[1,1'-biphenylyl]-4-yl)-2,3-dihydro-1H-imidazo[1,2-a]pyrimidin-4-ium bromide, 1-octyl-2-hydroxy-2-(3-bromophenyl)-2,3-dihydro-1H-imidazo[1,2-a]pyrimidin-4-ium bromide, 1-decyl-2-hydroxy-2-(3-bromophenyl)-2,3-dihydro-1H-imidazo[1,2-a]pyrimidin-4-ium bromide, 1-octyl-2-hydroxy-2-([1,1':4',1"-terphenyl]-4-yl)-2,3-dihydro-1H-imidazo[1,2-a]pyrimidin-4-ium bromide, 1-octyl-2-(4-methoxyphenyl)-imidazo[1,2-a]pyrimidin-1-ium perchlorate, 1-octyl-2-(4-fluorophenyl)-imidazo[1,2-a]pyrimidin-1-ium perchlorate, 1-octyl-2-(3,4-dichlorophenyl)-imidazo[1,2-a]pyrimidin-1-ium perchlorate, 1-octyl-2-(3-bromophenyl)-imidazo[1,2-a]pyrimidin-1-ium perchlorate, 1-octyl-2-(1-naphthalenyl)-imidazo[1,2-a]-pyrimidin-1-ium perchlorate, 1-octyl-2-(4-nitrophenyl)-imidazo[1,2-a]pyrimidin-1-ium perchlorate, 1-octyl-2-(4'-nitro[1,1-biphenylyl]-4-yl)-imidazo[1,2-a]pyrimidin-1-ium perchlorate, 1-octyl-2-(4-methylsulfonylphenyl)-imidazo[1,2-a]pyrimidin-1-ium perchlorate, 1-octyl-2-(4-methylthiophenyl)-imidazo[1,2-a]pyrimidin-1-ium perchlorate, 1-octyl-2-([1,1':4',1"-terphenyl]-4-yl)-imidazo[1,2-a]pyrimidin-1-ium perchlorate, 1-decyl-2-(4"-nitro ([1,1':4',1"-terphenyl]-4-yl)-imidazo[1,2-a]pyrimidin-1-ium perchlorate.

Another specific embodiment of the present invention relates to an imidazo[1,2-a]pyrimidinium salt being selected from the group consisting of 1-methyl-2-hydroxy-2-phenyl-2,3-dihydro-1H-imidazo[1,2-a]pyrimidin-4-ium bromide, 1-methyl-2-hydroxy-2-(4-chlorophenyl)-2,3-dihydro-1H-imidazo[1,2-a]pyrimidin-4-ium bromide, 1-methyl-2-hydroxy-2-(4-fluorophenyl)-2,3-dihydro-1H-imidazo[1,2-a]pyrimidin-4-ium bromide, 1-methyl-2-hydroxy-2-(3-fluorophenyl)-2,3-dihydro-1H-imidazo[1,2-a]pyrimidin-4-ium bromide, 1-(3,4-methylenedioxyphenylmethyl)-2-hydroxy-2-(4-fluorophenyl)-2,3-dihydro-1H-imidazo[1,2-a]pyrimidin-4-ium bromide, 1-(3,4-methylenedioxyphenylmethyl)-2-hydroxy-2-(3,4-methylendioxyphenyl)-2,3-dihydro-1H-imidazo[1,2-a]-pyrimidin-4-ium bromide, 1-ethyl-2-hydroxy-2-(4-nitrophenyl)-2,3-dihydro-1H-imidazo-[1,2-a]pyrimidin-4-ium bromide, 1-(3-methoxyphenyl)ethyl)-2-hydroxy-2-(4-fluoro-phenyl)-2,3-dihydro-1H-imidazo[1,2-a]pyrimidin-4-ium bromide, 1-isopropyl-2-hydroxy-2-phenyl-2,3-dihydro-1H-imidazo[1,2-a]

pyrimidin-4-ium bromide, 1-isopropyl-2-hydroxy-2-(4-nitrophenyl)-2,3-dihydro-1H-imidazo[1,2-a]pyrimidin-4-ium bromide, 1-butyl-2-hydroxy-2-phenyl-2,3-dihydro-1H-imidazo[1,2-a]pyrimidin-4-ium bromide, 1-butyl-2-hydroxy-2-(4-chlorophenyl)-2,3-dihydro-1H-imidazo[1,2-a]pyrimidin-4-ium bromide, 1-butyl-2-hydroxy-2-(4-nitrophenyl)-2,3-dihydro-1H-imidazo[1,2-a]pyrimidin-4-ium bromide, 1-butyl-2-hydroxy-2-(4-methoxyphenyl)-2,3-dihydro-1H-imidazo[1,2-a]pyrimidin-4-ium bromide, 1-isobutyl-2-hydroxy-2-phenyl-2,3-dihydro-1H-imidazo[1,2-a]pyrimidin-4-ium bromide, 1-isobutyl-2-hydroxy-2-(4-chlorophenyl)-2,3-dihydro-1H-imidazo[1,2-a]pyrimidin-4-ium bromide, 1-isobutyl-2-hydroxy-2-(3-bromophenyl)-2,3-dihydro-1H-imidazo[1,2-a]pyrimidin-4-ium bromide, 1-isobutyl-2-hydroxy-2-(4-nitrophenyl)-2,3-dihydro-1H-imidazo[1,2-a]pyrimidin-4-ium bromide, 1-isobutyl-2-hydroxy-2-(3,4-dichlorophenyl)-2,3-dihydro-1H-imidazo[1,2-a]pyrimidin-4-ium bromide, 1-tert-butyl-2-hydroxy-2-(4-nitrophenyl)-2,3-dihydro-1H-imidazo[1,2-a]-pyrimidin-4-ium bromide, 1-pentyl-2-hydroxy-2-phenyl-2,3-dihydro-1H-imidazo[1,2-a]pyrimidin-4-ium bromide, 1-pentyl-2-hydroxy-2-(4-chlorophenyl)-2,3-dihydro-1H-imidazo[1,2-a]pyrimidin-4-ium bromide, 1-pentyl-2-hydroxy-2-(4-bromophenyl)-2,3-dihydro-1H-imidazo[1,2-a]pyrimidin-4-ium bromide, 1-decyl-2-hydroxy-2-(4-methoxy-phenyl)-2,3-dihydro-1H-imidazo[1,2-a]pyrimidin-4-ium bromide, 1-decyl-2-hydroxy-2-(3,4-dichlorophenyl)-2,3-dihydro-1H-imidazo[1,2-a]pyrimidin-4-ium bromide, 1-tetradecyl-2-hydroxy-2-(4-chlorophenyl)-2,3-dihydro-1H-imidazo[1,2-a]pyrimidin-4-ium bromide, 1-cyclopropyl-2-hydroxy-2-(4-nitrophenyl)-2,3-dihydro-1H-imidazo[1,2-a]-pyrimidin-4-ium bromide, 1-cyclobutyl-2-hydroxy-2-phenyl-2,3-dihydro-1H-imidazo[1,2-a]pyrimidin-4-ium bromide, 1-cyclohexyl-2-hydroxy-2-phenyl-2,3-dihydro-1H-imidazo[1,2-a]pyrimidin-4-ium bromide, and 1-adamantyl-2-hydroxy-2-(4-nitrophenyl)-2,3-dihydro-1H-imidazo[1,2-a]pyrimidin-4-ium bromide.

Another specific embodiment of the present invention relates to an imidazo[1,2-a]pyrimidinium salt being selected from the group consisting of 1-(3-Azidopropyl)-2-hydroxy-2-phenyl-2,3-dihydro-1H-imidazo[1,2-a]pyrimidin-4-ium bromide, 1-(2-Azidoethyl)-2-(4-bromophenyl)-2-hydroxy-2,3-dihydro-1H-imidazo[1,2-a]pyrimidin-4-ium bromide, 1-(2-Azidoethyl)-2-hydroxy-2-phenyl-2,3-dihydro-1H-imidazo[1,2-a]pyrimidin-4-ium bromide, 1-(2-Azidoethyl)-2-hydroxy-2-(naphth-1-yl)-2,3-dihydro-1H-imidazo[1,2-a]pyrimidin-4-ium bromide, 1-(3-Azidopropyl)-2-(4-bromophenyl)-2-hydroxy-2,3-dihydro-1H-imidazo[1,2-a]pyrimidin-4-ium bromide, 1-(2-Azidoethyl)-2-(3,4-dichlorophenyl)-2-hydroxy-2,3-dihydro-1H-imidazo[1,2-a]pyrimidin-4-ium bromide, 1-(3-Azidopropyl)-2-(3,4-dichlorophenyl)-2-hydroxy-2,3-dihydro-1H-imidazo[1,2-a]pyrimidin-4-ium bromide, 1-(3-Azidopropyl)-2-hydroxy-2-(morpholine-4-carbonyl)-2,3-dihydro-1H-imidazo[1,2-a]pyrimidin-4-ium bromide, 1-(2-Azidoethyl)-2-hydroxy-2-(morpholine-4-carbonyl)-2,3-dihydro-1H-imidazo[1,2-a]pyrimidin-4-ium bromide, 1-(2-Azidoethyl)-2-(4-fluorophenyl)-2-hydroxy-2,3-dihydro-1H-imidazo[1,2-a]pyrimidin-4-ium bromide, 1-(2-Azidoethyl)-2-(4-chlorophenyl)-2-hydroxy-3-p-tolyl-2,3-dihydro-1H-imidazo[1,2-a]pyrimidin-4-ium bromide, and 1-(3-Azidopropyl)-2-hydroxy-2,3-diphenyl-2,3-dihydro-1H-imidazo[1,2-a]pyrimidin-4-ium bromide.

Another specific embodiment of the present invention relates to an imidazo[1,2-a]pyrimidinium salt being selected from the group consisting of 1-(4-Azidobutyl)-2-hydroxy-2-phenyl-2,3-dihydro-1H-imidazo[1,2-a]pyrimidin-4-ium bromide, 1-(4-Azidobutyl)-2-(4-bromophenyl)-2-hydroxy-2,3-dihydro-1H-imidazo[1,2-a]pyrimidin-4-ium bromide, 1-(4-Azidobutyl)-2-hydroxy-2-(naphth-1-yl)-2,3-dihydro-1H-imidazo[1,2-a]pyrimidin-4-ium bromide, 1-(4-Azidobutyl)-2-(3,4-dichlorophenyl)-2-hydroxy-2,3-dihydro-1H-imidazo[1,2-a]pyrimidin-4-ium bromide, 1-(4-Azidobutyl)-2-hydroxy-2-(morpholine-4-carbonyl)-2,3-dihydro-1H-imidazo[1,2-a]pyrimidin-4-ium bromide, 1-(4-Azidobutyl)-2-(4-fluorophenyl)-2-hydroxy-2,3-dihydro-1H-imidazo[1,2-a]pyrimidin-4-ium bromide, 1-(4-Azidobutyl)-2-(4-chlorophenyl)-2-hydroxy-3-p-tolyl-2,3-dihydro-1H-imidazo[1,2-a]pyrimidin-4-ium bromide, 1-(2-Azidoethyl)-2-hydroxy-2,3-diphenyl-2,3-dihydro-1H-imidazo[1,2-a]pyrimidin-4-ium bromide, 1-(3-Azidopropyl)-2-hydroxy-2-(naphth-1-yl)-2,3-dihydro-1H-imidazo[1,2-a]pyrimidin-4-ium bromide, and 1-(4-Azidobutyl)-2-hydroxy-2,3-diphenyl-2,3-dihydro-1H-imidazo[1,2-a]pyrimidin-4-ium bromide.

The present invention also relates to methods of making the novel compounds described herein, and precursors thereof. These compounds may be prepared by any of the applicable techniques of organic synthesis well known in the art, such as elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., "Advanced Organic Chemistry, Third Edition", and in "Comprehensive Organic Synthesis. Selectivity, Strategy & Efficiency in Modern Organic Chemistry in 9 Volumes", Barry M. Trost, Editor-in-Chief (Pergamon Press, New York, 1993).

Exemplary methods for preparing the compounds of the invention, and precursors thereof, are provided below. These methods are intended to illustrate the nature of such preparation, and are not intended to limit the scope of applicable methods. Generally, the reaction conditions such as temperature, reaction time, solvents, workup procedures, and the like, will be those common in the art for the particular reaction to be performed. Typically temperatures will be from about −80° C. to 200° C., solvents will be aprotic or protic, and reaction times will be from about 10 seconds to 40 hours. Workup typically consists of quenching any unreacted reagents followed by partition between a water/organic layer system (extraction) and separating the layer containing the product.

All the novel compounds of the first aspect of the present invention as defined in claim 1 of International application No. PCT/EP2010/070149 (which is hereby incorporated by reference), can be produced in good yield according to a synthetic procedure comprising an initial step of forming a substituted imidazo[1,2-a]pyrimidinium salt being represented by the structural formula (II) wherein ring A is an imidazolinyl structure represented by formula B, and wherein X⁻ is the bromine anion, with the aforementioned definitions of R1, R2, R3, R4, R5, R6, R7 and R8, including all specific meanings for each substituent. This initial step proceeds as shown in tables 1, 3 and 4 of *J. Org. Chem.* (2008) 73:6691-6697 and in the left part of the synthetic scheme of the examples below, i.e. by reacting a 2-aminopyrimidine wherein the amino group is mono-substituted with R1, and wherein the pyrimidinyl ring is optionally substituted with one, two or three substituents R6, R7 and R8, with an α-bromocarbonyl compound represented by the structural formula $R_4$CHBr—CO—$R_3$ wherein R4 and R3 are as defined in claim 1 of International application No. PCT/EP2010/070149 (which is hereby incorporated by reference).

2-aminopyrimidines wherein the amino group is monosubstituted with R1, wherein R1 is $C_{1-20}$ alkyl substituted with one terminal azido group are not known in the art. They may be produced, according to the present invention, by reacting an azidoalkylamine (wherein alkyl has 1 to 20 carbon atoms) with a 2-halopyrimidine, preferably 2-chloropyrimidine. In this way have been produced N-(1-azidomethyl)pyrimidin-2-amine, N-(2-azidoethyl)pyrimidin-2-amine, N-(3-azidopropyl)pyrimidin-2-amine, N-(4-azidobutyl)pyrimidin-2-amine, N-(5-azidopentyl)pyrimidin-2-amine, N-(6-azidohexyl)pyrimidin-2-amine, N-(7-azidoheptyl)pyrimidin-2-amine, N-(8-azidooctyl)pyrimidin-2-amine, N-(9-azidononyl)pyrimidin-2-amine, N-(10-azidodecyl)pyrimidin-2-amine, N-(11-azidoundecyl)pyrimidin-2-amine, N-(12-azidododecyl)pyrimidin-2-amine, N-(13-azidotridecyl)pyrimidin-2-amine, N-(14-azidotetradecyl)pyrimidin-2-amine, N-(15-azidopentadecyl)pyrimidin-2-amine, N-(16-azidohexadecyl)pyrimidin-2-amine, N-(17-azidoheptadecyl)pyrimidin-2-amine, N-(18-azidooctadecyl)pyrimidin-2-amine and N-(19-azidononadecyl)pyrimidin-2-amine.

When R3 is hydrogen, said α-bromocarbonyl compound is a α-bromoaldehyde such as, but not limited to, 2-bromoacetaldehyde. When R3 is not hydrogen, said α-bromocarbonyl compound is an α-bromoketone. When R3 is not hydrogen and R4 is not hydrogen, said α-bromocarbonyl compound is a 1,2-disubstituted bromoketone. When R3 is aryl and R4 is hydrogen, said α-bromocarbonyl compound is an optionally substituted α-bromoacetophenone. Suitable optionally substituted 2-bromoacetophenones for this reaction (thus providing the R3 substituent in the substituted imidazo[1,2-a]pyrimidinium salt) include, but are not limited to, commercial products such as bromo-acetophenone, 2,3'-dibromoacetophenone, 2-bromo-4'-fluoroacetophenone, 2-bromo-4'-chloro-acetophenone, 2-bromo-4'-nitroacetophenone, 2-bromo-4'-cyanoacetophenone, 2-bromo-4'-(trifluoromethyl)acetophenone, 2-bromo-4'-methoxyacetophenone, 2-bromo-3'-methoxyacetophenone, 2-bromo-2'-methoxyacetophenone, bromomethyl 2-naphthylketone, 2-bromo-4'-methylacetophenone, 2-bromo-4'-hydroxyacetophenone, 2-bromo-3'-methylacetophenone, 2-bromo-2'-methylacetophenone, 2-bromo-4'-ethyl-acetophenone, 2-bromo-4'-propylacetophenone, 2-bromo-4'-isopropylacetophenone, 2-bromo-4'-n-butylacetophenone, 2-bromo-4'-(methylthio)acetophenone, 2-bromo-2',5'-dimethoxyacetophenone, 2-bromo-3',4',5'-trimethoxyacetophenone and 2-bromo-4'-phenylacetophenone. If a desirable substituted 2-bromoacetophenone is not commercially available, it can easily be prepared by bromination of the correspondingly substituted acetophenone while using techniques well known in the art.

This initial step of the synthetic procedure proceeds readily in an apolar solvent such as, but not limited to, acetonitrile, and under temperature conditions ranging from about 70° C. to about 150° C. during 0.5 to about 8 hours.

If desirable to achieve a substituted imidazo[1,2-a]pyrimidinium salt being represented by the structural formula (II) wherein ring A is an imidazolinyl structure represented by formula B, and wherein X⁻ is an organic or inorganic anion other than the bromine anion, the bromide salt formed in the initial step may be submitted to a classical anion exchange reaction with shifting equilibrium towards the less soluble salt. In this way bromine may be replaced with the anion derived from hydrochloric acid, hydroiodic acid, sulfuric acid, nitric acid, phosphoric acid, and organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid.

If desirable to achieve a substituted imidazo[1,2-a]pyrimidinium salt being represented by the structural formula (II) wherein ring A is an imidazolyl structure represented by formula C, the bromide salt formed in the initial step may be submitted to dehydration by any suitable means such as, but not limited to, short heating in polyphosphoric acid and addition of an inorganic acid such as perchloric acid, as also shown in *J. Org. Chem.* (2008) 73:6691-6697. Such substituted imidazo[1,2-a]pyrimidinium salt being represented by the structural formula (II) wherein ring A is an imidazolyl structure represented by formula (C) are useful intermediates for making unsubstituted 2-aminoimidazole compounds as for instance disclosed in WO 2009/1223753, but they also are active for inhibiting biofilm formation as disclosed herein.

Novel substituted 2-aminoimidazole compounds represented by the structural formula (I) may then be produced in a second step by reacting the substituted imidazo[1,2-a]pyrimidinium salt being represented by the structural formula (II) wherein ring A is an imidazolinyl structure represented by formula B and wherein X⁻ is the bromine anion, which is the result of the initial step, with a molar excess of hydrazine for a short period of time at a temperature range from about 70° C. to about 100° C., as shown in table 4 and scheme 3 of *J. Org. Chem.* (2008) 73:6691-6697. No interconversion occurs between the formed 1-unsubstituted 2-(substituted amino) imidazole compounds and their 1-substituted 2-aminoimidazole isomers. However the signals of C-4 and C-5 of the imidazole ring of the formed 1-unsubstituted 2-(substituted amino)imidazole compounds usually appear as broad peaks or are even not detected, presumably to a fast proton exchange between N-1 and N-3.

Substituted 2-aminoimidazole compounds represented by the structural formula (III) can be obtained by reacting an imidazo[1,2-a]pyrimidinium salt represented by the structural formula (II) wherein R4 and R5 are each independently selected from the group consisting of $C_{1-20}$ alkyl, $C_{2-20}$ alkenyl, $C_{2-20}$ alkynyl, $C_{3-12}$ cycloalkyl and $C_{3-12}$ cycloalkenyl, and wherein R1 is $C_{1-20}$ alkyl substituted with one terminal azido group, with an optionally substituted acetylene represented by the structural formula HCCR9, wherein R9 is selected from the group consisting of hydrogen, $C_{1-20}$ alkyl optionally substituted with amino, halogen or dimethylamino, $C_{1-20}$ alkoxy, $C_{2-20}$ alkenyl, $C_{2-20}$ alkynyl, $C_{3-12}$ cycloalkyl, $C_{3-12}$ cycloalkenyl, aryl optionally substituted with one or more substituent(s) independently selected from the group consisting of $C_{1-4}$ alkyl and $C_{1-4}$ alkoxy, methylamino, heterocyclic and heteroaryl. Suitable substituted acetylenes for this purpose include, but are not limited to, phenylacetylene, propyne, propargyl bromide, propargyl chloride, propargylamine, butyne, and analogs thereof.

Compounds according to the first aspect of the present invention as defined in claim 1 of International application No. PCT/EP2010/070149 (which is hereby incorporated by reference), are able to form hydrates with water, or solvates with an organic solvent such as, but not limited to, a nitrile (e.g. acetonitrile), an ester (e.g. ethyl acetate), an alcohol (e.g. methanol, ethanol or isopropanol) or an ether (e.g. diethyl ether), using solvation methods well known in the art. The skilled person is able to readily determine the feasibility of a certain solvate without an undue burden of experimentation. When an assymetric carbon present, all possible stereoisomers or enantiomers are encompassed by the present invention.

The second aspect of the present invention as defined in claim 9 of International application No. PCT/EP2010/

070149 (which is hereby incorporated by reference), will now be described with respect to a number of specific valuable embodiments.

For instance it has been demonstrated that 2-(substituted amino)imidazole compounds according the structural formula (B) wherein R1, R2, R3 and R4 are as defined in table 1 (wherein Ph stands for phenyl, Me for methyl, etc.) below are capable of inhibiting biofilm formation.

TABLE 1

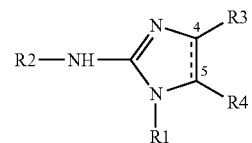

| R1 | R2 | R3 | R4 | C4-C5 bond |
|----|----|----|----|------------|
| H | Methyl | H | p-F—Ph | double |
| H | i-Propyl | H | p-Me—Ph | double |
| H | Butyl | H | Ph | double |
| H | Butyl | H | p-F—Ph | double |
| H | Butyl | H | p-Br—Ph | double |
| H | Butyl | H | p-MeO—Ph | double |
| H | Cyclopropyl | H | p-Br—Ph | double |
| H | cyclopentyl | H | Ph | double |
| H | cyclopentyl | H | p-Cl—Ph | double |
| H | cyclopentyl | H | p-Br—Ph | double |
| H | cyclopentyl | H | p-NO2—Ph | double |
| H | cyclopentyl | H | Bi—Ph | double |
| H | cyclopentyl | H | 3,4-diCl—Ph | double |
| H | Cyclohexyl | H | p-NO2—Ph | double |
| H | Benzyl | H | p-Cl—Ph | double |
| H | piperonyl | H | p-F—Ph | double |
| H | 2-(3-MeOPh)Ethy | | p-NO2—Ph | double |

It has also been demonstrated that 2-(substituted amino) imidazoline compounds according the structural formula (C) wherein R1, R2, R3 and R4 are as defined in table 2 below are capable of inhibiting biofilm formation.

TABLE 2

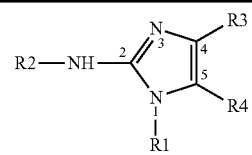

| R1 | R2 | R3 | R4 | C4-C5 bond |
|----|----|----|----|------------|
| H |  | H | H | single |
| H | 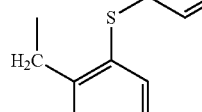 | H | H | single |
| H | 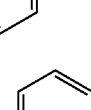 | H | H | single |
| H | 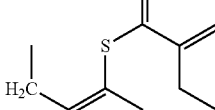 | H | H | single |

It has also been demonstrated that 2-(substituted amino) imidazole compounds according the structural formula (B) wherein R1, R2, R3 and R4 are as defined in table 3 (wherein Ph stands for phenyl.) below are capable of acting as antibacterial agents.

TABLE 3

| R1 | R2 | R3 | R4 |
|----|----|----|----|
| H | Benzyl | H | p-Cl—Ph |
| H | cyclopentyl | H | p-Cl—Ph |
| H | cyclopentyl | H | p-Br—Ph |
| H | cyclopentyl | H | 3,4-diCl—Ph |

Substituted 2-aminoimidazoles represented by the structural formula (I), wherein ring A is an imidazolinyl structure represented by formula (C) may be included in the antimicrobial compositions of this invention. Such compounds may be produced by performing a sequence of method steps well known in the art. One synthetic procedure is schematically shown below.

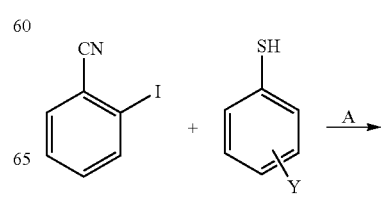

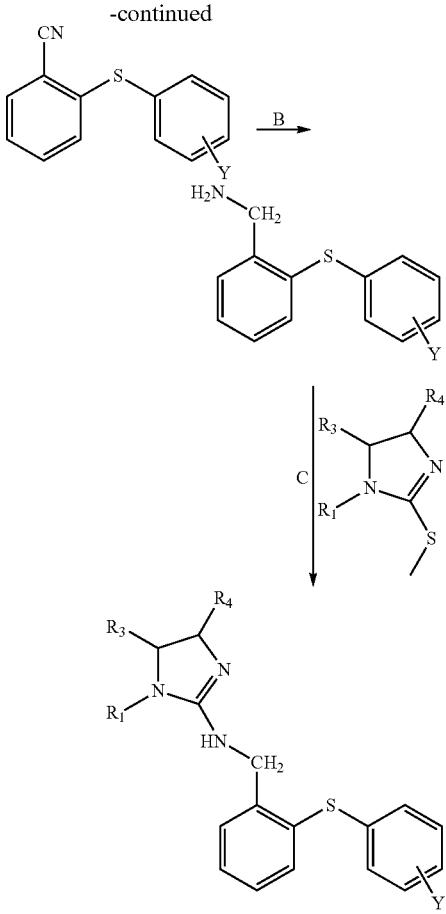

In a first step (reaction A), an optionally substituted iodobenzonitrile is condensed with an optionally substituted thiophenol (wherein the optional substituent is designated as Y in the above scheme) under basic conditions and in the presence of a suitable condensation catalyst, as disclosed in *Eur. J. Org. Chem.* (2008) 640-3. Although not shown in the above scheme, a similar procedure may be performed starting from an optionally substituted phenol. A representative but non-limiting detailed procedure for reaction A is as follows: to a solution of KOH (1.5 mmole) in 1 mL water, were added 1 mmole tetrabutylammonium iodide, 1 mole % copper (I) iodide, 1.1 mmole iodobenzonitrile and 1 mmole of the optionally substituted thiophenol. The reaction mixture was stirred at 80° C. during 10 hours. After cooling down, dichloromethane was used to extract the water phase (3×2 mL). The organic phase was washed 3 times with brine and dried. The solvent was evaporated under reduced pressure and the residue was purified with chromatography on silica with a mixture petroleum ether/ethyl acetate 10:1 as eluent to provide the condensation product in good yield.

In a second step (reaction B), the cyano group of the condensation product from reaction A is converted into an aminomethyl group using reaction conditions well known in the art, e.g. from *Eur. J. Org. Chem.* (2008) 3314-3327. A representative but non-limiting detailed procedure for reaction B is as follows: 1 mmole of the benzonitrile derivative is added to 7 mL of dry THF. The solution is cooled down to 0° C. and flushed with $N_2$ then with argon. 2 mmoles $LiAlH_4$ in dry THF are added slowly within 1 hour. The reaction mixture is slowly warmed up to room temperature and then stirred during 5 hours. The reaction is then quenched with water (15 mL) and the resulting biphasic solution is extracted with dichloromethane (3×5 mL). The organic phase is washed with NAOH 10% and brine (15 mL), dried, filtrated and evaporated under vacuum to provide the aminomethyl aromatic derivative in good yield.

In a third step (reaction C), the aminomethyl aromatic derivative is reacted with a 2-(methylthio)-4,5-dihydro-imidazole derivative which may be substituted as required at positions 1, 4 and/or 5 of the imidazolyl ring, using reaction conditions well known in the art, e.g. from *J. Pharmacy & Pharmacology* (2006) 58:1415-1420. A representative but non-limiting detailed procedure for reaction C is as follows: In 25 mL acetonitrile, 1 mmole of the aminomethyl aromatic derivative from step B and 1 mmole of 2-(methylthio)-4,5-dihydro-imidazole derivative are stirred under reflux during 36 hours. After cooling down, the mixture is evaporated under strong vacuum, triturated with diethylether and filtrated. The solvent is evaporated under vacuum and the residue is purified on chromatography.

One specific embodiment of this aspect of the present invention relates to a composition wherein said compound is a known substituted 2-aminoimidazole as defined in CLAIM 10 of International application No. PCT/EP2010/070149 (which is hereby incorporated by reference).

Another specific embodiment of the present invention relates to a composition wherein R3 is as defined in CLAIM 11 of International application No. PCT/EP2010/070149 (which is hereby incorporated by reference), in combination with the aforementioned definitions of R1, R2 and R4.

Another specific embodiment of the present invention relates to a composition wherein R3 is as defined in CLAIM 11 of International application No. PCT/EP2010/070149 (which is hereby incorporated by reference), and wherein R1 is hydrogen, in combination with the aforementioned definitions of R2 and R4.

Another specific embodiment of the present invention relates to a composition wherein R3 is as defined in CLAIM 11 of International application No. PCT/EP2010/070149 (which is hereby incorporated by reference), and wherein R4 is hydrogen, in combination with the aforementioned definitions of R1 and R2.

Another specific embodiment of the present invention relates to a composition wherein R3 is as defined in CLAIM 11 of International application No. PCT/EP2010/070149 (which is hereby incorporated by reference), and wherein R1 and R4 are hydrogen, in combination with the aforementioned definition of R2.

Another specific embodiment of the present invention relates to a composition wherein R2 is as defined in CLAIM 12 of International application No. PCT/EP2010/070149 (which is hereby incorporated by reference), in combination with the aforementioned definitions of R1, R3 and R4.

Another specific embodiment of the present invention relates to a composition wherein R2 is as defined in CLAIM 12 of International application No. PCT/EP2010/070149 (which is hereby incorporated by reference), and wherein R1 is hydrogen, in combination with the aforementioned definitions of R3 and R4.

Another specific embodiment of the present invention relates to a composition wherein R2 is as defined in CLAIM 12 of International application No. PCT/EP2010/070149 (which is hereby incorporated by reference), and wherein R4 is hydrogen, in combination with the aforementioned definitions of R1 and R3.

Another specific embodiment of the present invention relates to a composition wherein R2 is as defined in CLAIM 12 of International application No. PCT/EP2010/070149

(which is hereby incorporated by reference), and wherein R1 and R4 are hydrogen, in combination with the aforementioned definition of R3.

Another specific embodiment of the present invention relates to a composition R2 is as defined in CLAIM 13 of International application No. PCT/EP2010/070149 (which is hereby incorporated by reference).

Another specific embodiment of the present invention relates to a composition wherein said compound is a known (commercial) substituted 2-aminoimidazoline as defined in CLAIM 14 of International application No. PCT/EP2010/070149 (which is hereby incorporated by reference).

Another specific embodiment of the present invention relates to a composition wherein said compound is an imidazo[1,2-a]pyrimidinium salt being represented by the structural formula (II) and wherein $X^-$ is an inorganic or organic anion, in combination with the aforementioned definitions of R1, R2, R3, R4, R5, R6, R7 and R8.

Another specific embodiment of the present invention relates to a composition wherein said compound is as defined in CLAIM 15 of International application No. PCT/EP2010/070149 (which is hereby incorporated by reference), in combination with the aforementioned definitions of R1, R2, R3, R4, R5, R6, R7 and R8.

Another specific embodiment of the present invention relates to a composition as defined in CLAIM 16 of International application No. PCT/EP2010/070149 (which is hereby incorporated by reference).

Another specific embodiment of the present invention relates to a composition wherein said compound is a salt wherein R1 is as defined in CLAIM 17 of International application No. PCT/EP2010/070149 (which is hereby incorporated by reference), in combination with the aforementioned definitions of $X^-$, R2, R3, R4, R5, R6, R7 and R8.

Another specific embodiment of the present invention relates to a composition wherein said compound is a salt wherein R1 is as defined in CLAIM 17 of International application No. PCT/EP2010/070149 (which is hereby incorporated by reference), and wherein each of R6, R7 and R8 is hydrogen, in combination with the aforementioned definitions of $X^-$, R2, R3, R4 and R5.

Another specific embodiment of the present invention relates to a composition wherein said compound is a salt wherein R3 is as defined in CLAIM 18 of International application No. PCT/EP2010/070149 (which is hereby incorporated by reference), in combination with the aforementioned definitions of $X^-$, R1, R2, R4, R5, R6, R7 and R8.

Another specific embodiment of the present invention relates to a composition wherein said compound is a salt wherein R3 is as defined in CLAIM 18 of International application No. PCT/EP2010/070149 (which is hereby incorporated by reference), and wherein each of R6, R7 and R8 is hydrogen, in combination with the aforementioned definitions of $X^-$, R1, R2, R4 and R5.

The antimicrobial compositions of the second aspect of this invention may, either for improved efficiency or for controlling several types of microbes in the same or a vicinal locus of a human, an animal or a plant, further comprise an effective amount of another anti-microbial (e.g. antibacterial, antiprotozoal or antifungal) entity or agent. Such combination of active agents may be in the form of a kit wherein each agent is kept separate until effective use. The other anti-microbial entity may be a biocide, an antibiotic agent or another specific therapeutic entity. Suitable antibiotic agents include, without limitation, penicillin, quinoline, vancomycin, sulfonamides, ampicillin, ciprofloxacin, and sulfisoxazole. The specific therapeutic entity can include a targeting moiety coupled to an anti-microbial peptide moiety.

The antimicrobial compositions of the second aspect of this invention may, depending upon the desired mode of administration or application, be formulated in very different forms such as, but not limited to, liquids, gels, foams, semi-solids and solids. Practically these compositions can be in the form of an oral tablet, a capsule, a nasal aerosol, a liquid, such as throat wash, mouth wash or gargle, a tooth-paste or a topical ointment. They can be in the form of tampons, rinses, creams or aerosols, soaps, hair shampoos, antiperspirants, facial tissues, skin cleansers, component of a wound dressing or any device suitable for sanitation or hygienic treatment.

When the antimicrobial compositions of this invention are formulated as liquids, at least one excipient may be a solvent for the biologically effective imidazo[1,2-a]pyrimidinium salt or substituted 2-aminoimidazole. Said solvent may be as defined in claim 20 of International application No. PCT/EP2010/070149 (which is hereby incorporated by reference), but is not limited thereto. The respective proportions of the active compound and the solvent in the liquid formulation are mainly determined by the solubility limit of the active compound in the relevant solvent, which can readily be determined by the skilled person. A liquid antimicrobial composition of this invention may also be in the form of a kit where the active compound and the solvent are kept separately until effective use.

For an effective treatment, since the imidazo[1,2-a]pyrimidinium salt or a substituted 2-aminoimidazole may become toxic above a certain concentration, it is necessary for safety reasons to provide administration or application in the form of a composition comprising one or more excipients. Particularly preferred are compositions as defined in claim 21 or in claim 22 of International application No. PCT/EP2010/070149 (which is hereby incorporated by reference).

The anti-microbial compositions of the present invention can include one or more non-active excipients or ingredients, e.g., ingredients that do not interfere with the biofilm inhibiting function of the active compound. The non-active ingredient can be a powder, an encapsulated solid, or an aqueous carrier. In one embodiment, the compositions of the present invention in oral form may include, without limitation, thickening materials, humectants, water, buffering agents, surfactants, titanium dioxide, flavouring systems, sweetening agents, colouring agents, and mixtures thereof. Pharmaceutically acceptable excipients, ingredients and carriers are well known, and one skilled in the pharmaceutical art can easily select them for any particular route of administration (Remington's Pharmaceutical Sciences, Mack Publishing Co., Easton, Pa., 1985).

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkyl-methylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronization, for instance in view to obtain them in the form of microspheres usually having a diameter of about 1 to 10 μm, namely for the manufacture of microcapsules for controlled or sustained release of the active ingredients.

Suitable surface-active agents, also known as emulsifiers, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulfonic acid or dodecylsulfonic acid or a mixture of fatty alcohol sulfates obtained from natural fatty acids, alkaline or alkaline-earth metal salts of sulfuric or sulphonic acid esters (such as sodium lauryl sulfate) and sulfonic acids of fatty alcohol/ethylene oxide adducts. Suitable sulfonated benzimidazole derivatives preferably contain 8 to 22 carbon atoms. Examples of alkylarylsulfonates are the sodium, calcium or alcanolamine salts of dodecylbenzene sulfonic acid or dibutyl-naphthalenesulfonic acid or a naphthalene-sulfonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidyl glycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulfonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered to a human or animal by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

The formulations may conveniently be presented in unit dosage form and may be prepared by any of the methods well known in the art of pharmacy. Such methods include the step of bringing into association the active ingredient with the carrier(s). In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active and/or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.05 to 30% w/w, preferably 0.2 to 20% w/w, more preferably 0.5 to 15% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. The choice of suitable oils or fats for the formulation is based on achieving the desired properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns, which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

Compounds of the invention can be used in pharmaceutical formulations ("controlled release formulations") in which the release of the active ingredient can be controlled and regulated to allow less frequency dosing or to improve the pharmacokinetic or toxicity profile of a given compound. Controlled release formulations adapted for oral administration in which discrete units comprising one or more compounds of the invention can be prepared according to conventional methods. Additional ingredients may be included in order to control the duration of action of the active ingredient in the composition. Control release compositions may thus be achieved by selecting appropriate polymer carriers such as for example polyesters, polyamino acids, polyvinylpyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods also include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

Preferably the antimicrobial compositions of this invention are formulated for long-term storage such as concentrated solutions or lyophilized powder preparations. They may also be included in vesicles, e.g. liposomes, or be formulated as controlled release systems, using controlled release technologies known in the art.

When the antimicrobial compositions of this invention are formulated as gels or foams, they may be enclosed within a dispensing device for gel or foam.

The third aspect of the present invention will now be described with respect to a number of specific valuable embodiments.

The method of this aspect of the invention is effective against a wide selection of microbes. For instance one specific embodiment of this invention relates to a method as defined in claim 25 of International application No. PCT/EP2010/070149 (which is hereby incorporated by reference).

When intended for a human or an animal such as, but not limited to, a mammal, a domestic animal or cattle, the method of treatment of this invention may be by administering the anti-microbial composition intravesicularly, topically, orally, rectally, ocularly, otically, nasally, parenterally, vaginally, intravenously, topically to an infected body part of said human or animal. Said body part may be an epithelial surface or a mucosal surface. Said mucosal surface may be as defined in claim 27 of International application No. PCT/EP2010/070149 (which is hereby incorporated by reference). When intended for disinfecting a surface which may come into contact with a human or an animal such as, but not limited to, a medical device or an implantable device (e.g. a prosthetic device, a heart valve, a pacemaker, a dental device, a stent or a catheter or a prosthetic bladder material), the method of treatment of this invention may be by dipping said medical device into the anti-microbial composition, one or more times and for a sufficient period of time to significantly decrease or eliminate the target germs. The surface to be disinfected may be e.g. a biological surface or an inert solid industrial or domestic surface such as a heat exchanger, an air-filtering device, a component of an aquaculture system, kitchenware or a pipeline or a building part susceptible to biofilm formation, or a surface in a hospital such as in a surgery unit where sanitization is essential. The material from which said surface is made is not a critical parameter of the method of the invention, as soon as it is susceptible to biofilm formation. The surface can include a plastic such as a silicone or another type of polymeric material.

Another specific embodiment of the present invention relates to a method for disinfecting or sterilizing a surface ex-vivo to remove a biofilm or prevent biofilm growth.

Another specific embodiment of the present invention relates to a method wherein an anti-microbial composition as defined hereinabove is co-administered or co-applied (either simultaneous or sequential co-administration) with one or more other antibacterial agents. Any anti-microbial agent (in particular a fungicide or a bactericide), admissible for use in plants, animals and humans is suitable for such co-administration or co-application. They include for instance anti-microbial agents such as broad spectrum antibiotics for combating clinical and sub-clinical infection, for example gentamycin, vancomycine, analogs thereof and the like.

Without wishing to be bound by theory, it is believed that the active compounds represented by the structural formula (I) or the structural formula (I) are able to perform biofilm inhibition in the method of treatment of this invention through one or more of the following mechanisms of action:
- Activation of the PhoPQ regulon,
- Downregulation of csgD, a master regulator for biofilm formation, both in a PhoPQ dependent manner, and in a PhoPQ independent manner,
- Decreasing motility of microorganisms,
- Interfering with nucleotide biosynthesis, in particular purine nucleotide biosynthesis and pyrimidine nucleotide biosynthesis, thus potentially decreasing bioavailability of the messenger molecule c-di-GMP which is crucial for biofilm formation.

The biofilm inhibitor of this invention may be capable of complexing, or reversibly binding to, the organic matrix material, thereby rendering the organic matrix water insoluble. The biofilm inhibitor may exhibit greater binding affinity for functional groups in cellular proteins of microorganisms. When a microorganism contacts the anti-biofilm material of this invention, the organic material engages or disrupts at least the outer portion of the lipid bilayer of the microorganism's cell membrane sufficiently to permit insinuation of the biofilm inhibitor into the microorganism, where cell proteins or proteins in the lipid bilayer compete effectively for the biofilm inhibitor due to favourable binding constants. Stated another way, the biofilm inhibitor binds to or forms a complex with the organic material in which the association between the organic material and biofilm inhibitor is sufficiently strong that the layer or film does not elute anti-biofilm amounts of the biofilm inhibitor into a contacting solution. However, the biofilm inhibitor preferentially binds to certain proteins in the microorganism and thus is transferred from the matrix to the microorganism. The result is a contact-biofilm preventing delivery system that selectively transfers the biofilm inhibitor or into the microorganism's cell membrane upon contact, without elution or dissolution of the biofilm inhibitor into solution, thereby maintaining the long term anti-biofilm efficacy of the composition.

The compositions and methods of this invention are especially useful for treating or preventing a pathologic condition associated with a microbial infection or for decreasing bacterial growth in an animal or a human in need of such treatment.

The compositions and methods of this invention are especially useful for treating a human with a wound selected from the group consisting of an ulcer, a laceration, a deep penetrating wound and a surgical wound.

The compositions and methods of this invention are also useful for reducing the risk of bacterial infection or sepsis in a person colonized with pathogenic bacteria. This is especially relevant to immuno-compromised patients affected with leukaemia, lymphoma, carcinoma, sarcoma, allogenic transplant, congenital or acquired immunodeficiency, cystic fibrosis, and AIDS.

The compositions and methods of this invention are especially useful for reducing the risk of bacterial infection in a human, wherein the pathogenic bacteria are selected from the group consisting of pneumococcal species, methicillin-resistant *Staphylococcus aureus*, multi-drug resistant *Pseudomonas* species, *Nesseria* sp., *Hemophilus* sp., *Proteus* sp., *Klebsiella* sp. and *Escherichia coli*.

The compositions and methods of this invention are also useful for reducing the risk of bacterial infection in a person, wherein the pathogenic bacteria are gram negative bacteria selected from the group consisting of *Salmonella*, e.g. *S. Typhimurium*, *S. Enteritidis*, *S. arizonae*, *S. bongori*, *S. cholerae-suis*, *S. choleraesuis*, *S. enterica*, *S. paratyphi*, *S. pullorum*, *S. subterranea*, and *S. typhi* or *Pseudomonas*, e.g; a bacterium of the *Pseudomonas aeruginosa* group such as *P. aeruginosa* group *P. aeruginosa*, *P. alcaligenes*, *P. anguilliseptica*, *P. argentinensis*, *P. borbori*, *P. citronellolis*, *P. flavescens*, *P. mendocina*, *P. nitroreducens*, *P. oleovorans*, *P. pseudoalcaligenes*, *P. resinovorans* or *P. straminea*.

Yet another embodiment of the present invention is a process for imparting microbial control properties to a fluid composition, said process comprising adding an anti-microbial composition as defined hereinabove to said fluid composition. Fluid compositions involved in this embodiment of the invention may be, but are not limited to, aqueous compositions susceptible to come into contact with, and subsequently infect, a plant, an animal or a human being.

EXAMPLE 1

Production Method (General Procedure) for Substituted Imidazo[1,2-a]pyrimidinium Salts and Substituted 2-aminoimidazoles The compounds of the present invention—both substituted imidazo[1,2-a]pyrimidinium salts having formula (II) and substituted 2-aminoimidazoles having formula (I)—can be produced by applying the synthetic method known from *J. Org. Chem.* (2008) 73:6695-6694, and schematically shown below:

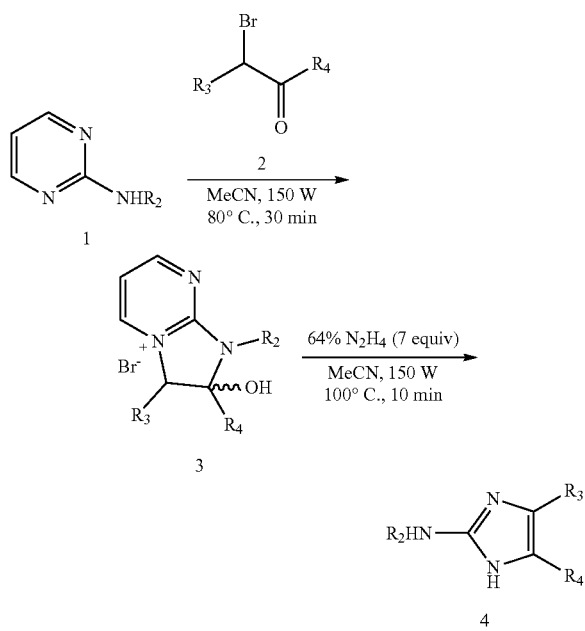

A representative but non-limiting methodology is as follows. In a 30 mL microwave vial were successively brought acetonitrile (15 mL), 2-alkylaminopyrimidine 1 (5 mmoles), α-bromoketone 2 (6 mmoles) and a catalytic amount of 4-dimethylaminopyridine (0.05 mmole). The reaction tube was sealed, and irradiated in a microwave reactor at a temperature of 80° C. and 150 W maximum power for 30 to 45 minutes. After the reaction mixture was cooled with an air flow for 15 minutes, the resulting precipitate was washed with acetone (25 mL), ether (20 mL) and dried in vacuum to afford the imidazo[1,2-a]pyrimidinium salt 3 as a white powder.

Then, to a suspension of the imidazo[1,2-a]pyrimidinium salt 3 (2 mmoles) in acetonitrile (5 mL), hydrazine hydrate (0.7 mL, 14 mmoles of a 64% solution) was added, and the mixture was irradiated in the sealed reaction tube for 10 minutes at a temperature of 100° C. at 150 W maximum power. After cooling down, hydrazine hydrate was evaporated with toluene (3×20 mL). The resulting residue was purified by column chromatography (silica gel; MeOH-DCM 1:4 v/v with 5% of 6M $NH_3$ in MeOH) to afford the substituted 2-amino-1H-imidazole 4 as an amorphous solid.

EXAMPLE 2

Anti-Bacterial Activity of Substituted 2-amino-1H-imidazoles

Evaluation of antibacterial-inhibitory activity of some substituted 2-amino-1H-imidazoles of the invention was carried out by diluting an overnight culture of *Salmonella Typhimurium* ATCC 14028 into a liquid medium. 200 μl of the diluted overnight culture was added to each well of a microtiter plate together with different concentrations of the test compound (1/2 dilution series of the compound). After an incubation of 24 hours the optical density at 600 nm of each well was determined with a microtiter plate reader. From these measurements the concentration of the test compound at which 50% inhibition was observed ($GIC_{50}$ value) was calculated. The compounds of the invention had a good antibacterial inhibitory. The $IC_{50}$ values of representative compounds for antibacterial activity are shown in the following Table 4.

TABLE 4

| R1 | R2 | R3 | R4 | $GIC(50)^a$ (μM) |
|---|---|---|---|---|
| H | Benzyl | H | p-Cl—Ph | 100 |
| H | cyclopent | H | p-Cl—Ph | 45 |
| H | cyclopent | H | p-Br—Ph | 50-100 |
| H | cyclopent | H | 3,4-diCl—Ph | 50 |

$^a$GIC50: 50% inhibitory concentration for growth inhibition: determined by measuring the OD600 after 24 hours of growth in the presence of different concentrations of the compound.

EXAMPLE 3

Biofilm Formation Inhibiting Activity of Substituted 2-amino-1H-imidazoles

Evaluation of the biofilm inhibitory activity of some substituted 2-amino-1H-imidazoles of the invention was carried out by growing up biofilms of *S. Typhimurium* ATCC14028 or SL1344 or *Pseudomonas aeruginosa* PA14 in the presence of different concentrations (1/2 dilution series) of biofilm inhibitors, by using the Calgary biofilm device. After an incubation period of 24 hours at 25° C. or 37° C. or 48 hours at 16° C. the biofilms were visualized by crystal violet staining. In the next step the stain was extracted from the biofilm with 30% acetic acid. The absorbance of the resolubilized stain at 570 nm is a measure of the amount of biofilm formed. From these measurements the concentration of the test compound at which 50% biofilm inhibition was observed ($IC_{50}$ value) was calculated. The $IC_{50}$ values of representative compounds for biofilm inhibition are shown in the following Tables 5 to 7 below and in the table 8 of the appended figure (wherein Ph stands for phenyl).

TABLE 5 biofilm inhibition of *S. Typhimurium* ATCC14028 at 25° C.

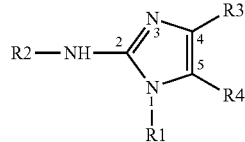

| R1 | R2 | R3 | R4 | IC50 for biofilm inhibition (25° C.) (μM) |
|---|---|---|---|---|
| H | Methyl | H | p-F—Ph | 102 |
| H | i-Propyl | H | p-Me—Ph | 99 |
| H | Butyl | H | Ph | 25 |
| H | Butyl | H | p-F—Ph | 16 |
| H | Butyl | H | p-Br—Ph | 7 |
| H | Butyl | H | p-MeO—Ph | 49 |
| H | cyclopentyl | H | p-Br—Ph | 95 |
| H | cyclopentyl | H | Ph | 53 |
| H | cyclopentyl | H | p-Cl—Ph | 4 |
| H | cyclopentyl | H | p-Br—Ph | 12 |
| H | cyclopentyl | H | p-NO2—Ph | 12 |
| H | cyclopentyl | H | Bi—Ph | 46 |
| H | cyclopentyl | H | 3,4-diCl—Ph | 6 |

TABLE 5-continued biofilm inhibition of *S. Typhimurium* ATCC14028 at 25° C.

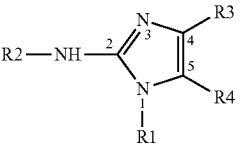

| R1 | R2 | R3 | R4 | IC50 for biofilm inhibition (25° C.) (μM) |
|---|---|---|---|---|
| H | Cyclohexyl | H | p-NO2—Ph | 44 |
| H | Benzyl | H | p-Cl—Ph | 31 |
| H | piperonyl | H | p-F—Ph | 68 |
| H | 2-(3-MeO—Ph)Ethyl | H | p-NO$_2$—Ph | 15 |

TABLE 6

*Pseudomonas aeruginosa* PA14 biofilm formation at 25° C.

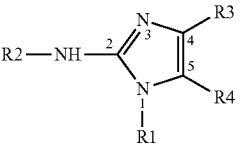

| R1 | R2 | R3 | R4 | IC50 for biofilm inhibition (25° C.) (μM) |
|---|---|---|---|---|
| H | Butyl | H | p-FPh | 6 |
| H | cyclopentyl | H | 3,4-diCl—Ph | 1 |

TABLE 7 biofilm inhibittion of *S. Typhimurim* ATCC14028 and SL1344 by substituted 2-aminoimidazolines at 16° C.

| | | Compounds | | | |
|---|---|---|---|---|---|
| Strain | Biofilm/planktonic growth | Specs3 | Specs3-1 | Specs3-3 | Specs3-4 |
| ATCC14028 | IC50 biofilm inhibition (μM) | 21.86 | 41.95 | 32.86 | 16.61 |
| ATCC14028 | IC50 growth inhibition (μM) | 283 | 416.7 | 264.6 | 82.57 |
| SL1344 | IC50 biofilm inhibition (μM) | ~31.78 | ~65.90 | 68.12 | 15.49 |
| SL1344 | IC50 growth inhibition (μM) | 283 | 416.7 | 264.6 | 82.57 |

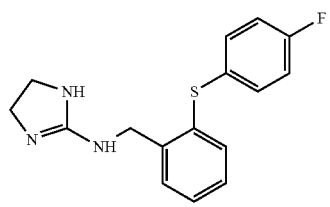

specs3

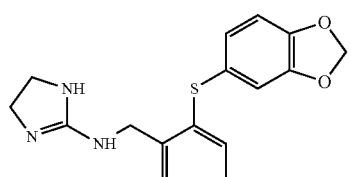

specs3-1

TABLE 7-continued biofilm inhibittion of *S. Typhimurim* ATCC14028 and SL1344 by substituted 2-aminoimidazolines at 16° C.

| Strain | Biofilm/planktonic growth | Compounds |
|---|---|---|
| | | Specs3 Specs3-1 Specs3-3 Specs3-4 |

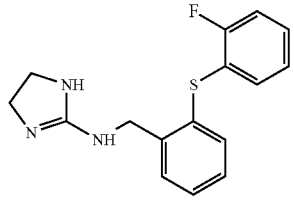

specs3-3

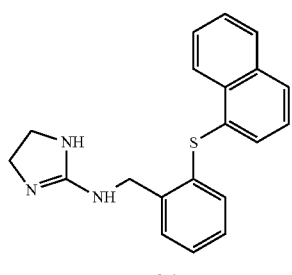

specs3-4

Some of the tested compounds show a concentration range in which biofilm formation is inhibited but no effect on planktonic growth is observed. These compounds are particularly interesting for prevention of biofilm formation since the development of resistance against these compounds is less likely. Table 8 indicates whether the different compounds have an effect on the planktonic growth of the bacteria at the IC50 for biofilm inhibition. To construct Table 8, the effect of the tested compounds on the growth curve of the bacteria was determined at a concentration equal to the IC50 for biofilm inhibition, by using the Bioscreen system available from Oy Growth Curves Ab Ltd).

In Table 8:

[a]x means: no influence on planktonic growth at the IC50 for biofilm inhibition

[b]nd means: not determined

[c]o means: planktonic growth is retarded at the IC50 for biofilm inhibition

[d]S1 means:

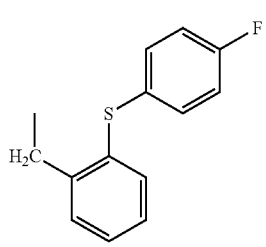

S2 means:

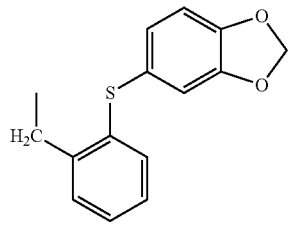 [SMILES: CCc1ccccc1Sc1ccc2c(c1)OCO2]

[f]S3 means:

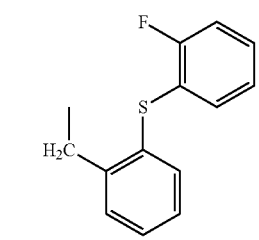 [SMILES: CCc1ccccc1Sc1ccccc1F]

[g]S4 means:

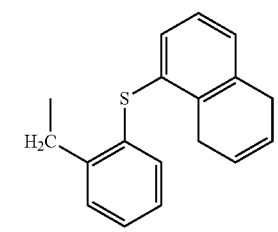 [SMILES: CCc1ccccc1Sc1cccc2c1CC=CC2]

In examples 2 and 3, the following materials and methods were used. Stock solutions of all compounds assayed for biological activity were prepared in DMSO or EtOH and stored at −20° C. The amount of solvent used in biofilm inhibition screens and growth inhibition screens did not exceed 2% (by volume).

Static Peg Assay for Prevention of *Salmonella typhimurium* Biofilm Formation

The device used for biofilm formation is a platform carrying 96 polystyrene pegs (Nunc no. 445497) that fits as a microtiter plate lid with a peg hanging into each microtiter plate well (Nunc no. 269789). Biofilm formation assays were carried out at 16° C., 25° C. and 37° C.

For biofilm assays at 16° C. and 25° C., two-fold serial dilutions of the compounds in 100 μl liquid TSB 1/20 broth per well were prepared in the microtiter plate. Subsequently, an overnight culture of *S. Typhimurium* ATCC14028 or SL1344 (grown up in LB medium) was diluted 1:100 into TSB 1/20 broth and 100 μl (ca. $10^6$ cells) was added to each well of the microtiter plates, resulting in a total amount of 200 μl medium per well. The pegged lid was placed on the microtiter plate and the plate was incubated for 48 hours at 16° C. or for 24 hours at 25° C. without shaking. During this incubation period biofilms were formed on the surface of the pegs. In case of the assay at 16° C., after 24 hours the lid was transferred into a new plate with medium and the specific molecules used for testing. The optical density at 600 nm (OD600) was measured for the planktonic cells in the first plate using a VERSAmax microtiter plate reader (Molecular Devices) and the growth retarding concentration IC50 for growth inhibition was determined as the concentration that decreases the OD600 of the planktonic cells 50%. For quantification of biofilm formation, the pegs were washed once in 200 μl phosphate buffered saline (PBS). The remaining attached bacteria were stained for 30 minutes with 200 μl 0.1% (w/v) crystal violet in an isopropanol/methanol/PBS solution (v/v 1:1:18). Excess stain was rinsed off by placing the pegs in a 96-well plate filled with 200 μl distilled water per well. After the pegs were air dried (30 min), the dye bound to the adherent cells was extracted with 30% glacial acetic acid (200 μl). The OD570 of each well was measured using the VERSAmax microtiter plate reader. The IC50 value for each compound was determined from concentration gradients in two or three independent experiments (with 2 or 3 repeats per experiment), by using the GraphPad software of Prism.

For biofilm assays at 37° C., two-fold serial dilutions of the compounds in 50 μl liquid CFA broth per well were prepared in the microtiter plate. Subsequently, an overnight culture of *S. Typhimurium* ATCC 14028 was diluted 1:100 into CFA broth and 100 μl (ca. $10^6$ cells) was added to each well of the microtiter plates, resulting in a total amount of 150 μl medium per well. The pegged lid was placed on the microtiter plate and the plate was incubated for 24 hours at 37° C. without shaking. During incubation the plates were placed in a humidity controlled container to prevent evaporation of the growth medium. Quantification of biofilm formation was performed similarly as described above for the assays at 16° C. and 25° C.

Static Peg Assay for Prevention of *Pseudomonas aeruginosa* Biofilm Formation

The device used for *Pseudomonas aeruginosa* biofilm formation is the same platform carrying polystyrene pegs as described above for *Salmonella Typhimurium*.

Two-fold serial dilutions of the compounds in 100 μl liquid broth per well were prepared in the microtiter plate. Subsequently, an overnight culture of *P. aeruginosa* PA14 (grown up in TSB medium) was diluted 1:100 into liquid broth and 100 μl was added to each well of the microtiter plates, resulting in a total amount of 200 μl medium per well. The pegged lid was placed on the microtiter plate and the plate was incubated for 24 hours at 25° C., 30° C. or 37° C. without shaking. During this incubation period biofilms were formed on the surface of the pegs. The liquid broth used for the tests at 25° C. was TSB 1/20. The tests at 37° C. were performed in CFA and/or LBNS broth. During incubation at 30° C. and 37° C. the plates were placed in a humidity controlled container to prevent evaporation of the growth medium. Quantification of biofilm formation was performed similarly as described previously for the *S. Typhimurium* biofilm assays.

Bioscreen Assay for Measuring Growth Inhibition

The Bioscreen device from Oy Growth Curves Ab Ltd was used for measuring the influence of the chemical compounds on the planktonic growth of *Salmonella Typhimurium* and *Pseudomonas aeruginosa*. The Bioscreen is a computer controlled incubator/reader/shaker that uses 10×10 well microtiter plates and measures light absorbance of each well at a specified wave length in function of time.

An overnight culture of *S. Typhimurium* ATCC14028 or SL1344 (grown up in LB medium) or *Pseudomonas aeruginosa* PA14 (grown up in TSB medium) was diluted 1:200 in liquid broth. The broth used was TSB 1/20 for the experiments at 16° C. and 25° C. For experiments at 37° C. CFA medium was used for *S. Typhimurium* and LBNS medium for *P. aeruginosa*. 300 μl of the diluted overnight culture was added to each well of the 10×10 well microtiter plate. Subsequently serial dilutions of the chemical compounds were prepared in DMSO or EtOH. 3 μl of each diluted stock solution was added to the wells (containing the 300 μl bacterial culture) in 3-fold. As a control 3 μl of the appropriate solvent (DMSO or EtOH) was also added to the plate in 3- or 4-fold. The microtiter plate was incubated in the Bioscreen device at 16° C., 25° C. or 37° C. for at least 36 hours, with continious medium shaking. The absorbance of each well was measured at 600 nm each 15 minutes. Excel was used to generate the growth curves for treated the treated wells and the untreated control wells.

Measuring Antibacterial Properties

Starting from a 40 mM stock solution of each compound in DMSO, two-fold serial dilutions in 100 μl liquid broth per well were prepared in dublicate in sterile transparant microtiter plates. The broth used was TSB 1/20 for measurements at 25° C. and CFA (in case of *Salmonella Typhimurium*) and LBNS (in case of *Pseudomonas aeruginosa*) for measurements at 37° C. Subsequently an overnight culture of the bacteria (*S. Typhimurium* ATCC14028 or *P. aeruginosa* PA14) was diluted 1/200 into the corresponding liquid broth and 100 μl was added to each well of the microtiterplate resulting in a total amount of 200 μl medium per well. After an incubation of 24 hours the optical density at 600 nm of each well was determined with a microtiter plate reader (VERSAmax, Molecular Devices). From these measurements the concentration of the test compound at which 50% inhibition was observed ($GIC_{50}$ value) was calculated by using the GraphPad software of Prism.

EXAMPLE 4

Anti-Bacterial Activity of Substituted imidazo[1,2-a]pyrimidinium bromide Salts Evaluation of antibacterial-inhibitory activity of some substituted imidazo[1,2-a]pyrimidinium bromide salts of the invention was carried out by diluting an overnight culture of *Salmonella Typhimurium* ATCC14028 or *Pseudomonas aeruginosa* PA141/200 into liquid medium. 200 µl of the diluted overnight culture was added to each well of a microtiterplate together with different concentrations of the test compound (1/2 dilution series of the compound). After an incubation of 24 hours the optical density at 600 nm of each well was determined with a microtiter plate reader. From these measurements the concentration of the test compound at which 50% inhibition was observed ($GIC_{50}$ value) was calculated. The $GIC_{50}$ values of representative compounds for antibacterial activity are shown in the following Tables 9 and 10 (wherein Ph stands for phenyl, Me for methyl):

TABLE 9

Effect against *Salmonella Typhimurium* ATCC14028 at 25° C.

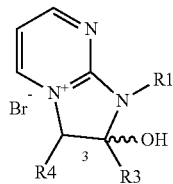

| R1 | R3 | R4 | GIC50 (µM)[a] |
|---|---|---|---|
| Cyclopropyl | 4-Cl—Ph | H | 100-200 |
| Cyclopropyl | 4-Br—Ph | H | 25-50 |
| n-butyl | dimethylphenyl | H | 50-100 |
| Cyclopentyl | 4-biphenylyl | H | 25-50 |
| Hexyl | 4-NO$_2$-Ph | H | 100-200 |
| Cyclohexyl | 4-Cl—Ph | H | 50-100 |
| Cyclohexyl | 4-MeS—Ph | H | 100-200 |
| Cyclohexyl | 4-MeO—Ph | H | 50-100 |
| Cyclohexyl | 4-Cl—Ph | H | 50-100 |
| Ph | 4-Br—Ph | Me | 50-100 |
| benzyl | 4-I—ph | H | 50-100 |
| Benzyl | 4-I—Ph | H | 50 |
| 2-(3,4-diMeO—Ph)Et | 4-NO2-Ph | H | 100-200 |
| piperonyl | 4-FPh | H | 200 |
| piperonyl | 3,4-MethylenedioxyPh | H | 100-200 |
| Cyclododecyl | 3-NO$_2$Ph | H | 6-12 |
| cyclododecyl | 4-NO$_2$Ph | H | <6 |

TABLE 10

Effect against *Pseudomonas aeruginoa* PA14 at 25° C.

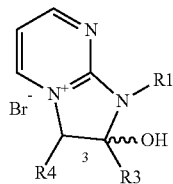

| R1 | R3 | R4 | GIC50 (µM)[a] |
|---|---|---|---|
| Cyclopenty | 4-biphenylyl | H | 27.11 |
| Cyclohexyl | 4-Cl—Ph | H | 61.3 |

TABLE 10-continued

Effect against *Pseudomonas aeruginoa* PA14 at 25° C.

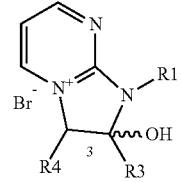

| R1 | R3 | R4 | GIC50 (µM)[a] |
|---|---|---|---|
| Benzyl | 4-I—Ph | H | 51.68 |
| cyclododecyl | 4-NO$_2$-Ph | H | 8.891 |

EXAMPLE 5

Biofilm Inhibitory Activity of Substituted imidazo[1,2-a]pyrimidinium Bromide Salts Evaluation of the biofilm inhibitory activity of some substituted imidazo[1,2-a]pyrimidinium bromide salts of the invention was carried out by growing up biofilms of *S. Typhimurium* ATCC14028 or SL1344 or *Pseudomonas aeruginosa* PA14 in the presence of different concentrations (1/2 dilution series) of biofilm inhibitors, by using the Calgary biofilm device. After an incubation period of 24 hours at 25° C. or 37° C. or 48 hours at 16° C. the biofilms were visualized by crystal violet staining. In the next step the stain was extracted from the biofilm with 30% acetic acid. The absorbance of the resolubilized stain at 570 nm is a measure of the amount of biofilm formed. From these measurements the concentration of the test compound at which 50% biofilm inhibition was observed ($IC_{50}$ value) was calculated. The $IC_{50}$ values of representative compounds for biofilm inhibitory activity are shown in the following Tables 11 to 14 (wherein Ph stands for phenyl, Me for methyl, and Bn for benzyl).

TABLE 11 biofilm formation of *S. Typhimurium* ATCC14028 at 25° C.

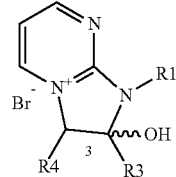

And site groups

| R1 | R3 | R4 | IC50 (µM)[a] |
|---|---|---|---|
| Isopropyl | 4-Me—Ph | H | 217.1 |
| Cyclopropyl | 4-Cl—Ph | H | 119.945 |
| Cyclopropyl | 4-Br—Ph | H | 27.00667 |
| n-Butyl | 4-Br—Ph | H | 64.89667 |
| n-Butyl | 4-F-Ph | H | 174.8 |
| cyclopentyl | 4-biphenylyl | H | 14.9 |
| Hexyl | Ph | Me | 217.7 |
| Hexyl | 4-NO2-Ph | H | 46.75 |
| cyclohexyl | 4-Cl—Ph | H | 43.79 |
| cyclohexyl | 4-MeS—Ph | H | 118 |
| cyclohexyl | 4-CN—Ph | H | 354.05 |
| cyclohexyl | 4-MeO—Ph | H | 111.84 |
| cyclohexyl | 4-Cl—Ph | H | 35.64 |
| Ph | 4-Br—Ph | Me | 57.52 |
| Bn | 4-I—Ph | H | 30.67 |

TABLE 11-continued biofilm formation of *S. Typhimurium* ATCC14028 at 25° C.

And site groups

| R1 | R3 | R4 | IC50 (μM)[a] |
|---|---|---|---|
| Bn | 4-NO$_2$-Ph | H | 221.95 |
| Bn | 4-I—Ph | H | 26.895 |
| Bn | Ph | H | 209.3 |
| 2-(3-MeOPh)Et | 3,4-diCl—Ph | H | 7.3905 |
| 2-(3-MeOPh)Et | Bi—Ph | H | 12.548 |
| 2-(3-MeOPh)Et | 4-NO2-Ph | H | 123.95 |
| 2-(3,4-diMeOPh)Et | 4-NO2-Ph | H | 126.9 |
| p-MeOBn | 4-NO2-Ph | H | 219.5 |
| p-MeOBn | 4-Br—Ph | H | 104.68 |
| piperonyl | 4-F—Ph | H | 29.35 |
| piperonyl | 3,4-methylenedioxy-Ph | H | 102.43 |
| c-Dod | 3-NO2-Ph | H | <6.25 |
| c-Dod | 4-NO2-Ph | H | <6.25 |
| tricyclo[3.3.1.13,7]dec-1-yl | 4-NO2-Ph | H | 8.801 |

TABLE 12

*P. aeruginosa* PA14 biofilm formation at 25° C.

| R1 | R3 | R4 | IC50 (μM)[a] |
|---|---|---|---|
| Cyclopentyl | 4-biphenylyl | H | 1.568 |
| Cyclohexyl | 4-ClPh | H | 4.936 |

TABLE 12-continued

*P. aeruginosa* PA14 biofilm formation at 25° C.

| R1 | R3 | R4 | IC50 (μM)[a] |
|---|---|---|---|
| Bn | 4-IPh | H | 8.609 |
| cyclododecyl | 4-NO2Ph | H | 6.316 |

TABLE 13

*P. aeruginosa* PA14 biofilm formation at 37° C.

| R1 | R3 | R4 | IC50 (μM)[a] |
|---|---|---|---|
| cyclopentyl | Bi—Ph | H | 62.05 |
| Bn | 4-I—Ph | H | 175 |
| cyclododecyl | 4-NO2-Ph | H | 18.2 |

Some of the compounds show a concentration range in which biofilm formation is inhibited but no effect on the planktonic growth is observed. Table 14 indicates if the different compounds have an effect on the planktonic growth of the bacteria at the IC50 for biofilm inhibition. To construct this table the effect of the compounds on the growth curve of the bacteria was determined at a concentration equal to the IC50 for biofilm inhibtion, by using the Bioscreen system from Oy Growth Curves Ab Ltd.

TABLE 14 effect on planktonic growth at the IC50 for biofilm inhibition (25° C.)

| R1 | R3 | R4 | *Salmonella Typhimurium* ATCC14028 | | *Pseudomonas aeruginosa* PA14 | |
|---|---|---|---|---|---|---|
| | | | IC50 biofilm inhibition (μM) | Influence on growth | IC50 biofilm inhibition (μM) | Influence on growth |
| Isopropyl | 4-MePh | H | 217.1 | nd | nd | nd |
| Cyclopropyl | 4-ClPh | H | 119.945 | nd | nd | nd |
| Cyclopropyl | 4-BrPh | H | 27.00667 | x | nd | nd |
| n-Butyl | 4-BrPh | H | 64.89667 | nd | nd | nd |
| n-Butyl | 4-FPh | H | 174.8 | nd | nd | nd |
| n-Butyl | dimethylphenyl | H | 72.125 | nd | nd | nd |
| Cyclopentyl | 4-biphenylyl | H | 14.9 | x | 1.568 | x |
| Hexyl | Ph | Me | 217.7 | nd | nd | nd |
| Hexyl | 4-NO$_2$Ph | H | 46.75 | x | nd | nd |
| Cyclohexyl | 4-ClPh | H | 43.79 | x | nd | nd |
| cyclohexyl | 4-MeSPh | H | 118 | nd | nd | nd |
| Cyclohexyl | 4-CNPh | H | 354.05 | nd | nd | nd |
| Cyclohexyl | 4-MeOPh | H | 111.84 | nd | nd | nd |
| Cyclohexyl | 4-ClPh | H | 35.64 | x | 4.936 | x |
| Ph | 4-BrPh | Me | 57.52 | nd | nd | nd |
| Bn | 4-Iph | H | 30.67 | x | nd | nd |
| Bn | 4-NO$_2$Ph | H | 221.95 | nd | nd | nd |

TABLE 14-continued

| | | | Salmonella Typhimurium ATCC14028 | | Pseudomonas aeruginosa PA14 | |
|---|---|---|---|---|---|---|
| R1 | R3 | R4 | IC50 biofilm inhibition (μM) | Influence on growth | IC50 biofilm inhibition (μM) | Influence on growth |
| Bn | 4-IPh | H | 26.895 | x | 8.609 | x |
| Bn | Ph | H | 209.3 | nd | nd | nd |
| 2-(3-MeOPh)Et | 3,4-diClPh | H | 7.3905 | x | nd | nd |
| 2-(3-MeOPh)Et | biphenylyl | H | 12.548 | o | nd | nd |
| 2-(3-MeOPh)Et | 4-NO2Ph | H | 123.95 | nd | nd | nd |
| 2-(3,4-diMeOPh)Et | 4-NO$_2$Ph | H | 126.9 | nd | nd | nd |
| p-MeO-Bn | 4-NO$_2$Ph | H | 219.5 | nd | nd | nd |
| p-MeO-Bn | 4-BrPh | H | 104.68 | nd | nd | nd |
| piperonyl | 4-FPh | H | 29.35 | o | nd | nd |
| piperonyl | 3,4-methylene-dioxy-Ph | H | 102.43 | nd | nd | nd |
| Cyclododecyl | 3-NO$_2$Ph | H | <6.25 | o | nd | nd |
| cyclododecyl | 4-NO$_2$Ph | H | <6.25 | o | 6.316 | o |
| tricyclo[3.3.1.13,7]dec-1-yl | 4-NO$_2$Ph | H | 8.801 | x | nd | nd |

[a] x means: no influence on the planktonic growth at the IC50 for biofilm inhibition
[b] nd means: not determined
[c] o means: planktonic growth is retarded at the IC50 for biofilm inhibition

EXAMPLE 6

Synthesis and Characterization of Substituted imidazo[1,2-a]pyrimidinium Perchlorate Salts The synthesis of substituted imidazo[1,2-a]pyrimidinium perchlorate salts was performed according to the scheme and experimental procedure below.

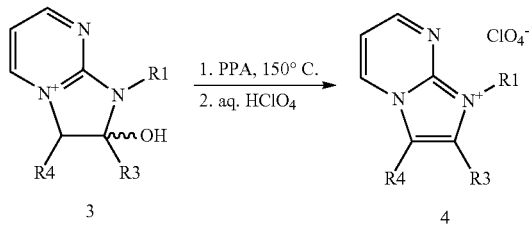

A mixture of 84% polyphosphoric acid (3 g) and a bromide salt 3 (3 mmole) was heated in 50 ml beaker upon intensive stirring at 150° C. for 15 minutes. After cooling to the room temperature the resulting viscous mass was dissolved in 30 ml of water and 1 ml (10 mmol) of 70% HClO$_4$ was added dropwise upon mild stifling. The resulting white precipitate was washed with distilled water (3×10 mL), ether (2×10 mL) until a neutral reaction of a pH paper, and then dried over P$_2$O$_5$ to afford the perchlorate salt 4 as fine white crystals in good yield.

Analytical data (proton and carbon nuclear magnetic resonance, and mass spectrum) of some perchlorate salts are listed below:

2-(4-Methoxyphenyl)-1-octylimidazo[1,2-a]pyrimidin-1-ium perchlorate $^1$H NMR (300 MHz, DMSO-d$_6$): δ=9.36 (m, 1H), 9.14 (m, 1H), 8.51 (s, 1H), 7.75 (m, 3H), 7.23 (d, J=8.2 Hz, 2H), 3.98 (s, 3H), 3.84 (t, J=7.5 Hz, 2H), 1.67 (m, 2H), 1.32 (m, 10H), 0.9 (t, J=7.5 Hz, 3H). $^{13}$C NMR (75.5 MHz, DMSO-d$_6$): δ= 161.6, 157.4, 143.1, 138.4, 137.8, 131.5 (×2), 117.5, 115.3 (×2), 114.7, 110.5, 55.9, 43.2, 31.4, 29.7, 29.0, 28.4, 26.7, 23.1, 14.3. MS (m/z) 225 [(M-ClO$_4$—Octyl)]$^+$.

2-(4-Fluorophenyl)-1-octylimidazo[1,2-a]pyrimidin-1-ium perchlorate $^1$H NMR (300 MHz, DMSO-d$_6$): δ=9.39 (m, 1H), 9.16 (m, 1H), 8.57 (s, 1H), 7.81 (m, 3H), 7.54 (t, J=8.2 Hz, 2H), 3.83 (t, J=7.5 Hz, 2H), 1.65 (m, 2H), 1.30 (m, 10H), 0.86 (t, J=7.5 Hz, 3H). $^{13}$C NMR (75.5 MHz, DMSO-d$_6$): δ=165.3, 162.2, 157.1, 143.2, 137.6, 136.9, 132.4 (×2), 122.1, 117.2, 116.7 (×2), 114.8, 111.3, 43.3, 31.7, 29.7, 29.1, 29.0, 26.6, 22.6, 14.1. MS (m/z) 213 [(M-ClO$_4$—Octyl)]$^+$.

2-(3,4-Dichlorophenyl)-1-octylimidazo[1,2-a]pyrimidin-1-ium perchlorate $^1$H NMR (300 MHz, DMSO-d$_6$): δ=9.41 (m, 1H), 9.18 (m, 1H), 8.60 (s, 1H), 7.98-7.65 (m, 4H), 3.81 (t, J=7.5 Hz, 2H), 1.69 (m, 2H), 1.33 (m, 10H), 0.91 (t, J=7.5 Hz, 3H). $^{13}$C NMR (75.5 MHz, DMSO-d$_6$): δ=158.2, 153.2, 151.8, 148.5, 148.3, 143.2, 138.7, 135.8, 122.9, 119.2, 115.0, 112.0, 43.4, 31.5, 29.2, 29.1, 29.0, 26.6, 22.6, 14.1. MS (m/z) 263 [(M-ClO$_4$—Octyl)]$^+$.

2-(3-Bromophenyl)-1-octylimidazo[1,2-a]pyrimidin-1-ium perchlorate $^1$H NMR (300 MHz, DMSO-d$_6$): δ=9.39 (m, 1H), 9.18 (m, 1H), 8.60 (s, 1H), 7.90 (m, 2H), 7.79 (m, 1H), 7.73 (m, 2H), 3.81 (t, J=7.5 Hz, 2H), 1.65 (m, 2H), 1.33 (m, 10H), 0.91 (t, J=7.5 Hz, 3H). $^{13}$C NMR (75.5 MHz, DMSO-d$_6$): δ=158.1, 143.2, 138.7, 136.8, 132.9, 131.9, 125.2, 124.8, 114.8, 111.4, 43.1, 31.5, 29.2, 29.0, 28.9, 26.4, 22.3, 14.2. MS (m/z) 273 [(M-ClO$_4$—Octyl)]$^+$.

2-(4-Methylthiophenyl)-1-octylimidazo[1,2-a]pyrimidin-1-ium perchlorate $^1$H NMR (300 MHz, DMSO-d$_6$): δ=9.36 (m, 1H), 9.14 (m, 1H), 8.56 (s, 1H), 7.77 (m, 1H), 7.75 (d, J=8.3 Hz, 2H), 7.54

(d, J=8.3 Hz, 2H), 3.99 (s, 3H), 2.58 (s, 3H). $^{13}$C NMR (75.5 MHz, DMSO-d$_6$): δ=157.6, 143.2, 142.9, 138.5, 137.6, 130.2 (×2), 126.3 (×2), 121.4, 112.5, 42.4, 31.0, 29.2, 29.0, 28.6, 26.7, 22.1, 14.5. MS (m/z) 241 [(M-ClO$_4$—Octyl)]$^+$.

EXAMPLE 7

Biofilm Formation Inhibiting Activity of Substituted imidazo[1,2-a]-pyrimidinium Bromide and Perchlorate Salts Evaluation of the biofilm inhibitory activity of some substituted imidazo[1,2-a]-pyrimidinium bromide and perchlorate salts produced according to examples 3 and 5 was carried out by growing up biofilms of *S. Typhimurium* ATCC14028 or SL1344 or *Pseudomonas aeruginosa* PA14 in the presence of different concentrations (1/2 dilution series) of biofilm inhibitors, by using the Calgary biofilm device. After an incubation period of 24 hours at 25° C. the biofilms were visualized by crystal violet staining. In the next step the stain was extracted from the biofilm with 30% acetic acid. The absorbance of the resolubilized stain at 570 nm was taken as a measure of the amount of biofilm formed. From these measurements the concentration of the test compound at which 50% biofilm inhibition was observed (IC$_{50}$ value) was calculated. The IC$_{50}$ values of representative imidazo[1,2-a]-pyrimidinium salts for anti-biofilm activity are shown in Table 15 wherein (1)IC50 refers to *S. Typhimurium* ATCC14028, and (2)IC50 refers to *P. aeruginosa* PA14, ND stands for "not determined", and wherein Ph stands for phenyl, n-hep stands for n-heptyl, c-hep stands for cycloheptyl, etc.

TABLE 15

| R1 | R2 | R3 | C2-C3 bound | X$^-$ | (1) IC50 (μM)$^a$ | (2) IC50 (μM) |
|---|---|---|---|---|---|---|
| n-Hexyl | OH | Ph | single | Br$^-$ | 102 | 3.13 |
| n-Hep | OH | Ph | single | Br$^-$ | 23.36 | 5.887 |
| n-Octyl | OH | Ph | single | Br$^-$ | 9.774 | 11.22 |
| n-Nonyl | OH | Ph | single | Br$^-$ | 8.255 | 4.852 |
| n-Decyl | OH | Ph | single | Br$^-$ | 15.01 | 3.946 |
| n-Und | OH | Ph | single | Br$^-$ | 24.61 | 28.63 |
| n-Dod | OH | Ph | single | Br$^-$ | 27.52 | 9.635 |
| n-Trd | OH | Ph | single | Br$^-$ | 81.64 | 17.04 |
| n-Tet | OH | Ph | single | Br$^-$ | 179.6 | NA$^c$ |
| c-Hep | OH | Ph | single | Br$^-$ | 84.15 | 5.811 |
| c-Octyl | OH | Ph | single | Br$^-$ | 58.36 | 4.629 |
| n-Hexyl | OH | 4-ClPh | single | Br$^-$ | 13.69 | 20.23 |
| n-Hep | OH | 4-ClPh | single | Br$^-$ | 6.667 | ~12.46 |
| n-Octyl | OH | 4-ClPh | single | Br$^-$ | 6.982 | 11.7 |
| n-Non | OH | 4-ClPh | single | Br$^-$ | 18.32 | 60.47 |
| n-Decyl | OH | 4-ClPh | single | Br$^-$ | 51.33 | 192.8 |
| n-Und | OH | 4-ClPh | single | Br$^-$ | 61.85 | 205 |
| n-Dod | OH | 4-ClPh | single | Br$^-$ | 122.1 | 119.2 |
| n-Trd | OH | 4-ClPh | single | Br$^-$ | 316.1 | 59 |
| c-Hep | OH | 4-ClPh | single | Br$^-$ | 27.87 | 63.77 |
| c-Octyl | OH | 4-ClPh | single | Br$^-$ | 12.62 | 15.55 |
| n-Hexyl | OH | 4-NO$_2$Ph | single | Br$^-$ | 54.69 | 10.86 |
| n-Octyl | OH | 4-NO$_2$Ph | single | Br$^-$ | 6.62 | 7.65 |
| n-Decyl | OH | 4-NO$_2$Ph | single | Br$^-$ | 9.946 | ND$^d$ |
| n-Octyl | OH | 4-FPh | single | Br$^-$ | 7.575 | 7.124 |
| n-Decyl | OH | 4-FPh | single | Br$^-$ | 20.01 | ND |
| n-Octyl | OH | 3,4-diClPh | single | Br$^-$ | 7.094 | ~12.29 |
| n-Decyl | OH | 3,4-diClPh | single | Br$^-$ | 32.4 | ND |
| n-Octyl | OH | 4-MeOPh | single | Br$^-$ | 10.53 | 13.57 |
| n-Decyl | OH | 4-MeOPh | single | Br$^-$ | 18.6 | ND |
| n-Octyl | OH | 4-MeSPh | single | Br$^-$ | ~13.21 | 29 |
| n-Decyl | OH | 4-MeSPh | single | Br$^-$ | 45.74 | ND |
| n-Oct | OH | 1-naptnyl | single | Br$^-$ | 14.72 | 16.66 |
| n-Dec | OH | 1-napthyl | single | Br$^-$ | 68.85 | ND |
| n-Octyl | OH | 4-(4'-NO$_2$Ph)Ph | single | Br$^-$ | 31.03 | 118.6 |
| n-Decyl | OH | 4-(4'-NO$_2$Ph)Ph | single | Br$^-$ | 200 | ND |
| n-Octyl | OH | 4-SO$_2$MePh | single | Br$^-$ | 60.29 | 11.46 |
| n-Decyl | OH | 4-SO$_2$MePh | single | Br$^-$ | 21.87 | ND |
| n-Octyl | OH | [1,1': 4',1"-terphenyl]-4-yl | single | Br$^-$ | ~52.81 | 26.76 |
| n-Octyl | OH | 3-BrPh | single | Br$^-$ | 7.133 | ~13.24 |
| n-Decyl | OH | 3-BrPh | single | Br$^-$ | 33.77 | ND |
| n-Decyl | OH | 4"-NO$_2$[1,1': 4',1"-terphenyl]-4-yl | single | Br$^-$ | 525.2 | ND |
| n-Octyl | NP$^b$ | 4-OMePh | double | ClO$_4^-$ | 34.75 | 8.732 |
| n-Octyl | NP | 4-FPh | double | ClO$_4^-$ | 35.67 | 19.51 |
| n-Octyl | NP | 3,4-diFPh | double | ClO$_4^-$ | 3.84 | 12.69 |
| n-Octyl | NP | 3-BrPh | double | ClO$_4^-$ | 7.332 | 6.996 |
| n-Octyl | NP | 1-napthalenyl | double | ClO$_4^-$ | ~6.600 | 6.835 |
| n-Octyl | NP | 4-(4'NO$_2$Ph)Ph | double | ClO$_4^-$ | 1.492 | 1.04 |
| n-Octyl | NP | 4-SO$_2$MePh | double | ClO$_4^-$ | 81.95 | 49.63 |
| n-Octyl | NP | 4-SMePh | double | ClO$_4^-$ | 20.65 | 9.295 |
| n-Octyl | NP | [1,1': 4',1"-terphenyl]-4-yl | double | ClO$_4^-$ | 5.031 | ND |

EXAMPLE 8
Biofilm Formation Inhibiting Activity of Substituted imidazo[1,2-a]-pyrimidinium Bromides We herein assayed the influence of some 2-hydroxy-2-phenyl-2,3-dihydro-imidazopyrimidinium bromides (compounds 1-50 in table 16) for their ability to prevent the biofilm formation of *S. Typhimurium* ATCC14028 and *P. aeruginosa* PA14 at 25° C. As shown in table 16 (wherein nd stands for "not determined"), these salts do reduce the biofilm formation to a certain extent.

TABLE 16

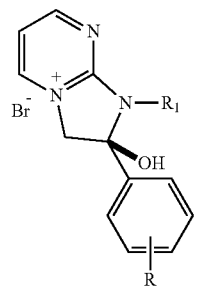

| Compound | R1 | R | *S. Typhimurium* IC50$^a$ (μM) | *P. aeruginosa* IC50 (μM) |
|---|---|---|---|---|
| 1 | Me | H | >800 | 211.8 |
| 2 | i-Pr | H | 540.5 | >400 |
| 3 | n-Bu | H | 409.5 | >400 |
| 4 | i-Bu | H | 131.2 | 289.4 |
| 5 | n-Pen | H | 278.2 | 565.4 |
| 6 | n-Hex | H | 102.0 | 405.8 |
| 7 | n-Hep | H | 23.4 | 24.8 |
| 8 | n-Oct | H | 9.8 | 18.9 |
| 9 | n-Non | H | 8.3 | 55.7 |
| 10 | n-Dec | H | 15.0 | 47.0 |
| 11 | n-Und | H | 24.6 | >800* |
| 12 | n-Dod | H | 27.5 | >800* |
| 13 | n-Trd | H | 81.6 | >800* |
| 14 | n-Tet | H | 179.6 | >800* |
| 15 | Me | 4-Cl | 225.0 | nd |
| 16 | n-Bu | 4-Cl | 29.7 | 24.9 |
| 17 | i-Bu | 4-Cl | 31.4 | 83.4 |
| 18 | n-Pen | 4-Cl | 32.6 | 163.9 |
| 19 | n-Hex | 4-Cl | 13.7 | 79.8 |
| 20 | n-Hep | 4-Cl | 6.7 | 36.9 |
| 21 | n-Oct | 4-Cl | 7.0 | 21.7 |
| 22 | n-Non | 4-Cl | 18.3 | 21.0 |
| 23 | n-Dec | 4-Cl | 51.3 | 66.4 |
| 24 | n-Und | 4-Cl | 61.9 | >800* |
| 25 | n-Dod | 4-Cl | 122.1 | >800 |
| 26 | n-Trd | 4-Cl | 316.1 | >800 |
| 27 | n-Tet | 4-Cl | >800 | >800 |
| 28 | Me | 4-NO$_2$ | 698.3 | nd |
| 29 | Et | 4-NO$_2$ | 578.8 | >800 |
| 30 | i-Pr | 4-NO$_2$ | 466.5 | 191.9 |
| 31 | n-Bu | 4-NO$_2$ | 292.8 | 145.2 |
| 32 | i-Bu | 4-NO$_2$ | 322.5 | 191.7 |
| 33 | t-Bu | 4-NO$_2$ | 211.1 | 41.5 |
| 34 | n-Hex | 4-NO$_2$ | 54.7 | 12.4 |
| 35 | n-Oct | 4-NO$_2$ | 6.6 | 19.7 |
| 36 | n-Dec | 4-NO$_2$ | 9.9 | 22.3 |
| 37 | Me | 4-F | >800 | nd |
| 38 | n-Bu | 4-F | 163.0 | nd |
| 39 | n-Oct | 4-F | 7.6 | 107.7 |
| 40 | n-Dec | 4-F | 20.0 | nd |
| 41 | n-Bu | 4-Br | 90.1 | nd |
| 42 | i-Bu | 4-Br | 5.2 | nd |
| 43 | n-Pen | 4-Br | 1.7 | nd |
| 44 | Me | 3-NO$_2$ | 563.8 | nd |
| 45 | n-Bu | 4-MeO | 314.4 | nd |
| 46 | n-Oct | 4-MeO | 10.5 | 90.2 |
| 47 | n-Dec | 4-MeO | 18.6 | nd |
| 48 | i-Bu | 3,4-diCl | 8.0 | nd |

TABLE 16-continued

| Compound | R1 | R | *S. Typhimurium* IC50$^a$ (μM) | *P. aeruginosa* IC50 (μM) |
|---|---|---|---|---|
| 49 | n-Oct | 3,4-diCl | 7.1 | 11.6 |
| 50 | n-Dec | 3,4-diCl | 32.4 | nd |

*Although IC50 > 800 μM, the compound inhibits biofilm formation to a certain extent, but the dose response curve reaches a steady state level of 25 to 45% biofilm inhibition starting from concentrations between 25 and 50 μM.

Since salts with a n-octyl chain substituted at the 1-position have the highest activity against *Salmonella* biofilms and also have a high activity against *Pseudomonas* biofilms, we decided to synthesize additional 1-octyl-2-hydroxy-2-phenyl-2,3-dihydro-imidazopyrimidinium salts 51-56 with more variation in the substitution pattern of the 2-phenyl ring. As depicted in Table 17 showing influence on biofilm formation of *S. Typhimurium* ATCC14028 and *P. aeruginosa* PA14 at 25° C., these compounds generally inhibit biofilm formation of *S. Typhimurium* at low concentrations.

TABLE 17

51 and 53-56

52

| Compound | R | *S. Typhimurium* IC50$^a$ (μM) | *P. aeruginosa* IC50 (μM) |
|---|---|---|---|
| 51 | 4-SMe | ~13.2 | 36.5 |
| 52 |  | 14.7 | 15.1 |
| 53 | 4-(4'-NO2Ph) | 31 | 215.2 |
| 54 | 4-SO2Me | 60.3 | 99.9 |
| 55 | 4-([1,1'-biphenylyl]-4-yl) | ~52.8 | 336.1 |
| 56 | 3-Br | 7.1 | 29 |

We also synthesized a series of 2-hydroxy-2-phenyl-2,3-dihydro-imidazo-pyrimidinium salts with a broad variety of cycloalkyl substituents at the 1-position, with lengths ranging from 3 to 12 carbon atoms (compounds 57-60 in Table 18) which do have a very strong effect against *Salmonella* biofilms and *Pseudomonas* biofilms at 25° C.

TABLE 18

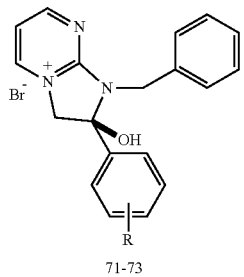

| Compound | R1 | R | S. Typhimurium IC50[a] (μM) | P. aeruginosa IC50 (μM) |
|---|---|---|---|---|
| 57 | c-Bu | H | 493.0 | >400 |
| 58 | c-Hex | H | 139.0 | 87.0 |
| 59 | c-Hep | H | 84.2 | 250.0 |
| 60 | c-Oct | H | 58.4 | 176.3 |
| 61 | c-Pr | 4-Cl | 82.7 | 179.2 |
| 62 | c-Bu | 4-Cl | 120.8 | 371.5 |
| 63 | c-Pen | 4-Cl | 41.8 | 162.8 |
| 64 | c-Hex | 4-Cl | 33.0 | 10.0 |
| 65 | c-Hep | 4-Cl | 27.9 | 76.2 |
| 66 | c-Oct | 4-Cl | 12.6 | 22.7 |
| 67 | c-Dod | 4-Cl | 5.6 | 6.8 |
| 68 | c-Pr | 4-NO$_2$ | 125.1 | nd[b] |
| 69 | c-Dod | 4-NO$_2$ | <6.3 | 6.9 |
| 70 | Adamantyl | 4-NO$_2$ | 8.8 | 14.4 |

Finally we synthesized an array of 2-hydroxy-2-phenyl-2,3-dihydro-imidazo-pyrimidinium salts, which are substituted at the 1-position with a benzyl (compounds 71-73), para-methoxybenzyl (compound 74), 3-methoxyphenethyl (compounds 75-78) or piperonyl (compounds 79-80) group (Table 19 showing influence on biofilm formation of *S. Typhimurium* ATCC14028 at 25° C.).

TABLE 19

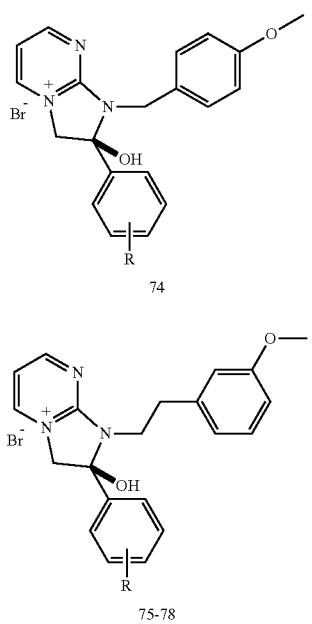

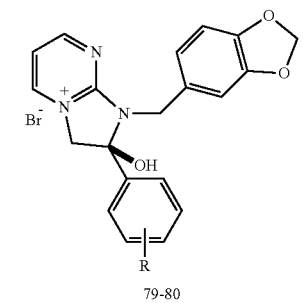

| | | | Effect on growth at:[b] | | | | | |
|---|---|---|---|---|---|---|---|---|
| Compound | R | IC50[a] (μM) | 400 μM | 50 μM | 40 μM | 25 μM | 10 μM | 5 μM |
| 71 | H | 211.9 | | | | | | |
| 72 | 4-NO$_2$ | 174.3 | | | | | | |
| 73 | 4-I | 36.66 | o | – | | | – | |
| 74 | 4-Br | 109.8 | | | | | | |
| 75 | 4-NO$_2$ | 123.5 | | | | | | |
| 76 | 4-F | 105.2 | | | | | | |
| 77 | 3,4-diCl | 7.229 | | | o | | | + |
| 78 | 4-([1,1'-biphenylyl]-4-yl) | 12.44 | | o | | o | o | |
| 79 | 4-F | 17.19 | o | – | | | – | |
| 80 | 3,4-MethylenedioxyPh | 53.73 | | | | | | |

EXAMPLE 9

Biofilm Formation Inhibiting Activity of Substituted 2-aminoimidazoles

We synthesized an array of 4(5)-phenyl-2-aminoimidazoles 2N-substituted with either a short n- or iso-alkyl chain (C1-C5) or a n-octyl chain. As depicted in table 20, a broad diversity of (substituted) 4(5)-phenyl groups were included such as phenyl (compounds 81-84), para-chlorophenyl (compounds 85-89), para-nitrophenyl (compounds 90-95), para-fluorophenyl (compounds 96-100), para-bromophenyl (compounds 101-105), para-methoxyphenyl (compounds 106-108), 3,4-dichlorophenyl (compounds 109-111), 3,4-difluorophenyl (compound 112), para-hydroxyphenyl (compound 113), naphtyl (compound 114), para-methylsulphonylphenyl (115-116) and meta-bromophenyl (117).

Table 20 shows the influence of 2N-alkylated 2-aminoimidazoles 81-117 on the biofilm formation and the planktonic growth of *S. Typhimurium* ATCC 14028 and *P. aeruginosa* PA14 at 25° C.

TABLE 20

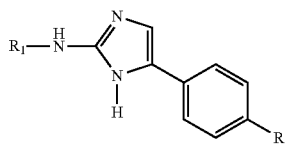

81-113 and
115-117

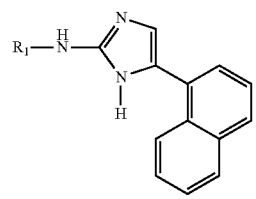

114

| Compound | R1 | R | S. Typhimurium IC50 (μM)[a] | 200 μM | 150 μM | 100 μM | 80 μM | 40 μM | 25 μM | 20 μM | 10 μM | 5 μM | P. aeruginosa IC50 (μM)[a] | 100 μM | 80 μM | 40 μM | 25 μM | 20 μM | 10 μM | 5 μM |
|---|---|---|---|---|---|---|---|---|---|---|---|---|---|---|---|---|---|---|---|---|
| 81 | H | H | 130.2 | | | − | | | − | | | | 72.6 | − | | | | | | |
| 82 | i-Pr | H | >800 | | | | | | | | | | 261.2 | | | | | | | |
| 83 | n-Bu | H | 25.3 | | | | | | | | | | 31.8 | | | | | | | |
| 84 | i-Bu | H | 4.9 | | | | | − | | − | | | 1.2 | | | | | | | |
| 85 | H | Cl | 16.0 | | | | | − | | | − | | 3.5 | | | | | | − | |
| 86 | i-Bu | Cl | 2.0 | | | | | + | | − | | | 0.9 | | | | | | | |
| 87 | n-Pen | Cl | >400 | | | | | | | | | | ~6.35* | | | | | | | |
| 88 | n-Oct | Cl | >400 | | | | | | | | | | ~1.6* | | | | | | | |
| 89 | n-Non | Cl | >800 | | | | | | | | | | nd[c] | | | | | | | |
| 90 | H | NO₂ | 17.6 | | | | | ○ | − | | − | | 34.5 | + | | − | | | | |
| 91 | Me | NO₂ | 170.4 | | | | | | | | | | 56.1 | | − | | | | | |
| 92 | Et | NO₂ | 171.3 | | | | | | | | | | 103.9 | | | | | | | |
| 93 | n-Bu | NO₂ | 701.5 | | | − | | | | | | | >800 | | | | | | | |
| 94 | i-Bu | NO₂ | 3.8 | | | | | − | | − | | | 22.9 | | | | | | − | |
| 95 | n-Oct | NO₂ | 10.9 | | | | − | − | | | − | | ~25.0* | | | | | | | |
| 96 | H | F | 84.4 | − | | | | − | | | | − | 15.0 | | − | | | | | |
| 97 | Me | F | 101.7 | | | | | | | | | | 25.2 | | | | | | | |
| 98 | n-Bu | F | 15.5 | | | | − | − | | | | | 10.8 | | − | | | | | |
| 99 | n-Hex | F | >400 | | | | | | | | | | ~12.5* | | | | | | | |
| 100 | n-Oct | F | >400 | | | | | | | | | | ~3.1* | | | | | | | |
| 101 | H | Br | 47.9 | | | − | | | | | − | | 3.2 | + | | | − | − | − | |
| 102 | n-Bu | Br | 7.1 | | | | | | | − | − | | 9.8 | | − | | | | | |
| 103 | i-Bu | Br | 2.9 | | | | | + | − | | | | 1.2 | | | | | | − | |
| 104 | n-Pen | Br | 3.1 | | | | | + | + | | − | | 10.2 | | − | | | | | |
| 105 | n-Oct | Br | 1.9 | | | | | | | | | | >800 | | | | | | | |
| 106 | H | 4-OMe | 119.7 | | | | | | | | | | 186.3 | | | | | | | |
| 107 | n-Bu | 4-OMe | 52.6 | | − | − | − | | | | | | 46.3 | | − | | | | | |
| 108 | n-Oct | 4-OMe | ~400* | | | | | | | | | | >800 | | | | | | | |
| 109 | Pr | 3,4-diCl | 10.9 | | | | | | − | − | | | 27.7 | | | | | | | |
| 110 | n-Pen | 3,4-diCl | 2.2 | | | | | ○ | + | | | | 0.7 | | | | | | − | |
| 111 | n-Oct | 3,4-diCl | 118.3* | | | | | | | | | | >800 | | | | | | | |
| 112 | Me | 3,4-diF | 601.9 | | | | | | | | | | nd | | | | | | | |

TABLE 20-continued

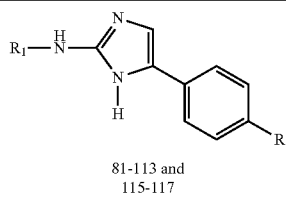

81-113 and
115-117

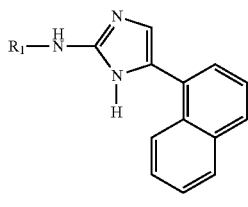

114

| | | | Effect on growth at:[b] | | | | | | | | | Effect on growth at:[b] | | | | | | |
|---|---|---|---|---|---|---|---|---|---|---|---|---|---|---|---|---|---|---|
| Compound | R1 | R | S. Typhimurium IC50 (μM)[a] | 200 μM | 150 μM | 100 μM | 80 μM | 40 μM | 25 μM | 20 μM | 10 μM | 5 μM | P. aeruginosa IC50 (μM)[a] | 100 μM | 80 μM | 40 μM | 25 μM | 20 μM | 10 μM | 5 μM |
| 113 | Me | 4-OH | 160.3 | | | | | | | | | | nd | | | | | | | |
| 114 | n-Oct | | 238.4* | | | | | | | | | | >800 | | | | | | | |
| 115 | H | 4-SO$_2$Me | >800 | | | | | | | | | | >800 | | | | | | | |
| 116 | n-Oct | 4-SO$_2$Me | 41.8 | | | | | – | – | | | | ~3.1* | | | | | – | | |
| 117 | n-Oct | 3-Br | 44.64 | | | | | – | – | | | | >800 | | | | | | | |

We also synthesized an array of 2-aminoimidazoles substituted at the 2N-position with cyclo-alkyl groups with intermediate length, i.e. cyclo-pentyl (compounds 117-121) and cyclo-hexyl (compounds 122-126). Table 21 below shows the Influence of 2N-cyclo-alkyl-2-aminoimidazoles 117-126 on the biofilm formation an the planktonic growth of S. Typhimurium ATCC14028 and P. aeruginosa PA14 at 25° C.

TABLE 21

| | | | Effect on growth at:[b] | | | | | Effect on growth at:[b] | | | | |
|---|---|---|---|---|---|---|---|---|---|---|---|---|
| Compound | R1 | R | S. Typhimurium IC50 (μM)[a] | 80 μM | 50 μM | 40 μM | 20 μM | 10 μM | P. aeruginosa IC50 (μM)[a] | 80 μM | 40 μM | 25 μM | 20 μM | 10 μM |
| 117 | c-Pen | H | 52.9 | – | | – | – | | 33.8 | – | | | | |
| 118 | c-Pen | 4-Cl | 4.4 | | | – | – | | 13.5 | – | | | | |
| 119 | c-Pen | 4-NO$_2$ | 11.8 | | | – | – | | 20.2 | | | – | | |
| 120 | c-Pen | 4-Br | 12.1 | | | – | – | | 7.2 | | | – | | |
| 121 | c-Pen | 3,4-diCl | 5.7 | | | – | – | | 7.9 | | | | – | |
| 122 | c-Hex | 4-Cl | >800 | | | | | | ~25* | | | | | |
| 123 | c-Hex | 4-NO$_2$ | 36.7 | | – | | | | ~25* | | | | | |
| 124 | c-Hex | 3-NO$_2$ | 629.5 | | | | | | 4.4 | | | | – | |
| 125 | c-Hex | 4-OMe | ~377.6 | | | | | | 54.8 | – | | | | |
| 126 | c-Hex | 4-SMe | 191.3 | | | | | | 15.8 | | | – | | |

Finally we synthesized an array of 4(5)-phenyl-2-aminoimidazoles, which are substituted at the 2N-position with a benzyl (compound 127), para-methoxybenzyl (compound 128), 3-methoxyphenethyl (compounds 129-131) or piperonyl group (compounds 132-133) which (Table 22) were tested against both Salmonella and Pseudomonas biofilm formation at 25° C.

TABLE 22
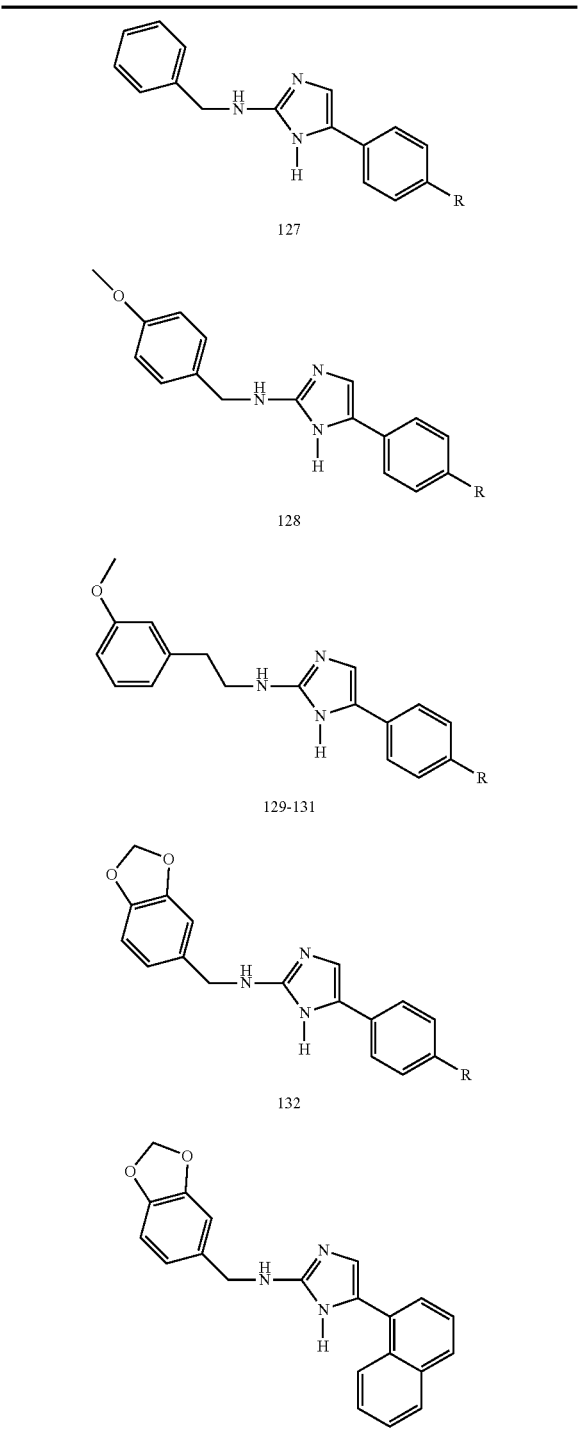
| Compound | R | S. Typhimurium IC50 (μM)[a] | Effect on growth at:[b] 80 | 40 | 20 | P. aeruginosa IC50 (μM)[a] |
|---|---|---|---|---|---|---|
| 127 | 4-Cl | 30.73 | | – | | 26.27 |
| 128 | 4-NO$_2$ | >800 | | | | >800 |
| 129 | 4-NO$_2$ | 19.07 | | | – | 3.704 |
| 130 | 3,4-diCl | >800 | | | | >800 |
| 131 | 4-([1,1'-biphenylyl]-4-yl) | >800 | | | | >800 |
TABLE 22-continued
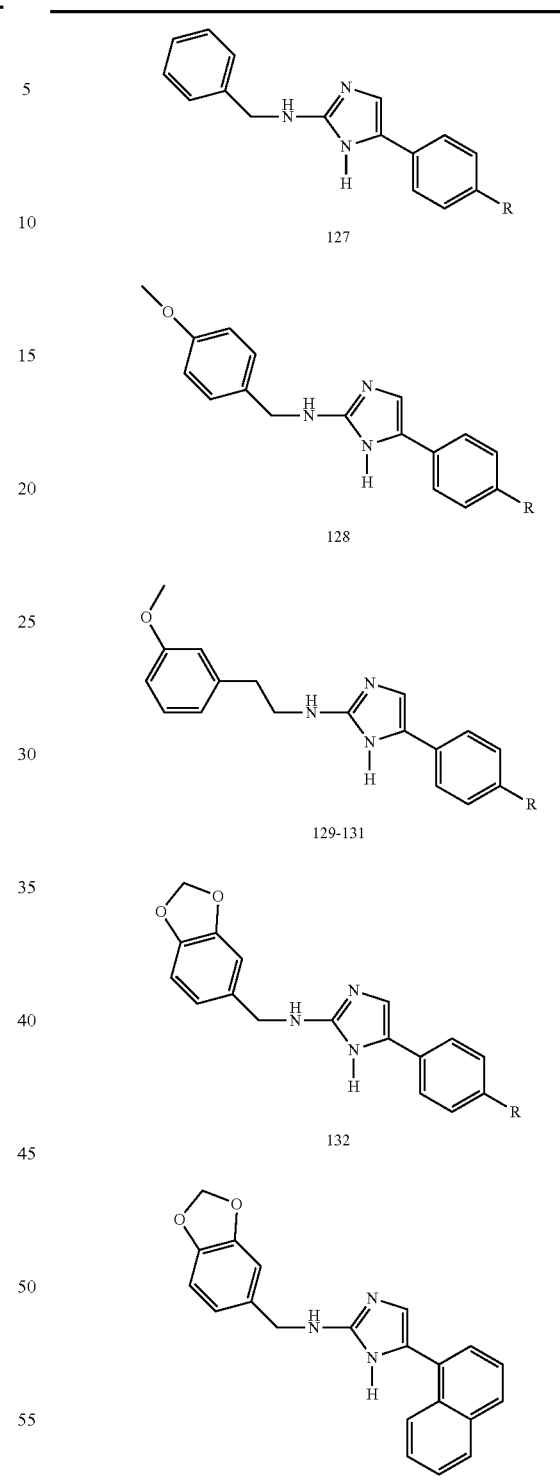
| Compound | R | S. Typhimurium IC50 (μM)[a] | Effect on growth at:[b] 80 | 40 | 20 | P. aeruginosa IC50 (μM)[a] |
|---|---|---|---|---|---|---|
| 132 | 4-F | 66.59 | | – | | 455.5 |
| 133 | | 261 | | | | 10.52 |

EXAMPLE 10

Synthesis of 2-Amino-1H-imidazole/Triazole Conjugates and Precursors Thereof This example provides the synthesis and characterization of 2-Amino-1H-imidazole/Triazole Conjugates according to the following structural formula

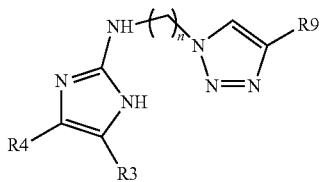

wherein R3, R4, R9 and n are as defined in table 26 below and which are capable of inhibiting biofilm formation.

TABLE 26

| R3 | R4 | R9 | n |
|---|---|---|---|
| Ph | H | Phenyl | 2 |
| Ph | H | phenyl | 3 |
| 4-BrPh | H | propyl | 2 |
| 4-BrPh | H | heptyl | 2 |
| 4-BrPh | H | c-propyl | 2 |
| 4-BrPh | H | c-hexyl | 2 |
| 4-BrPh | H | pMeOPh | 2 |
| 4-BrPh | H | propyl | 3 |
| 4-BrPh | H | C(CH$_3$)$_2$(NH$_2$) | 3 |
| 4-ClPh | H | butyl | 3 |
| 4-FPh | H | c-propyl | 2 |
| 4-FPh | H | c-pentyl | 2 |
| 4-FPh | H | butyl | 3 |
| 3,4-diClPh | H | propyl | 2 |
| 3,4-diClPh | H | butyl | 2 |
| 3,4-diClPh | H | pentyl | 2 |
| 3,4-diClPh | H | c-hexyl | 2 |
| 3,4-diClPh | H | propyl | 3 |
| 3,4-diClPh | H | butyl | 3 |
| 3,4-diClPh | H | c-hexyl | 3 |
| 3,4-diClPh | H | N-Me$_2$ | 3 |
| 3,4-diClPh | H | p(t-Bu)Ph | 3 |
| 3,4-diClPh | H | thiofuran | 3 |
| CHPh2 | H | Heptyl | 2 |
| CHPh2 | H | t-But | 2 |
| CHPh2 | H | O-Pen | 2 |
| naphtyl | H | Butyl | 2 |

TABLE 26-continued

| R3 | R4 | R9 | n |
|---|---|---|---|
| p-MeOPh | H | butyl | 3 |
| Ph | Ph | heptyl | 3 |
| p-ClPh | p-MePh | Pentyl | 2 |
| p-ClPh | p-MePh | c-Pentyl | 2 |

A microwave-assisted protocol was developed for the construction of 2-amino-1H-imidazole/triazole conjugates starting from the previously described 2-hydroxy-2,3-dihydro-1H-imidazo[1,2-a]pyrimidin-4-ium salts. The process involves a one-pot hydrazinolysis/Dimroth-rearrangement of these salts followed by a ligand-free copper

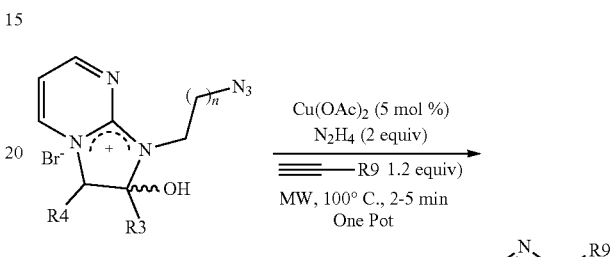

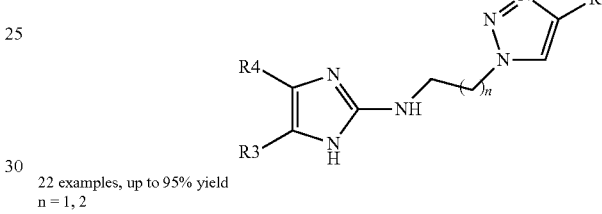

22 examples, up to 95% yield
n = 1, 2 nanoparticle-catalyzed azide-alkyne Huisgen cycloaddition.

Initially, a two-step synthesis procedure was developed (Scheme 1 below). A mixture of N-(3-azidopropyl)pyrimidin-2-amine (1a) and phenacylbromide (2a, R3=phenyl, R4=H) in MeCN was heated at 75° C. for 3 hours resulting in the formation of the 2-hydroxy-2,3-dihydro-1H-imidazo[1,2-a]pyrimidin-4-ium salt 3a. This salt smoothly underwent Dimroth-type rearrangement upon treatment with 7 equiv of hydrazine hydrate yielding N-(3-azidopropyl)-1H-imidazol-2-amine 4a. Subsequent CuAAC was performed upon treatment of 2-AI 4a with phenylacetylene (1.5 equiv) and CuI (10 mol %) as catalyst under microwave irradiation at a ceiling temperature of 100° C. and a maximum power of 40 W for 10 minutes, delivering the desired 2-AIT 5a (R3, R9=Ph; R$^4$=H; n=2) in 70% yield.

Scheme 1

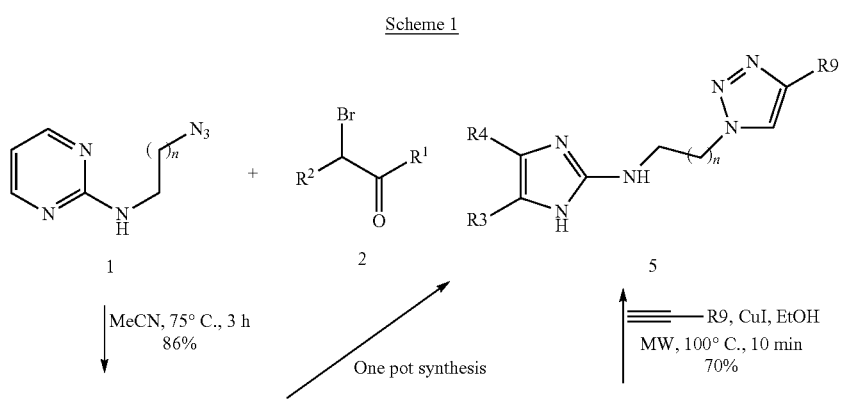

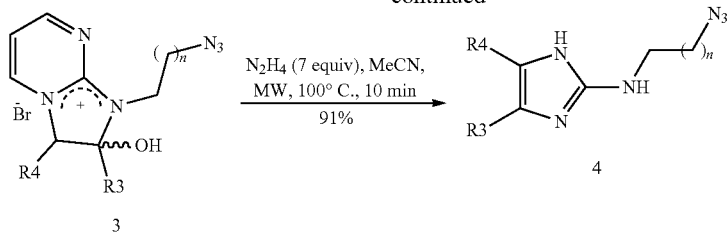

3a-5a: R3, R4 = Ph; R9 = H; n = 2

Because the required copper(0) nanocatalyst can be generated in situ upon reduction of the Cu(II) salt by hydrazine, the Dimroth rearrangement and the CuAAC can be run in a one-pot fashion. The latter procedure was evaluated employing hydroxy salt 3a (R3=phenyl, R4=H) and phenylacetylene as a model system (Table 22A). To our satisfaction the one-pot reaction worked well when 2 equivalents of hydrazine hydrate in combination with 10 mol % Cu(OAc)$_2$ were employed upon microwave irradiation at a ceiling temperature of 100° C. for 20 minutes (Table 22A, entry 3). When only 1 equivalent of hydrazine hydrate was used the product was obtained in a moderate yield of 51% (Table 22A, entry 1) while increasing the amount of hydrazine hydrate did not influence the yield (Table 22A, entry 2). The reaction time could be decreased to a mere 2 minutes while a further shortening resulted in an incomplete Dimroth rearrangement reaction (Table 22A, entries 3-7). Also lowering the reaction temperature to 90° C. resulted in a decreased yield (Table 22A, entry 9). Replacement of Cu(OAc)$_2$ with CuSO$_4$ gave the product in 67% yield (Table 22A, entry 11), while with Cu-powder (200 mesh) only trace amounts of the desired compound were observed (Table 22A, entry 13). As expected no product was formed in the absence of catalyst (Table 22A, entry 12). The optimal reaction conditions were achieved when a mixture of hydroxy salt 3a (0.25 mmol), hydrazine hydrate (2 equivalents), phenyl acetylene (1.5 equivalents), Cu(OAc)$_2$ (5 mol %) in EtOH/H$_2$O (4:1; 1 mL) was irradiated for 2 minutes at a ceiling temperature of 100° C. applying a maximum power of 35 W. The desired compound 5a was isolated in 90% yield (Table 22A, entry 8). When the reaction was performed at room temperature for 24 hours, the product 5a was obtained in very low yield (Table 22A, entry 14).

TABLE 22A

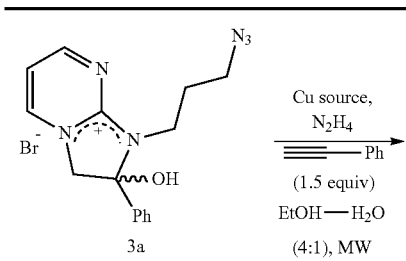

TABLE 22A-continued

| Entry | Time min | Temp. (° C.) | Cu source, mol % | Yield (%)[b] |
|---|---|---|---|---|
| 1[c] | 20 | 100° C. | Cu(OAc)$_2$, 10 | 51 |
| 2[d] | 20 | 100° C. | Cu(OAc)$_2$, 10 | 84 |
| 3 | 20 | 100° C. | Cu(OAc)$_2$, 10 | 86 |
| 4 | 10 | 100° C. | Cu(OAc)$_2$, 10 | 80 |
| 5 | 5 | 100° C. | Cu(OAc)$_2$, 10 | 90 |
| 6 | 2 | 100° C. | Cu(OAc)$_2$, 10 | 90 |
| 7 | 1 | 100° C. | Cu(OAc)$_2$, 10 | 53 |
| 8 | 2 | 100° C. | Cu(OAc)$_2$, 5 | 90 |
| 9 | 2 | 90° C. | Cu(OAc)$_2$, 5 | 73 |
| 10 | 2 | 100° C. | Cu(OAc)$_2$, 2 | 57 |
| 11 | 2 | 100° C. | CuSO$_4$•5H$_2$O, 5 | 67 |
| 12 | 2 | 100° C. | — | — |
| 13 | 2 | 100° C. | Cu-powder, 10 | traces |
| 14 | 24 h | rt | Cu(OAc)$_2$, 5 | 24 |

[a] All reactions were conducted on a 0.25 mmol scale of 3a, applying hydrazine hydrate (2 equiv), phenylacetylene (1.5 equivalents) in EtOH/H$_2$O (4:1, 1 mL) under microwave irradiation; the mixture was irradiated in a sealed tube at the indicated ceiling temperature and 35 W maximum power for the stipulated time;
[b] isolated yields;
[c] 1.0 equivalent of hydrazine hydrate was used;
[d] 5.0 equivalents of hydrazine hydrate were used.

Scope of the Synthesis Protocol.

First, an array of hydroxy salts was prepared using our optimized conditions (Table 23). A special emphasis was made on the use of α-bromoketones bearing halogenated phenyl substituents because of their antibiofilm activity. In most cases, the reactions were run for 3 hours in MeCN at 75° C. affording the hydroxy salts 3b-l in good to excellent yields as white precipitates.

TABLE 23

| Entry | Compounds | R3 | R4 | n | R9 | Yield (%), 3 | Yield (%), 5 |
|---|---|---|---|---|---|---|---|
| 1 | 3b, 5b | 4-BrPh | H | 1 | 4-MeOPh | 90 | 66 |
| 2 | 3c, 5c | Ph | H | 1 | Ph | 89 | 84 |
| 3 | 3b, 5d | 4-BrPh | H | 1 | 4-MePh | 90 | 73 |
| 4 | 3d, 5e | naphth-2-yl | H | 1 | 4-BuPh | 69 | 64 |
| 5 | 3b, 5f | 4-BrPh | H | 1 | heptyl | 90 | 73 |
| 6 | 3e, 5g | 4-BrPh | H | 2 | 4-pentylPh | 83 | 80 |
| 7 | 3f, 5h | 3,4diClPh | H | 1 | 4-hexylPh | 75 | 84 |
| 8 | 3g, 5i | 3,4diClPh | H | 2 | N-methyl-methanamine | 77 | 81 |
| 9 | 3e, 5j | 4-BrPh | H | 2 | propan-2-amine | 83 | 75 |
| 10 | 3f, 5k | 3,4-diClPh | H | 1 | cyclohexyl | 75 | 89 |
| 11 | 3f, 5l | 3,4-diClPh | H | 1 | Pr | 75 | 85 |
| 12 | 3g, 5m | 3,4-diClPh | H | 2 | Pr | 77 | 91 |
| 13 | 3b, 5n | 4-BrPh | H | 1 | Pr | 90 | 94 |
| 14 | 3e, 5o | 4-BrPh | H | 2 | Pr | 83 | 75 |
| 15 | 3h, 5p | morpholino-methanone | H | 2 | Pr | 65 | 45 |
| 16 | 3i, 5q | morpholino-methanone | H | 1 | Pr | 76 | 39 |
| 17 | 3j, 5r | 4-FPh | H | 1 | cyclopentylmethyl | 69 | 68 |
| 18 | 3j, 5s | 4-FPh | H | 1 | cyclopropyl | 69 | 80 |
| 19 | 3k, 5t | 4-ClPh | 4-MePh | 1 | cyclopentyl | 72 | 56 |
| 20 | 3g, 5u | 3,4-diClPh | H | 2 | 4-tertBuPh | 77 | 85 |
| 21 | 3g, 5v | 3,4-diClPh | H | 2 | thiophen-3-yl | 77 | 91 |
| 22 | 3b, 5w | 4-BrPh | H | 1 | cyclopropyl | 90 | 80 |
| 23 | 3b, 5x | 4-BrPh | H | 1 | cyclohexyl | 90 | 71 |
| 24 | 3l, 5y | Ph | Ph | 2 | heptyl | 75 | 84 |

[a]All reactions were conducted on a 0.25 mmole scale of 3b-k, applying hydrazine hydrate (2 equiv), acetylene (1.5 equivalents), Cu(OAc)$_2$ (5 mol %) in EtOH/H$_2$O (4:1) (1 mL); the mixture was irradiated in a sealed tube at a ceiling temperature of 100° C. and 35 W maximum power for 2 minutes;
[b]isolated yields.

Thus prepared hydroxy salts 3b-1 (n=1, 2) were reacted with different (hetero)aromatic and alkyl acetylenes (Table 23). All reactions were completed within 2 minutes delivering the desired compounds in good to excellent yields. However, in case of morpholylamide substituent (Table 23, entry 15-16), probably due to hydrazinolysis of the starting hydroxy salt 3h and 3i, lower yields were observed. Remarkably, 4,5-disubstituted hydroxy salts 3k and 3i were successfully reacted, giving the desired products in 56 and 84% yield. Generally, the cycloaddition reaction proceeded efficiently with aliphatic and aromatic terminal acetylenes providing the corresponding 2-AIT 5 in good yields. Thus, a variety of substituted 2-AIT bearing an aromatic (Table 23, entry 1-4, 6, 7, 20), aliphatic (Table 23, entries 5, 8, 9, 11-16, 24), cyclic (Table 23, entries 10, 17-19, 22, 23) or heterocyclic (Table 23, entry 21) substituent at the C-4 position of the triazole ring were obtained.

Experimental Procedures and Compound Characterization

1. General Procedure for the Preparation of N-(3-azidopropyl)pyrimidin-2-amines 1

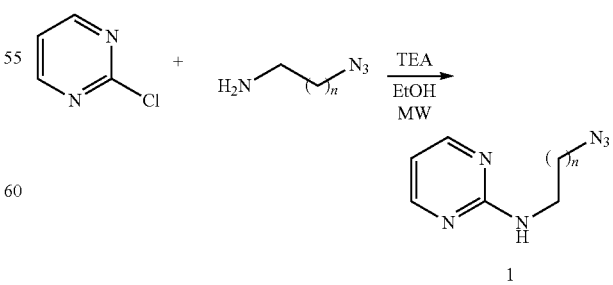

In a 50 mL microwave vial were successively dissolved in EtOH (20 mL) 2-chloropyrimidine (3.43 g, 30 mmol), azidoalkylamine (48 mmol, 1.6 equivalents) and triethylamine (6.2 mL, 45 mmol, 1.5 equivalents). The reaction tube was sealed, and irradiated in the cavity of a Milestone MicroSYNTH microwave reactor at a ceiling temperature of 120° C. at 100 W maximum power for 30 minutes. After the reaction mixture was cooled with an air flow for 15 minutes, it was diluted with water (100 mL), extracted with DCM (2×150 mL) and dried over Na$_2$SO$_4$. The solvent was evaporated in vaccuo, and the crude mixture was purified by silica gel flash chromatography using 0-5% MeOH-DCM as the eluent.

Using this procedure, the following compounds were prepared and characterized:

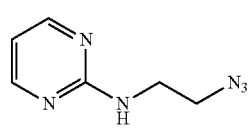 [SMILES: [N-]=[N+]=NCCNc1ncccn1]

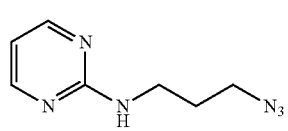 [SMILES: [N-]=[N+]=NCCCNc1ncccn1]

2. General Procedure for the Preparation of Hydroxy Salts 3a-1

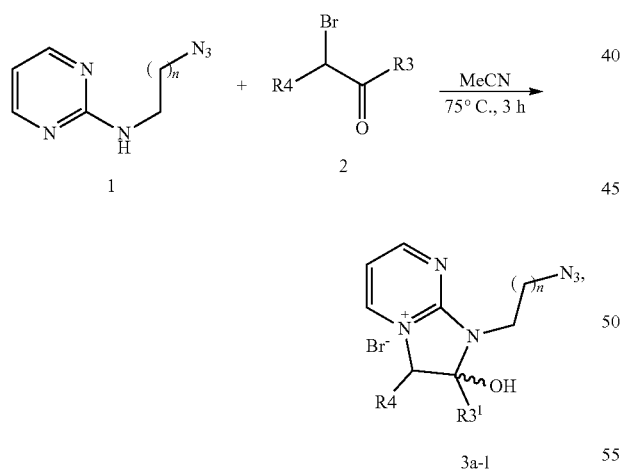

To a solution of N-(azidoalkyl)pyrimidin-2-amine 1 (6 mmol) and α-bromoacetophenone 2 (7.2 mmol, 1.2 equiv) in acetonitrile (12 mL) was added 4-dimethylaminopyridine (6 mg, 0.05 mmol). After being stirred at 75° C. for 3 h, the reaction mixture was diluted with ether (20 mL) and the precipitate was filtered off and washed with acetone (2×20 mL), ether (2×20 mL) and dried over P2O5 to give salt 3 as a white solid.

Using this procedure, the following compounds were obtained:

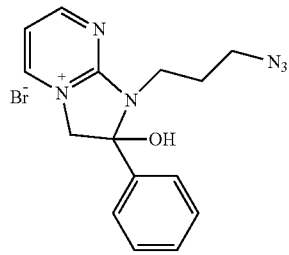

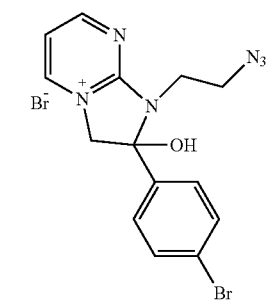

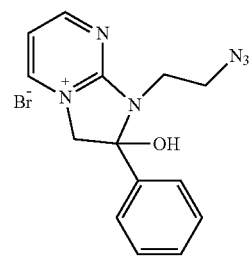

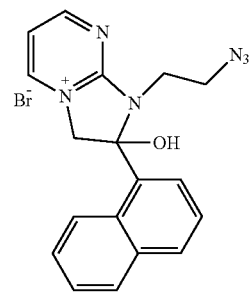

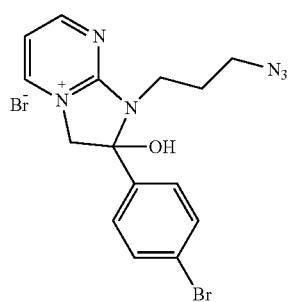

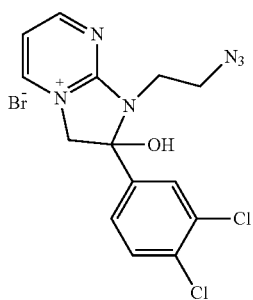

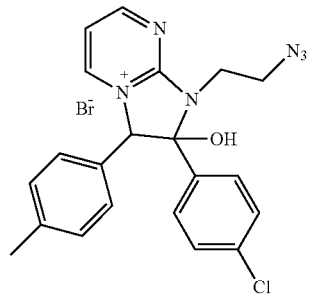

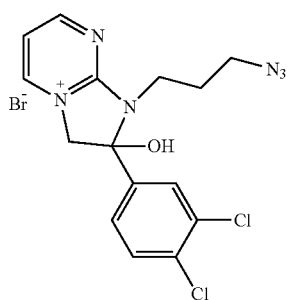

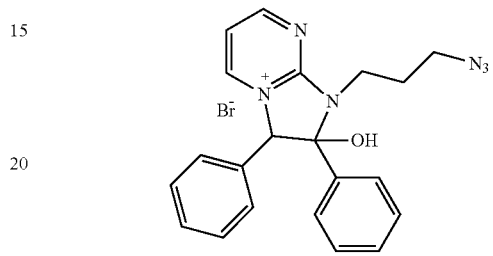

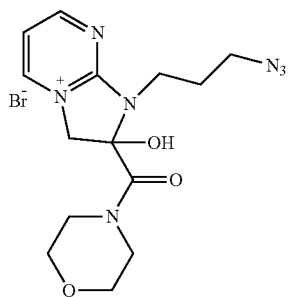

3. General Procedure for the Preparation of 2-AIT

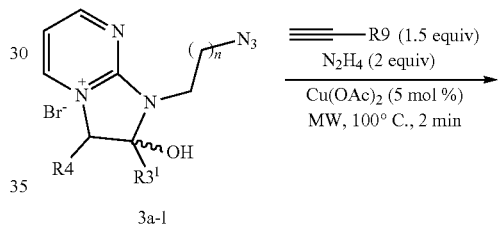

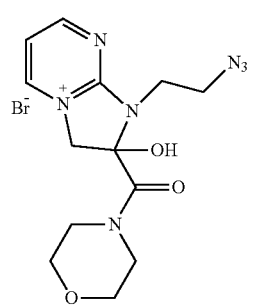

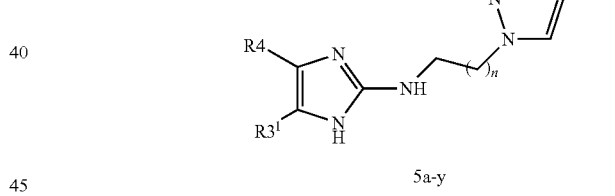

To the cooled solution of hydrazine hydride (2 equiv) in ethanol (0.8 mL) were added Cu(OAc)$_2$ (5 mol %) in water (0.2 mL) and stirred for 2 min at 0° C. To suspension were added acetylene (1.5 equiv) and hydroxyl salt 3 (1 equiv). The reaction mixture was irradiated at 100° C. at the maximum power 35 W for 2 min. After completion of the reaction, the solvent was removed under reduce pressure. The crude product was purified by column chromatography over silica gel using DCM/methanol/7N methanolic NH$_3$ (96:3:1) as the eluent.

Using this procedure, the following compounds were obtained:

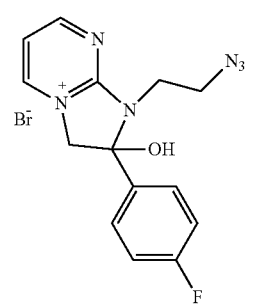

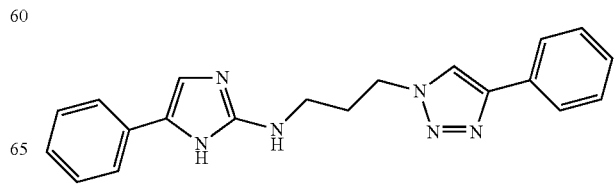

73
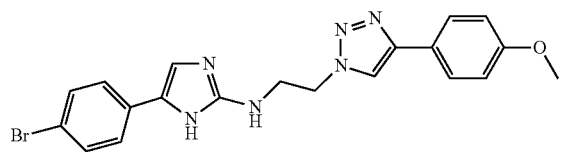 [SMILES: COc1ccc(-c2cn(CCNc3ncc(-c4ccc(Br)cc4)[nH]3)nn2)cc1]
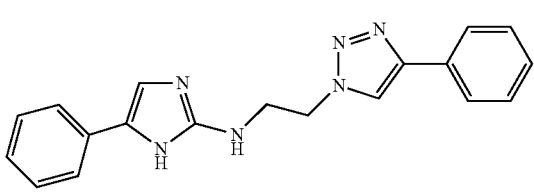 [SMILES: c1ccc(-c2cn(CCNc3ncc(-c4ccccc4)[nH]3)nn2)cc1]
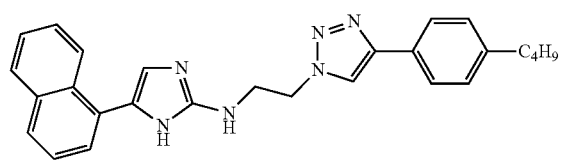
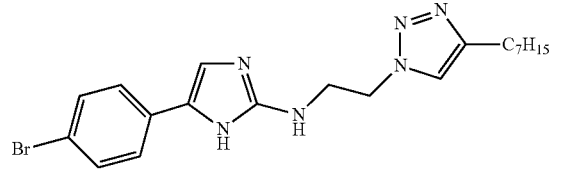
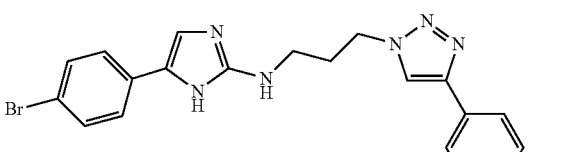
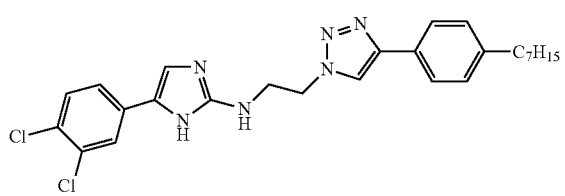
74
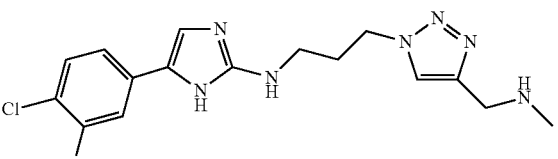
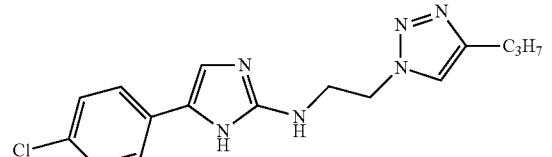
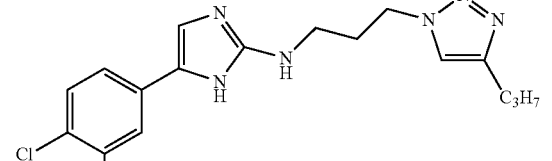
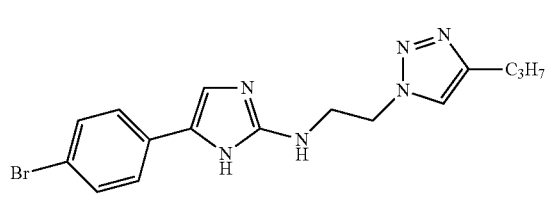

75

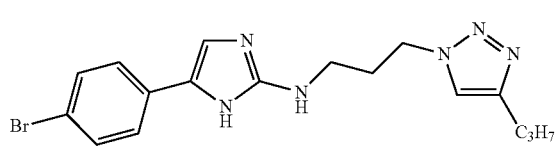

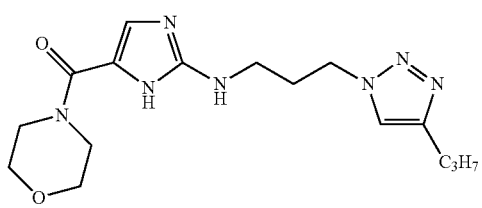

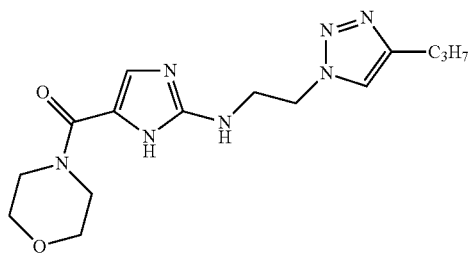

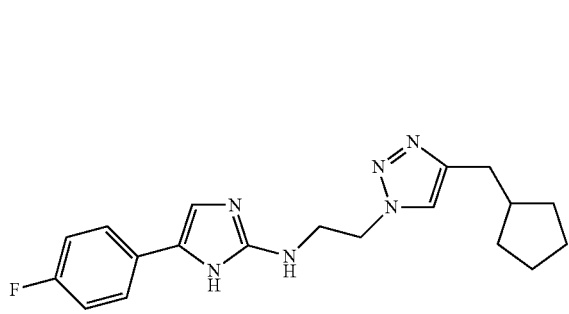 [SMILES: Fc1ccc(-c2cnc(NCCn3cc(CC4CCCC4)nn3)[nH]2)cc1]

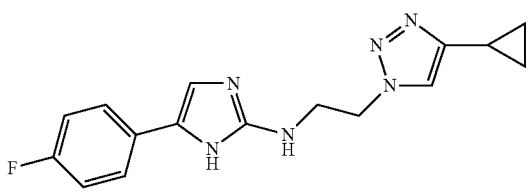 [SMILES: Fc1ccc(-c2cnc(NCCn3cc(C4CC4)nn3)[nH]2)cc1]

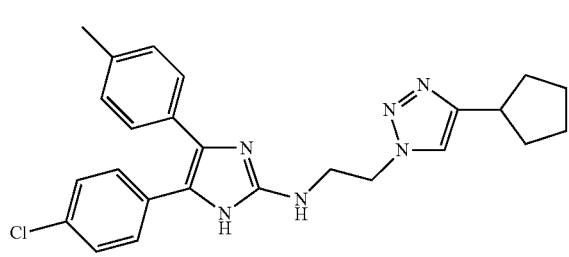 [SMILES: Cc1ccc(-c2nc(NCCn3cc(C4CCCC4)nn3)[nH]c2-c2ccc(Cl)cc2)cc1]

76

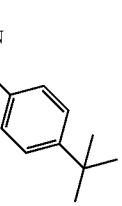

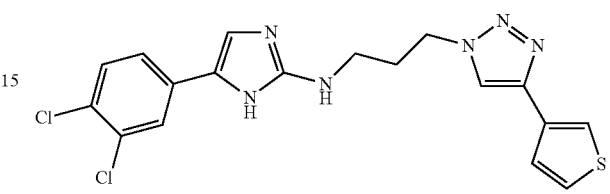

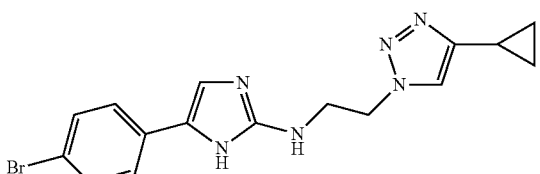

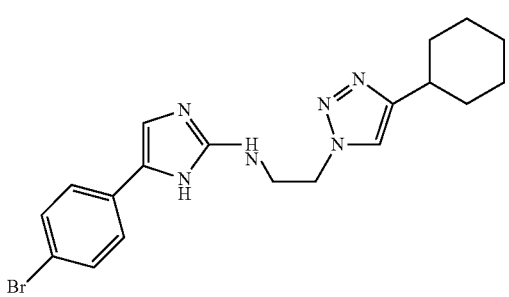 [SMILES: Brc1ccc(-c2cnc(NCCn3cc(C4CCCCC4)nn3)[nH]2)cc1]

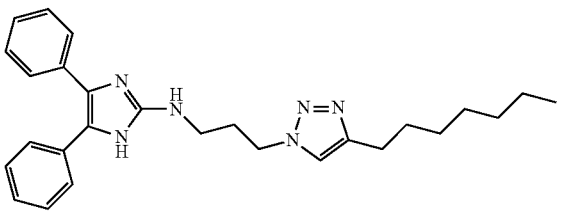 [SMILES: CCCCCCCc1cn(CCCNc2nc(-c3ccccc3)c(-c3ccccc3)[nH]2)nn1]

EXAMPLE 11

Anti-Bacterial Activity of
2-Amino-1H-imidazole/Triazole Conjugates

Evaluation of antibacterial-inhibitory and antibiofilm activity of some substituted 2-Amino-1H-imidazole/Triazole Conjugates of the invention was carried out as described above. The $IC_{50}$ values of representative compounds for anti-biofilm activity against a number of bacterial biofilms are shown in the following Tables 24 and 25.

TABLE 24

Preventive activity against S. typhimurium biofilms at 25° C.

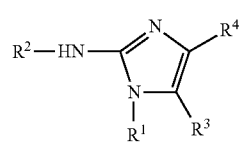

| R3 | R4 | R9 | n | IC(50) (μM) | CODE |
|---|---|---|---|---|---|
| Ph | H | Phenyl | 2 | 36.5 | |
| Ph | H | phenyl | 3 | 40.0 | |
| 4-BrPh | H | propyl | 2 | 25.3 | |
| 4-BrPh | H | heptyl | 2 | 188.8 | |
| 4-BrPh | H | c-propyl | 2 | 2.02 | |
| 4-BrPh | H | c-hexyl | 2 | 8.4 | |
| 4-BrPh | H | p-MePh | 2 | >800 | |
| 4-BrPh | H | pMeOPh | 2 | 91.2 | |
| 4-BrPh | H | propyl | 3 | 35.3 | |
| 4-BrPh | H | p-PenPh | 3 | >800 | |
| 4-BrPh | H | C(CH3)2(NH2) | 3 | 30.9 | |
| 4-ClPh | H | butyl | 3 | 23.9 | TR-57 |
| 4-FPh | H | c-propyl | 2 | 93.3 | |
| 4-FPh | H | c-pentyl | 2 | 128.3 | |
| 4-FPh | H | butyl | 3 | 186.9 | TR-64 |
| 3,4-diClPh | H | propyl | 2 | 35.6 | |
| 3,4-diClPh | H | butyl | 2 | 28.1 | LN-13 |
| 3,4-diClPh | H | pentyl | 2 | 9.67 | LN-16 |
| 3,4-diClPh | H | c-hexyl | 2 | 55.2 | |
| 3,4-diClPh | H | p-MeOPh | 2 | >800 | |
| 3,4-diClPh | H | propyl | 3 | 31.8 | |
| 3,4-diClPh | H | butyl | 3 | 41.5 | LN-15 |
| 3,4-diClPh | H | c-hexyl | 3 | 26.8 | |
| 3,4-diClPh | H | N-Me | 3 | 10.8 | |
| 3,4-diClPh | H | p(t-Bu)Ph | 3 | 17.8 | |
| 3,4-diClPh | H | thiofuran | 3 | 2.0 | |
| CHPh2 | H | Heptyl | 2 | 31.9 | LN-20 |
| CHPh2 | H | t-Butyl | 2 | 30.9 | |
| CHPh2 | H | O-Pen | 2 | 8.4 | |
| naphtyl | H | Butyl | 2 | 137.2 | TR-65 |
| p-MeOPh | H | butyl | 3 | 114.5 | LN-14 |
| Ph | Ph | heptyl | 3 | 10.8 | TR-66 |
| p-ClPh | p-MePh | Pentyl | 2 | 371.4 | |
| p-ClPh | p-MePh | c-Pentyl | 2 | 6.5 | |

TABLE 25

Preventive activity against Pseudomonas aeruginosa, Escherichia coli and Staphylococcus aureus biofilms at 25° C.

| Code | IC50 (μM) (vs P. aeruginosa) | IC50 (μM) (vs E. coli) | IC50 (μM) (vs S. aureus) |
|---|---|---|---|
| TR-57 | >400 | 12.2 | 87.2 |
| TR-64 | >400 | >800 | 304 |
| LN-13 | >400 | 6.8 | 50 |
| LN-14 | 44.6 | 71.0 | 150 |
| LN-15 | >400 | 10.3 | 45.7 |
| TR-65 | >400 | 52.7 | >800 |
| LN-16 | >400 | 13.2 | 36.7 |
| TR-66 | >400 | 8.7 | 21.6 |
| LN-20 | >400 | 40.2 | 51.9 |

(end of Table 25)

OTHER EMBODIMENTS

All publications, patents, and patent application publications mentioned herein are hereby incorporated by reference. Various modifications and variations of the described compounds of the invention will be apparent to those skilled in the art without departing from the scope and spirit of the invention. Although the invention has been described in connection with certain embodiments, it should be understood that the invention as claimed should not be unduly limited to such embodiments. Indeed, various modifications of the described modes for carrying out the invention that are obvious to those skilled in the relevant art are intended to be within the scope of the invention.

What is claimed is:
1. A compound selected from the group consisting of:
substituted 2-aminoimidazoles represented by the structural formula (I),

$$R^2-HN-\underset{R^1}{\overset{N}{\underset{|}{\bigcirc}}}\overset{R^4}{\underset{R^3}{}} \quad (I)$$

wherein $R^1$ is selected from the group consisting of hydrogen, $C_{2-15}$ alkyl, $C_{2-20}$ alkenyl, $C_{2-20}$ alkynyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cyclolkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkyl, $C_{1-20}$ alkoxy, halo $C_{1-20}$ alkoxy, amino, sulfhydryl, oxo, $C_{1-20}$ alkylthio and nitro, with the proviso that when $R^1$ is methyl, said methyl is not di- or tri-substituted with one phenyl and one or two further alkyl, aryl or heterocyclic substituents;

$R^2$ is selected from the group consisting of methyl, ethyl, cyclopropyl, isopropyl, propyl, butyl, isobutyl, tert-butyl, cyclopentyl, pentyl, cyclohexyl, hexyl, octyl, nonyl, cyclododecyl, 2-(3-methoxyphenyl)ethyl, benzyl, 4-methoxybenzyl, 3-methoxybenzyl, 1,3-benzodioxol-5-ylmethyl, methoxyethyl, homoveratryl, piperonyl, 2-[(4-fluorophenyl)thio]-phenyl-methyl, 2-[(2-fluorophenyl)thio]-phenyl-methyl, 2-(1-naphthylthio)phenyl]methyl and 2-(1,3-benzodioxol-5-ylthio)phenyl]methyl;

$R^3$ is selected from the group consisting of aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, phenyl, methylsulfonyl, amino, sulfhydryl, oxo, $C_{1-20}$ alkylthio and nitro;

$R^4$ is selected from the group consisting of hydrogen, $C_{1-20}$ alkyl, $C_{3-12}$ cycloalkyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, halo $C_{1-20}$ alkyl, $C_{1-20}$ alkoxy, halo $C_{1-20}$ alkoxy, amino, sulfhydryl, oxo, $C_{1-20}$ alkylthio and nitro;

with the proviso that said substituted 2-aminoimidazole is not one defined by the substituting pattern ($R^1$, $R^2$, $R^3$, $R^4$) of the following table

| R1 | R2 | R3 | R4 |
|---|---|---|---|
| H | Ethyl | CONH-ethyl | H |
| H | Cyclopropyl | Morpholin-4-ylcarbonyl | H |
| H | Cyclohexyl | 3-nitrophenyl | H |
| H | Cyclododecyl | 3-nitrophenyl | H |
| H | 4-methoxybenzyl | 4-nitrophenyl | H |
| H | Piperonyl | 4-fluorophenyl | H |
| H | Hexyl | Phenyl | Methyl |
| H | Methoxyethyl | 4-fluorophenyl | Methyl |
| H | Homoveratryl | 4-chlorophenyl | Phenyl |
| H | Tert-butyl | 4-chlorophenyl | 4-tolyl |
| H | methyl | 4-nitrophenyl | H |
| H | benzyl | 4-chlorophenyl | H | and
imidazo[1,2-a]pyrimidinium salts represented by the structural formula (II)

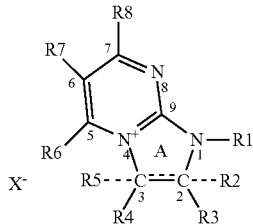

(II)

wherein ... at $C_2$-$C_3$ represents an optional double bond, in which case R2 and R5 are absent, so that either ring A is an imidazolinyl structure represented by formula B

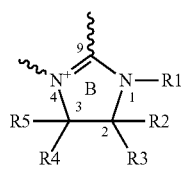

or ring A is an imidazolyl structure represented by formula C

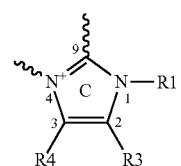

and wherein
R1, R4 and R5 are each independently selected from the group consisting of hydrogen, $C_{1-20}$ alkyl, $C_{2-20}$ alkenyl, $C_{2-20}$ alkynyl, $C_{1-20}$ alkylcarbonyl, $C_{3-12}$ cycloalkyl, $C_{3-12}$ cycloalkenyl, aryl, heterocyclic and heteroaryl, wherein each of said $C_{1-20}$ alkyl, $C_{2-20}$ alkenyl, $C_{2-20}$ alkynyl, $C_{3-12}$ cycloalkyl or $C_{3-12}$ cycloalkenyl may be substituted with one or more substituents independently selected from the group consisting of halogen, hydroxy, acetyl, aryl, heterocyclic, heteroaryl, $C_{1-20}$ alkoxy, amino, azido, sulfhydryl, oxo, $C_{1-20}$ alkylthio and nitro, and wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R2 is hydroxy,

R3 is selected from the group consisting of hydrogen, aryl, heterocyclic, heteroaryl, $C_{1-20}$ alkylaminocarbonyl and heterocyclylcarbonyl, wherein each of said aryl, heterocyclic and heteroaryl may be substituted with one or more substituents independently selected from the group consisting of halogen, hydroxy, acetyl, $C_{1-20}$ alkyl, $C_{1-20}$ alkoxy, amino, sulfhydryl, oxo, $C_{1-20}$ alkylthio and nitro;

R6, R7, R8 are each independently selected from the group consisting of hydrogen, hydroxy, halogen, amino, $C_{1-20}$ alkoxy, $C_{1-20}$ alkyl, $C_{2-20}$ alkenyl, $C_{3-12}$ cycloalkyl and $C_{3-12}$ cycloalkenyl; and $X^-$ is an anion, with the proviso that said imidazo[1,2-a]pyrimidinium salt is not one wherein R5, R6, R7 and R8 are each hydrogen and wherein the substituting pattern ($R^1$, $R^3$, $R^4$) is as defined in the following tables

| R1 | R3 | R4 |
|---|---|---|
| methyl | phenyl | H |
| ethyl | phenyl | H |
| n-butyl | phenyl | H |
| n-pentyl | phenyl | H |
| cyclopropyl | phenyl | H |
| cyclopentyl | phenyl | H |
| ethyl | 4-fluorophenyl | H |
| ethyl | 4-chlorophenyl | H |
| ethyl | 4-bromophenyl | H |
| ethyl | 4-iodophenyl | H |
| methyl | 4-(methylthio)phenyl | H |
| benzyl | phenyl | H |
| 4-methoxybenzyl | phenyl | H |
| methyl | 3,4,5-trimethoxyphenyl | H |
| methyl | 2,5-dimethoxyphenyl | H |
| methyl | H | benzyl |
| benzyl | H | benzyl |
| methyl | H | 4-methoxybenzyl |
| 4-methoxyphenylethyl | phenyl | methyl |
| phenyl | 4-chlorophenyl | p-tolyl |
| cyclohexyl | phenyl | methyl |
| n-propyl | 4-fluorophenyl | methyl |
| cyclohexyl | phenyl | phenyl |
| 4-methoxyphenylethyl | phenyl | phenyl |
| methoxyethyl | 4-bromophenyl | methyl |
| cyclopentyl | 4-bromophenyl | methyl |
| isobutyl | 4-chlorophenyl | p-tolyl |

| R1 | R3 | R4 |
|---|---|---|
| methyl | 4-fluorophenyl | H |
| methyl | 4-nitrophenyl | H |
| benzyl | 4-chlorophenyl | H |
| isopropyl | 4-biphenylyl | H |
| cyclohexyl | 4-cyanophenyl | H |
| cyclohexyl | 4-chlorophenyl | H |

-continued

| R1 | R3 | R4 |
|---|---|---|
| cyclododecyl | 4-nitrophenyl | H |
| methyl | 4-chlorophenyl | H |
| methyl | 4-cyanophenyl | H |
| 2-bromophenyl | phenyl | H |
| 3,4-dimethoxyphenylethyl | phenyl | H |
| 4-methoxyphenyl | 4-(trifluoromethyl)phenyl | H |
| methyl | H | 4-methoxyphenyl |
| 4-methoxybenzyl | H | 4-methoxybenzyl |
| H | 4-cyanophenyl | H |
| H | 4-nitrophenyl | H |
| ethyl | CONH-ethyl | H |
| cyclopropyl | morpholin-4-ylcarbony | H |
| cyclohexyl | 3-nitrophenyl | H |
| cyclododecyl | 3-nitrophenyl | H |
| 4-methoxybenzyl | 4-nitrophenyl | H |
| piperonyl | 4-fluorophenyl | H |
| hexyl | phenyl | methyl |
| methoxyethyl | 4-fluorophenyl | methyl |
| homoveratryl | 4-chlorophenyl | phenyl |
| tert-butyl | 4-chlorophenyl | 4-tolyl | and pharmaceutically acceptable salts, hydrates, solvates, prodrugs, stereoisomers or polymorphic forms thereof.

2. A substituted 2-aminoimidazole compound according to claim 1, being represented by the structural formula (I), wherein R3 is selected from the group consisting of ethylaminocarbonyl, morpholin-4-ylcarbonyl, 3,4-dichlorophenyl, 3,4-difluorophenyl, 4-biphenylyl, 4-bromophenyl, 4-(trifluoromethyl)-phenyl, 3-bromophenyl, 4-chlorophenyl, 4-fluorophenyl, phenyl, 4-iodophenyl, 4-methoxyphenyl, 4-tolyl, 4-hydroxyphenyl, 4-cyanophenyl, naphth-2-yl, 4-methylsulfonylphenyl, 4-(1-pyrrolidino)phenyl, 4-methylthiophenyl, 3-nitrophenyl and 4-nitrophenyl.

3. A substituted 2-aminoimidazole compound according to claim 1, being represented by the structural formula (I), wherein R4 is selected from the group consisting of hydrogen, methyl, phenyl and 4-tolyl.

4. A substituted 2-aminoimidazole compound according to claim 2, being represented by the structural formula (I), wherein R4 is selected from the group consisting of hydrogen, methyl, phenyl and 4-tolyl.

5. A substituted 2-aminoimidazole compound according to claim 1, being selected from the group consisting of N-methyl-5-(4-fluorophenyl)-1H-imidazol-2-amine, N-isopropyl-5-(4-methylphenyl)-1H-imidazol-2-amine, N-butyl-5-phenyl-1H-imidazol-2-amine, N-butyl-5-(4-fluorophenyl)-1H-imidazol-2-amine, N-butyl-5-(4-bromophenyl)-1H-imidazol-2-amine, N-butyl-5-(4-methoxyphenyl)-1H-imidazol-2-amine, N-cyclopropyl-5-(4-bromophenyl)-1H-imidazol-2-amine, N-cyclopentyl-5-phenyl-1H-imidazol-2-amine, N-cyclopentyl-5-(4-chlorophenyl)-1H-imidazol-2-amine, N-cyclopentyl-5-(4-bromophenyl)-1H-imidazol-2-amine, N-cyclopentyl-5-(4-nitrophenyl)-1H-imidazol-2-amine, N-benzyl-5-(4-chlorophenyl)-1H-imidazol-2-amine, N-piperonyl-5-(4-chlorophenyl)-1H-imidazol-2-amine, N-(2-(3-methoxyphenyl)-ethyl)-1H-imidazol-2-amine, N-methyl-5-(4-nitrophenyl)-1H-imidazol-2-amine, N-methyl-5-(4-hydroxyphenyl)-1H-imidazol-2-amine, N-methyl-5-(3,4-difluorophenyl)-1H-imidazol-2-amine, N-ethyl-5-(4-nitrophenyl)-1H-imidazol-2-amine, N-propyl-5-(3,4-dichlorophenyl)-1H-imidazol-2-amine, N-isopropyl-5-phenyl-1H-imidazol-2-amine, N-butyl-5-(4-nitrophenyl)-1H-imidazol-2-amine, N-isobutyl-5-(4-bromophenyl)-1H-imidazol-2-amine, N-isobutyl-5-(4-nitrophenyl)-1H-imidazol-2-amine, N-isobutyl-5-phenyl-1H-imidazol-2-amine, N-isobutyl-5-(4-chlorophenyl)-1H-imidazol-2-amine, N-pentyl-5-(4-chlorophenyl)-1H-imidazol-2-amine, N-pentyl-5-(4-bromophenyl)-1H-imidazol-2-amine, N-pentyl-5-(3,4-dichlorophenyl)-1H-imidazol-2-amine, N-hexyl-5-(4-fluorophenyl)-1H-imidazol-2-amine, N-octyl-5-(1-naphthyl)-1H-imidazol-2-amine, N-octyl-5-(4-chlorophenyl)-1H-imidazol-2-amine, N-octyl-5-(4-fluorophenyl)-1H-imidazol-2-amine, N-octyl-5-(3-bromophenyl)-1H-imidazol-2-amine, N-octyl-5-(4-bromophenyl)-1H-imidazol-2-amine, N-octyl-5-(4-nitrophenyl)-1H-imidazol-2-amine, N-octyl-5-(4-methoxyphenyl)-1H-imidazol-2-amine, N-octyl-5-(4-sulfonylphenyl)-1H-imidazol-2-amine, N-octyl-5-(3,4-dichlorophenyl)-1H-imidazol-2-amine, N-nonyl-5-(4-chloro-phenyl)-1H-imidazol-2-amine, N-cyclohexyl-5-(4-chlorophenyl)-1H-imidazol-2-amine, N-cyclohexyl-5-(4-methoxyphenyl)-1H-imidazol-2-amine, N-cyclohexyl-5-(4-methylthiophenyl)-1H-imidazol-2-amine, N-(3-methoxybenzyl)-5-(4-nitrophenyl)-1H-imidazol-2-amine, N-(3-methoxybenzyl)-5-(3,4-dichlorophenyl)-1H-imidazol-2-amine, N-(3-methoxybenzyl)-5-(4,1':4',1"-terphenyl)-1H-imidazol-2-amine, N-(3,4-methylenedioxybenzyl)-5-(4-fluoro-phenyl-1H-imidazol-2-amine, and N-(3,4-methylendioxybenzyl)-5-(1-naphthyl)-1H-imidazol-2-amine.

6. An imidazo[1,2-a]pyrimidinium salt according to claim 1, being represented by the structural formula (II) and wherein $X^-$ is a bromine or perchlorate anion.

7. An imidazo[1,2-a]pyrimidinium salt according to claim 1, being represented by the structural formula (II) and wherein R1 is selected from the group consisting of methyl, ethyl, cyclopropyl, isopropyl, propyl, butyl, isobutyl, tert-butyl, cyclobutyl, pentyl, cyclopentyl, hexyl, cyclohexyl, heptyl, octyl, cyclooctyl, nonyl, decyl, dodecyl, cyclododecyl, adamantly, phenyl, methoxyphenyl, benzyl, 2-(3-methoxyphenyl)ethyl, 2-(3,4-dimethoxy-phenyl)ethyl, 4-methoxybenzyl, 3-methoxybenzyl, 1,3-benzodioxol-5-ylmethyl, methoxyethyl, homoveratryl, piperonyl, undecyl, tridecyl, tetradecyl, cycloheptyl and tricyclo[3.3.1.13,7]-dec-1-yl.

8. An imidazo[1,2-a]pyrimidinium salt according to claim 6, being represented by the structural formula (II) and wherein R1 is selected from the group consisting of methyl, ethyl, cyclopropyl, isopropyl, propyl, butyl, isobutyl, tert-butyl, cyclobutyl, pentyl, cyclopentyl, hexyl, cyclohexyl, heptyl, octyl, cyclooctyl, nonyl, decyl, dodecyl, cyclododecyl, adamantly, phenyl, methoxyphenyl, benzyl, 2-(3-methoxyphenyl)ethyl, 2-(3,4-dimethoxy-phenyl)ethyl, 4-methoxybenzyl, 3-methoxybenzyl, 1,3-benzodioxol-5-ylmethyl, methoxyethyl, homoveratryl, piperonyl, undecyl, tridecyl, tetradecyl, cycloheptyl and tricyclo[3.3.1.13,7]-dec-1-yl.

9. An imidazo[1,2-a]pyrimidinium salt according to claim 1, being represented by the structural formula (II) and wherein R3 is selected from the group consisting of ethylaminocarbonyl, morpholin-4-ylcarbonyl, phenyl, 4-bromophenyl, 4-chlorophenyl, 4-fluorophenyl, 3-fluorophenyl, 4-iodophenyl, 4-nitrophenyl, 3-nitrophenyl, 4-biphenylyl, 4-methoxyphenyl, 4-methylthiophenyl, 4-tolyl, 4-hydroxyphenyl, naphth-2-yl, 4-cyanophenyl, 2,5-dimethoxyphenyl, 3,4,5-trimethoxyphenyl, 3,4-dichlorophenyl, diphenyl-methyl, 4-methylsulfonylphenyl, 4-(trifluoromethyl)phenyl, 4-(1-pyrrolidino)phenyl and 3,4-methylenedioxyphenyl.

10. An imidazo[1,2-a]pyrimidinium salt according to claim 6, being represented by the structural formula (II) and wherein R3 is selected from the group consisting of ethylaminocarbonyl, morpholin-4-ylcarbonyl, phenyl, 4-bromophenyl, 4-chlorophenyl, 4-fluorophenyl, 3-fluorophenyl, 4-iodophenyl, 4-nitrophenyl, 3-nitrophenyl, 4-biphenylyl, 4-methoxyphenyl, 4-methylthiophenyl, 4-tolyl, 4-hydroxyphenyl, naphth-2-yl, 4-cyanophenyl, 2,5-dimethoxyphenyl, 3,4,5-trimethoxyphenyl, 3,4-dichlorophenyl, diphenyl-methyl, 4-methylsulfonylphenyl, 4-(trifluoromethyl)phenyl, 4-(1-pyrrolidino)phenyl and 3,4-methylenedioxyphenyl.

11. An imidazo[1,2-a]pyrimidinium salt according to claim 8, being represented by the structural formula (II) and wherein R3 is selected from the group consisting of ethylaminocarbonyl, morpholin-4-ylcarbonyl, phenyl, 4-bromophenyl, 4-chlorophenyl, 4-fluorophenyl, 3-fluorophenyl, 4-iodophenyl, 4-nitrophenyl, 3-nitrophenyl, 4-biphenylyl, 4-methoxyphenyl, 4-methylthiophenyl, 4-tolyl, 4-hydroxyphenyl, naphth-2-yl, 4-cyanophenyl, 2,5-dimethoxyphenyl, 3,4,5-trimethoxyphenyl, 3,4-dichlorophenyl, diphenyl-methyl, 4-methylsulfonylphenyl, 4-(trifluoromethyl)phenyl, 4-(1-pyrrolidino)phenyl and 3,4-methylenedioxyphenyl.

12. An imidazo[1,2-a]pyrimidinium salt according to claim 1, being selected from the group consisting of 1-(3-Azidopropyl)-2-hydroxy-2-phenyl-2,3-dihydro-1H-imidazo[1,2-a]pyrimidin-4-ium bromide, 1-(2-Azidoethyl)-2-(4-bromophenyl)-2-hydroxy-2,3-dihydro-1H-imidazo[1,2-a]pyrimidin-4-ium bromide, 1-(2-Azidoethyl)-2-hydroxy-2-phenyl-2,3-dihydro-1H-imidazo[1,2-a]pyrimidin-4-ium bromide, 1-(2-Azidoethyl)-2-hydroxy-2-(naphth-1-yl)-2,3-dihydro-1H-imidazo[1,2-a]pyrimidin-4-ium bromide, 1-(3-Azidopropyl)-2-(4-bromophenyl)-2-hydroxy-2,3-dihydro-1H-imidazo[1,2-a]pyrimidin-4-ium bromide, 1-(2-Azidoethyl)-2-(3,4-dichlorophenyl)-2-hydroxy-2,3-dihydro-1H-imidazo[1,2-a]pyrimidin-4-ium bromide, 1-(3-Azidopropyl)-2-(3,4-dichlorophenyl)-2-hydroxy-2,3-dihydro-1H-imidazo[1,2-a]pyrimidin-4-ium bromide, 1-(3-Azidopropyl)-2-hydroxy-2-(morpholine-4-carbonyl)-2,3-dihydro-1H-imidazo[1,2-a]pyrimidin-4-ium bromide, 1-(2-Azidoethyl)-2-hydroxy-2-(morpholine-4-carbonyl)-2,3-dihydro-1H-imidazo[1,2-a]pyrimidin-4-ium bromide, 1-(2-Azidoethyl)-2-(4-fluorophenyl)-2-hydroxy-2,3-dihydro-1H-imidazo[1,2-a]pyrimidin-4-ium bromide, 1-(2-Azidoethyl)-2-(4-chlorophenyl)-2-hydroxy-3-p-tolyl-2,3-dihydro-1H-imidazo[1,2-a]pyrimidin-4-ium bromide, 1-(3-Azidopropyl)-2-hydroxy-2,3-diphenyl-2,3-dihydro-1H-imidazo[1,2-a]pyrimidin-4-ium bromide, 1-(4-Azidobutyl)-2-hydroxy-2-phenyl-2,3-dihydro-1H-imidazo[1,2-a]pyrimidin-4-ium bromide, 1-(4-Azidobutyl)-2-(4-bromophenyl)-2-hydroxy-2,3-dihydro-1H-imidazo[1,2-a]pyrimidin-4-ium bromide, 1-(4-Azidobutyl)-2-hydroxy-2-(naphth-1-yl)-2,3-dihydro-1H-imidazo[1,2-a]pyrimidin-4-ium bromide, 1-(4-Azidobutyl)-2-(3,4-dichlorophenyl)-2-hydroxy-2,3-dihydro-1H-imidazo[1,2-a]pyrimidin-4-ium bromide, 1-(4-Azidobutyl)-2-hydroxy-2-(morpholine-4-carbonyl)-2,3-dihydro-1H-imidazo[1,2-a]pyrimidin-4-ium bromide, 1-(4-Azidobutyl)-2-(4-fluorophenyl)-2-hydroxy-2,3-dihydro-1H-imidazo[1,2-a]pyrimidin-4-ium bromide, 1-(4-Azidobutyl)-2-(4-chlorophenyl)-2-hydroxy-3-p-tolyl-2,3-dihydro-1H-imidazo[1,2-a]pyrimidin-4-ium bromide, 1-(2-Azidoethyl)-2-hydroxy-2,3-diphenyl-2,3-dihydro-1H-imidazo[1,2-a]pyrimidin-4-ium bromide, 1-(3-Azidopropyl)-2-hydroxy-2-(naphth-1-yl)-2,3-dihydro-1H-imidazo[1,2-a]pyrimidin-4-ium bromide, and 1-(4-Azidobutyl)-2-hydroxy-2,3-diphenyl-2,3-dihydro-1H-imidazo[1,2-a]pyrimidin-4-ium bromide.

13. A compound selected from the group consisting of N-(1-azidomethyl)pyrimidin-2-amine, N-(2-azidoethyl)pyrimidin-2-amine, N-(3-azidopropyl)pyrimidin-2-amine, N-(4-azidobutyl)pyrimidin-2-amine, N-(5-azidopentyl)pyrimidin-2-amine, N-(6-azidohexyl)pyrimidin-2-amine, N-(7-azidoheptyl)pyrimidin-2-amine, N-(8-azidooctyl)pyrimidin-2-amine, N-(9-azidononyl)pyrimidin-2-amine, N-(10-azidodecyl)pyrimidin-2-amine, N-(11-azidoundecyl)pyrimidin-2-amine, N-(12-azidododecyl)pyrimidin-2-amine, N-(13-azidotridecyl)pyrimidin-2-amine, N-(14-azidotetradecyl)pyrimidin-2-amine, N-(15-azidopentadecyl)pyrimidin-2-amine, N-(16-azidohexadecyl)pyrimidin-2-amine, N-(17-azidoheptadecyl)pyrimidin-2-amine, N-(18-azidooctadecyl)pyrimidin-2-amine and N-(19-azidononadecyl)pyrimidin-2-amine.

14. A process for producing a compound according to claim 13, comprising the step of reacting an azidoalkylamine wherein the alkyl group has 1 to 20 carbon atoms with a 2-halopyrimidine.

15. A substituted 2-aminoimidazole compound according to claim 1, being represented by the structural formula (III)

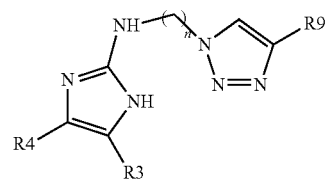

wherein R3, R4, and n are as defined in claim 1, and wherein R9 is selected from the group consisting of hydrogen, $C_{1-20}$ alkyl optionally substituted with amino, $C_{1-20}$ alkoxy, $C_{2-20}$ alkenyl, $C_{2-20}$ alkynyl, $C_{3-12}$ cycloalkyl, $C_{3-12}$ cycloalkenyl, aryl optionally substituted with one or more substituent(s) independently selected from the group consisting of $C_{1-4}$ alkyl and $C_{1-4}$ alkoxy, methylamino, heterocyclic and heteroaryl.

16. A process for producing an imidazo[1,2-a]pyrimidinium salt according to claim 1 being represented by the structural formula (II) wherein R4 and R5 are each independently selected from the group consisting of $C_{1-20}$ alkyl, $C_{2-20}$ alkenyl, $C_{2-20}$ alkynyl, $C_{3-12}$ cycloalkyl and $C_{3-12}$ cycloalkenyl, and wherein R1 is $C_{1-20}$ alkyl substituted with one terminal azido group, comprising the step of reacting a compound according to claim 17 with an α-bromocarbonyl compound represented by the structural formula R4CHBr—CO—R3 wherein R4 and R3 are as defined in claim 1.

17. A process for producing a substituted 2-aminoimidazole compound represented by the structural formula (III):

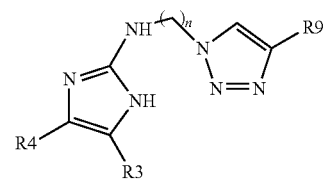

wherein R3, R4, and n are as defined in claim 1, and wherein R9 is selected from the group consisting of hydrogen, $C_{1-20}$ alkyl optionally substituted with amino, $C_{1-20}$ alkoxy, $C_{2-20}$ alkenyl, $C_{2-20}$ alkynyl, $C_{3-12}$ cycloalkyl, $C_{3-12}$ cycloalkenyl, aryl optionally substituted with one or more substituent(s) independently selected from the group consisting of $C_{1-4}$ alkyl and $C_{1-4}$ alkoxy, methylamino, heterocyclic and heteroaryl, comprising the step of reacting an imidazo[1,2-a]pyrimidinium salt according to claim 1 being represented by the structural formula (II) wherein R4 and R5 are each independently selected from the group consisting of $C_{1-20}$ alkyl, $C_{2-20}$ alkenyl, $C_{2-20}$ alkynyl, $C_{3-12}$ cycloalkyl and $C_{3-12}$ cycloalkenyl, and wherein R1 is $C_{1-20}$ alkyl substituted with one terminal azido group, with an optionally substituted acetylene represented by the structural formula HCCR9, wherein R9 is selected from the group consisting of hydrogen, $C_{1-20}$ alkyl optionally substituted with amino, halogen or dimethylamino, $C_{1-20}$ alkoxy, $C_{2-20}$ alkenyl, $C_{2-20}$ alkynyl, $C_{3-12}$ cycloalkyl, $C_{3-12}$ cycloalkenyl, aryl optionally substituted with one or more substituent(s) independently selected from the group consisting of $C_{1-4}$ alkyl and $C_{1-4}$ alkoxy, methylamino, heterocyclic and heteroaryl.

18. A substituted 2-aminoimidazole compound according to claim 15, being selected from the group consisting of 5-phenyl-N-(3-(4-phenyl-1H-1,2,3-triazol-1-yl)propyl)-1H-imidazol-2-amine, 5-(4-Bromophenyl)-N-(2-(4-(4-methoxyphenyl)-1H-1,2,3-triazol-1-yl)ethyl)-1H-imidazol-2-amine, 5-Phenyl-N-(2-(4-phenyl-1H-1,2,3-triazol-1-yl)ethyl)-1H-imidazol-2-amine, 5-(4-Bromophenyl)-N-(2-(4-p-tolyl-1H-1,2,3-triazol-1-yl)ethyl)-1H-imidazol-2-amine, N-(2-(4-(4-Butylphenyl)-1H-1,2,3-triazol-1-yl)ethyl)-5-(naphth-1-yl)-1H-imidazol-2-amine, 5-(4-Bromophenyl)-N-(2-(4-heptyl-1H-1,2,3-triazol-yl)ethyl)-1H-imidazol-2-amine, 5-(4-Bromophenyl)-N-(3-(4-(4-pentylphenyl)-1H-1,2,3-triazol-1-yl)propyl)-1H-imidazol-2-amine, 5-(3,4-Dichlorophenyl)-N-(2-(4-(4-heptylphenyl)-1H-1,2,3-triazol-1-yl)ethyl)-1H-imidazol-2-amine, 5-(3,4-Dichlorophenyl)-N-(3-(4-((methylamino)methyl)-1H-1,2,3-triazol-1-yl)propyl)-1H-imidazol-2-amine, N-(3-(4-(2-aminopropan-2-yl)-1H-1,2,3-triazol-1-yl)propyl)-5-(4-bromophenyl)-1H-imidazol-2-amine, 5-(3,4-Dichlorophenyl)-N-(2-(4-cyclohexyl-1H-1,2,3-triazol-1-yl)ethyl)-1H-imidazol-2-amine, 5-(3,4-Dichlorophenyl)-N-(2-(4-propyl-1H-1,2,3-triazol-1-yl)ethyl)-1H-imidazol-2-amine, 5-(3,4-Dichlorophenyl)-N-(3-(4-propyl-1H-1,2,3-triazol-1-yl)propyl)-1H-imidazol-2-amine, 5-(4-Bromophenyl)-N-(2-(4-propyl-1H-1,2,3-triazol-1-yl)ethyl)-1H-imidazol-2-amine, 5-(4-Bromophenyl)-N-(3-(4-propyl-1H-1,2,3-triazol-1-yl)propyl)-1H-imidazol-2-amine, (2-(3-(4-Propyl-1H-1,2,3-triazol-1-yl)propylamino)-1H-imidazol-5-yl)(morpholino)methanone, (2-(2-(4-Propyl-1H-1,2,3-triazol-1-yl)ethylamino)-1H-imidazol-5-yl)(morpholino)metha-none, N-(2-(4-(Cyclopentylmethyl)-1H-1,2,3-triazol-1-yl)ethyl)-5-(4-fluorophenyl)-1H-imidazol-2-amine, N-(2-(4-Cyclopropyl-1H-1,2,3-triazol-1-yl)ethyl)-5-(4-fluorophenyl)-1H-imidazol-2-amine, 5-(4-Chlorophenyl)-N-(2-(4-cyclopentyl-1H-1,2,3-triazol-1-yl)ethyl)-4-p-tolyl-1H-imidazol-2-amine, N-(3-(4-(4-tert-Butylphenyl-1H-1,2,3-triazol-1-yl)propyl)-5-(3,4-dichlorophenyl)-1H-imidazol-2-amine, 5-(3,4-Dichlorophenyl)-N-(3-(4-(thiophen-3-yl)-1H-1,2,3-triazol-1-yl)propyl)-1H-imidazol-2-amine, 5-(4-Bromophenyl)-N-(2-(4-cyclopropyl-1H-1,2,3-triazol-1-yl)ethyl)-1H-imidazol-2-amine, 5-(4-Bromophenyl)-N-(2-(4-cyclohexyl-1 H-1,2,3-triazol-1-yl)ethyl)-1H-imidazol-2-amine, and N-(3-(4-Heptyl-1H-1,2,3-triazol-1-yl)propyl)-4,5-diphenyl-1H-imidazol-2-amine.

* * * * *

UNITED STATES PATENT AND TRADEMARK OFFICE
CERTIFICATE OF CORRECTION

PATENT NO.        : 8,906,915 B2
APPLICATION NO.   : 13/526235
DATED             : December 9, 2014
INVENTOR(S)       : Sigrid De Keersmaecker et al.

It is certified that error appears in the above-identified patent and that said Letters Patent is hereby corrected as shown below:

In The Claims

Column 78, Line 36-37, replace
"hydroxy, acetyl, $C_{1-20}$ alkyl, halo $C_{1-20}$ alkyl, $C_{1-20}$ alkyl, $C_{1-20}$ alkoxy, halo $C_{1-20}$ alkoxy,"
with --hydroxy, acetyl, $C_{1-20}$ alkyl, halo $C_{1-20}$ alkyl, $C_{1-20}$ alkoxy, halo $C_{1-20}$ alkoxy,--.

Column 84, Line 40, replace "claim 17" with --claim 13--.

Signed and Sealed this
Twelfth Day of May, 2015

Michelle K. Lee
*Director of the United States Patent and Trademark Office*